United States Patent
Watson et al.

(10) Patent No.: US 6,706,735 B2
(45) Date of Patent: Mar. 16, 2004

(54) 2-SUBSTITUTED-4-NITROGEN HETEROCYCLES AS MODULATORS OF CHEMOKINE RECEPTOR ACTIVITY

(75) Inventors: Paul S. Watson, Middletown, DE (US); Soo S. Ko, Hockessin, DE (US); George V. DeLucca, Wilmington, DE (US); John V. Duncia, Hockessin, DE (US); Joseph B. Santella, III, Springfield, PA (US); Dean A. Wacker, Chadds Ford, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/180,756

(22) Filed: Jun. 26, 2002

(65) Prior Publication Data

US 2003/0144273 A1 Jul. 31, 2003

Related U.S. Application Data

(62) Division of application No. 09/465,301, filed on Dec. 17, 1999, now Pat. No. 6,441,001.
(60) Provisional application No. 60/112,716, filed on Dec. 18, 1998.

(51) Int. Cl.[7] .............. C07D 207/00; C07D 295/00; C07D 403/02; C07D 231/02; A61K 31/44
(52) U.S. Cl. .............. 514/326; 548/567; 548/518; 548/314.7; 548/195; 548/196; 548/364.1; 548/251; 548/252; 548/527; 548/517; 548/467; 548/362.5; 548/306.1; 548/163; 548/179; 548/180; 548/217; 514/408; 514/326; 514/422; 514/397; 514/371; 514/407; 514/381; 514/343; 514/375; 514/414; 514/405; 514/394; 514/367; 546/208; 546/276.4
(58) Field of Search .............. 548/567, 518, 548/314.7, 195, 196, 364.1, 251, 252, 527, 517, 467, 362.5, 306.1, 163, 179, 180, 217; 514/408, 326, 422, 397, 371, 407, 381, 343, 375, 414, 405, 394, 367; 546/208, 276.4

(56) References Cited

U.S. PATENT DOCUMENTS 6,331,541 B1    12/2001   Ko et al.
6,331,545 B1    12/2001   Ko et al.
6,444,686 B1    9/2002    Ko et al.

FOREIGN PATENT DOCUMENTS

| EP | 0747357 | 12/1996 |
|----|---------|---------|
| WO | 9519344 | 7/1995  |
| WO | 9717954 | 5/1997  |
| WO | 9722597 | 6/1997  |
| WO | 9727752 | 8/1997  |
| WO | 9825604 | 6/1998  |
| WO | 9825617 | 6/1998  |
| WO | 9831364 | 7/1998  |
| WO | 0035449 | 6/2000  |
| WO | 0035452 | 6/2000  |
| WO | 0035453 | 6/2000  |
| WO | 0035454 | 6/2000  |
| WO | 0035877 | 6/2000  |

OTHER PUBLICATIONS

Capet et al. Chem. Abstract 120:217658.*

Giovannini et al. Chem. Abstract 128:180302.*

CAS printout of Fontanella et al. Chem. Abs. 79:78688, 1973.*

Horuk et al, Chemokine Receptor Antagonists, Med. Res. Rev., 2000, vol. 20, pp. 155–168.

* cited by examiner

Primary Examiner—Richard L. Raymond
Assistant Examiner—Hong Liu
(74) Attorney, Agent, or Firm—Mary K. VanAtten

(57) ABSTRACT

The present application describes modulators of CCR3 of formula (I):

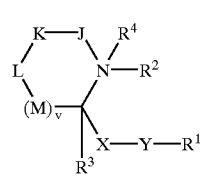

or pharmaceutically acceptable salt forms thereof, useful for the prevention of asthma and other allergic diseases.

35 Claims, No Drawings

2-SUBSTITUTED-4-NITROGEN HETEROCYCLES AS MODULATORS OF CHEMOKINE RECEPTOR ACTIVITY

This is a division of application Ser. No. 09/465,301 filed Dec. 17,1999 now U.S. Pat. No. 6,441,001.

FIELD OF THE INVENTION

This invention relates generally to modulators of chemokine receptor activity, pharmaceutical compositions containing the same, and methods of using the same as agents for treatment and prevention of asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1a, MIP-1b, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1a, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5](Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1a, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1a, RANTES, MIP-1b] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1b] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxyiruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as $CXCR^4$, $CCR^2$, $CCR^3$, $CCR^5$ and $CCR^8$, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of $CCR^3$ expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

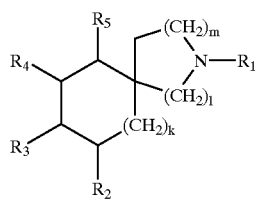

wherein $R_1$ is $C_{1-6}$ alkyl, optionally substituted with functional groups such as —$NR^8CONHR^9$, and $R^8$ and $R^9$ may be phenyl further substituted with hydroxy, alkyl, cyano, halo and haloalkyl. Such spiro compounds are not considered part of the present invention.

U.S. Pat. No. 5,264,420 discloses fibrinogen receptor antagonists comprising carbon-linked disubstituted heterocyclic amines as a component of a multiamidic moiety:

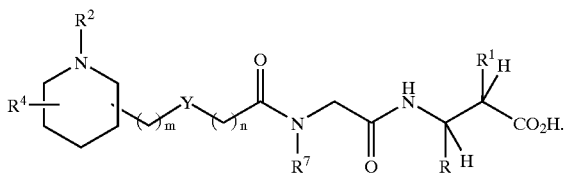

These compounds can be distinguished from the present invention by the nature of the multiamidic moiety.

WO 96/31111 discloses farnesyl protein transferase inhibitors where $R^2$ can be $C_{1-6}$ alkyl, optionally substituted with functional groups such as $-NR^8COR^9$ and $-NR^8CONR^9R^{10}$ wherein $R^9$ may be phenyl which can have further substitution.

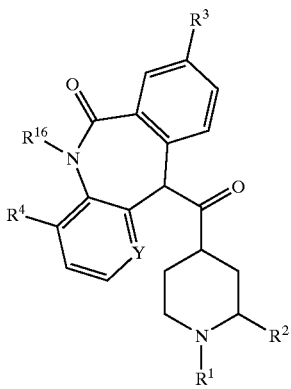

Such compounds which contain tri-substituted ketones are not contemplated by the present invention.

WO 96/11200 discloses purine and guanine compounds as inhibitors of purine nucleoside phosphorylase:

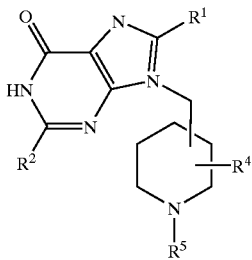

wherein $R^4$ can be $C_{1-6}$ alkyl, optionally substituted with functional groups such as $-NHCONHAr$ where Ar may be phenyl further substituted. Such guanines and purines as substituents on heterocycles are not considered part of the present invention.

Compounds known in the art are readily distinguished structurally by either the nature or location of the linking chain, or other possible substitution patterns of the present invention. The prior art does not disclose nor suggest the unique combination of structural fragments which embody these novel heterocycles as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating allergic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

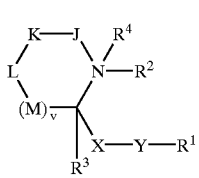

(I)

or stereoisomers or pharmaceutically acceptable salts thereof, wherein J, K, L, M, $R^1$, $R^2$, $R^3$, and $R^4$ are defined below are effective modulators of chemokine activity.

DETAILED DESCRIPTION OF PREFERRED EMBODIMENTS

Thus, in a first embodiment, the present invention provides novel compounds of formula I:

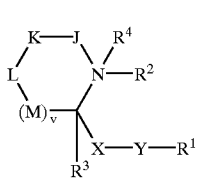

(I)

or stereoisomers or pharmaceutically acceptable salts thereof, wherein:

J is selected from $CH_2$ and $CHR^5$;

K and L are independently selected from $CR^5R^6$ and $CR^6R^6$;

M, at each occurrence, is selected from $CR^5R^6$ and $CR^6R^6$;

with the proviso that at least one of J, K, L, or M contains an $R^5$;

X is selected from $(CR^7R^{7'})_q$—S—$(CR^7R^{7'})_q$, $(CR^7R^{7'})_q$— O—$(CR^7R^{7'})_q$, $(CR^7R^{7'})_q$—$NR^{7'}(CR^7R^{7'})_q$, $(CR^7R^{7'})_r$—C(O)—$(CR^7R^{7'})_q$, $C_{1-6}$ alkylene substituted with 0–5 $R^7$, $C_{2-10}$ alkenylene substituted with 0–5 $R^7$, $C_{2-10}$ alkynylene substituted with 0–5 $R^7$, and $(CR^7R^{7'})_r$—A—$(CR^7R^{7'})_t$ substituted with 0–3 $R^8$;

with the proviso that when $R^7$ or $R^{7'}$ is bonded to the same carbon as Y, $R^7$ is not halogen, cyano, or bonded through a heteroatom;

A is $C_{3-6}$ carbocyclic residue;

Y is selected from $NR^{11}C(=O)NR^{11}$, $NR^{11}C(=S)NR^{11}$, $NR^{11}C$ $(=NR^a)NR^{11}$, $NR^{11}C$ $(=CHCN)NR^{11}$, $NR^{11}C$ $(=CHNO_2)NR^{11}$, $NR^{11}C(=C(CN)_2)NR^{11}$, $NR^{11}$, $C(O)$, $S(O)_2NR^{11}$, $NR^{11}S(O)_2$, $NR^{11}S(O)_2NR^{11}$, $C(O)NR^{11}$, $NR^{11}C(O)$, $NR^{11}C(O)O$, $OC(O)NR^{11}$, and $S(O)_p$;

$R^a$ is selected from H, $C_{1-6}$ alkyl, $C_{3-6}$ cycloalkyl, OH, CN, O—$C_{1-6}$ alkyl, and $(CH_2)_w$phenyl;

$R^1$ is selected from a $(CR^1R^{1''})_r$—$C_{3-10}$ carbocyclic residue substituted with 0–5 $R^9$ and a $(CR^1R^{1''})_r$-5–10 membered heterocyclic system containing 1–4 heteroatoms selected from N, O, and S, substituted with 0–3 $R^9$;

$R^{1'}$ and $R^{1''}$, at each occurrence, are selected from H, $C_{1-6}$ alkyl, $(CH_2)_rC_{3-6}$ cycloalkyl, and phenyl;

$R^2$, at each occurrence, is selected from H, $C_{1-8}$ alkyl, $(CR^{2'}R^{2''})_qNR^{12a}R^{12a'}$, $(CR^{2'}R^{2''})_wOH$, $(CR^{2'}R^{2''})_wO(CR^{2'}R^{2''})_rR^{12d}$, $(CR^{2'}R^{2''})_qSH$, $(CR^{2'}R^{2''})_rC(O)H$, $(CR^{2'}R^{2''})_qS(CR^{2'}R^{2''})_rR^{12d}$, $(CR^{2'}R^2)_rC(O)OH$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a'}$, $(CR^{2'}R^{2''})_rC(NR^a)NR^{12a}R^{12a'}$, $(CR^{2'}R^{2''})_rC(NR^a)R^{12b}$, $(CR^{2'}R^{2''})_rC(O)NR^{12a}R^{12a'}$, $(CR^{2'}R^{2''})_rNR^{12f}C(O)(CR^{2'}R^{2''})_rR^{12b}$, $(CR^{2'}R^{2''})_rC(O)O(CR^{2'}R^{2''})_qR^{12d}$, $(CR^{2'}R^{2''})_wOC(O)(CR^{2'}R^{2''})_rR^{12b}$, $(CR^{2'}R^{2'})_wS(O)_p(CR^{2'}R^{2''})_rR^{12b}$, $(CR^{2'}R^{2''})_wS(O)_2NR^{12a}R^{12a'}$, $(CR^{2'}R^{2''})_qNR^{12f}S(O)_2(CR^{2'}R^{2''})_rR^{12b}$, $C_{1-6}$ haloalkyl, $C_{2-8}$ alkenyl substituted with 0–3 $R^{12c}$, $C_{2-8}$ alkynyl substituted with 0–3 $R^{12c}$, a $(CR^{2'}R^{2''})_r$—$C_{3-10}$ carbocyclic residue substituted with 0–3 $R^{12c}$, and a $(CH_2)_r$-5–10 membered heterocyclic system containing 1–4 heteroatoms selected from N, O, and S, substituted with 0–2 $R^{12c}$;

alternatively, $R^2$ is an amino acid residue;

$R^{2'}$ and $R^{2''}$, at each occurrence, are selected from H, $C_{2-8}$ alkenyl, $C_{2-8}$ alkynyl, $(CF_2)_rCF_3$, $(CH_2)_rCN$, $(CH_2)_rNO_2$, $(CF_2)_rCF_3$, $(CH_2)_rNR^{2a}R^{2a'}$, $(CH_2)_rOH$, $(CH_2)_rOR^{2b}$, $(CH_2)_rSH$, $(CH_2)_rSR^{2b}$, $(CH_2)_rC(O)OH$, $(CH_2)_rC(O)R^{2b}$, $(CH_2)_rC(O)NR^{2a}R^{2a'}$, $(CH_2)_rNR^{2d}C(O)R^{2a}$, $(CH_2)_rC(O)OR^{2b}$, $(CH_2)_rOC(O)R^{2b}$, $(CH_2)_rS(O)_pR^{2b}$, $(CH_2)_rS(O)_2NR^{2a}R^{2a'}$, $(CH_2)_rNR^{2d}S(O)_2R^{2b}$, $C_{1-6}$ haloalkyl, a $(CR^{2'}R^{2''})_r$—$C_{3-10}$ carbocyclic residue substituted with 0–5 $R^{2c}$, and a $(CH_2)_r$-5–10 membered heterocyclic system containing 1–4 heteroatoms selected from N, O, and S, substituted with 0–2 $R^{2c}$;

$R^{2a}$ and $R^{2a'}$, at each occurrence, are selected from H, $C_{1-6}$ alkyl, $C_{3-6}$ cycloalkyl, and phenyl substituted with 0–3 $R^{2c}$;

$R^{2b}$, at each occurrence, is selected from $C_{1-6}$ alkyl, $C_{3-6}$ cycloalkyl, and phenyl substituted with 0–3 $R^{2c}$;

$R^{2c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{2d}R^{2d}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{2b}$, $(CH_2)_rC(O)NR^{2d}R^{2d}$, $(CH_2)_rNR^{2d}C(O)R^{7a}$, $(CH_2)_rC(O)OC_{1-4}$ alkyl, $(CH_2)_rOC(O)R^{2b}$, $(CH_2)_rC(=NR^{2d})NR^{2d}R^{2d}$, $(CH_2)_rS(O)_pR^{2d}$, $(CH_2)_rNHC(=NR^{2d})NR^{2d}R^{2d}$, $(CH_2)_rS(O)_2NR^{2d}R^{2d}$, $(CH_2)_rNR^{2d}S(O)_2R^{2b}$, and $(CH_2)_r$phenyl substituted with 0–3 $R^{9e}$;

$R^{2d}$, at each occurrence, is selected from H, $C_{1-6}$ alkyl, and $C_{3-6}$ cycloalkyl;

$R^3$ is selected from H, $C_{1-6}$ alkyl, $C_{2-8}$ alkenyl, $C_{2-8}$ alkynyl, $C_{3-6}$ cycloalkyl, $(CF_2)_rCF_3$, $(CH_2)_rNR^{3a}R^{3a'}$, $(CH_2)_qOH$, $(CH_2)_qOR^{3b}$, $(CH_2)_qSH$, $(CH_2)_qSR^{3b}$, $(CH_2)_rC(O)OH$, $(CH_2)_rC(O)R^{3b}$, $(CH_2)_rC(O)NR^{3a}R^{3a'}$, $(CH_2)_rNR^{3d}C(O)R^{3a}$, $(CH_2)_rC(O)OR^{3b}$, $(CH_2)_qOC(O)R^{3b}$, $(CH_2)_rS(O)_pR^{3b}$, $(CH_2)_rS(O)_2NR^{3a}R^{3a'}$, $(CH_2)_qNR^{3d}S(O)_2R^{3b}$, and $(CH_2)_r$-phenyl substituted with 0–3 $R^{3c}$;

$R^{3a}$ and $R^{3a'}$, at each occurrence, are selected from H, $C_{1-6}$ alkyl, $C_{3-6}$ cycloalkyl, and phenyl substituted with 0–3 $R^{3c}$;

$R^{3b}$, at each occurrence, is selected from $C_{1-6}$ alkyl, $C_{3-6}$ cycloalkyl, and phenyl substituted with 0–3 $R^{3c}$;

$R^{3c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{3d}R^{3d}$;

$R^{3d}$, at each occurrence, is selected from H, $C_{1-6}$ alkyl, and $C_{3-6}$ cycloalkyl;

$R^4$ is absent, taken with the nitrogen to which it is attached to form an N-oxide, or selected from $C_{1-8}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^5$ is selected from a $(CR^{5'}R^{5''})_r$—$C_{3-10}$ carbocyclic residue substituted with 0–5 $R^{10}$ and a $(CR^{5'}R^{5''})_r$-5–10 membered heterocyclic system containing 1–4 heteroatoms selected from N, O, and S, substituted with 0–3 $R^{10}$;

$R^{5'}$ and $R^{5''}$, at each occurrence, are selected from H, $C_{1-6}$ alkyl, $(CH_2)_rC_{3-6}$ cycloalkyl, and phenyl;

alternatively, $R^5$ and $R^6$ join to form a 5, 6, or 7-membered spirocycle, containing 0–3 heteroatoms selected from N, O, and S, substituted with 0–3 $R^{16}$;

$R^6$, at each occurrence, is selected from H, $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_t$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^7$ is selected from $C_{1-8}$ alkyl, $C_{2-8}$ alkenyl, $C_{2-8}$ alkynyl, F, Cl, Br, I, $(CH_2)_rOH$, $(CH_2)_rSH$, $(CH_2)_rOR^{7d}$, $(CH_2)_rSR^{7d}$, $(CH_2)_rNR^{7a}R^{7a'}$, $C_{1-6}$ haloalkyl, a $(CH_2)_r$—$C_{3-6}$ carbocyclic residue substituted with 0–3 $R^{7c}$;

$R^{7a}$ and $R^{7a'}$, at each occurrence, are selected from H, $C_{1-6}$ alkyl, $(CH_2)_rC_{3-6}$ cycloalkyl, and phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ cycloalkyl, and phenyl substituted with 0–3 $R^{7e}$;

$R^{7c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-6}$ alkyl, OH, SH, $(CH_2)_rSC_{1-6}$ alkyl, $(CH_2)_rNR^{7d}R^{7d}$, $C(O)C_{1-6}$ alkyl, and $(CH_2)_r$phenyl;

$R^{7d}$, at each occurrence, is selected from H, $C_{1-6}$ alkyl, and $C_{3-6}$ cycloalkyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, $C_{3-6}$ cycloalkyl, and phenyl;

$R^{7'}$, at each occurrence, is selected from H, $C_{1-8}$ alkyl, $C_{2-8}$ alkenyl, $C_{2-8}$ alkynyl, $(CH_2)_qOH$, $(CH_2)_qSH$, $(CH_2)$ $_qOR^{7b}$, $(CH_2)_qSR^{7b}$, $(CH_2)_qNR^{7a}R^{7a'}$, $(CH_2)_rC(O)OH$, $C_{1-6}$ haloalkyl, a $(CH_2)_r$—$C_{3-6}$ carbocyclic residue substituted with 0–3 $R^{7c}$;

$R^8$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{8a}R^{8a'}$, $(CHR')_rOH$, $(CHR')_rO(CHR')_rR^{8d}$, $(CHR')_rSH$, $(CHR')_rC(O)H$, $(CHR')_rS(CHR')_rR^{8d}$, $(CHR')_rC(O)OH$, $(CHR')_rC(O)(CHR')_rR^{8b}$, $(CHR')_rC(O)NR^{8a}R^{8a'}$, $(CHR')_rNR^{8f}C(O)$ $(CHR')_rR^{8b}$, $(CHR')_rC(O)O(CHR')_rR^{8d}$, $(CHR')_rOC(O)(CHR')_rR^{8b}$, $(CHR')_rC(=NR^{8f})NR^{8a}R^{8a'}$, $(CHR')_rNHC(=NR^{8f})NR^{8f}R^{8f}$, $(CHR')_rS(O)_p(CHR')_rR^{8b}$, $(CHR')_rS(O)_2NR^{8a}R^{8a'}$, $(CHR')_rNR^{8f}S(O)_2(CHR')_rR^{8b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{8e}$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{8e}$;

$R^{8a}$ and $R^{8a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–2 $R^{8e}$;

$R^{8b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{8e}$, and $(CH_2)_r$-5–6 membered heterocyclic system containing 1–4 heteroatoms selected from N, O, and S, substituted with 0–2 $R^{8e}$;

$R^{8d}$, at each occurrence, is selected from $C_{2-8}$ alkenyl, $C_{2-8}$ alkynyl, $C_{1-6}$ alkyl substituted with 0–3 $R^{8e}$, a $(CH_2)_r$—$C_{3-10}$ carbocyclic residue substituted with 0–3 $R^{8e}$, and a $(CH_2)_r$ 5–6 membered heterocyclic system containing 1–4 heteroatoms selected from N, O, and S, substituted with 0–3 $R^{8e}$;

$R^{8e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{8f}R^{8f}$, and $(CH_2)_r$phenyl;

$R^{8f}$, at each occurrence, is selected from H, $C_{1-5}$ alkyl, $C_{3-6}$ cycloalkyl, and phenyl;

$R^9$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{9a}R^{9a'}$, $(CHR')_rOH$, $(CHR')_rO(CHR')_rR^{9d}$, $(CHR')_rSH$, $(CHR')_rC(O)H$, $(CHR')_rS(CHR')_rR^{9d}$, $(CHR')_rC(O)OH$, $(CHR')_rC(O)(CHR')_rR^{9b}$, $(CHR')_rC(O)NR^{9a}R^{9a'}$, $(CHR')_rNR^{9f}C(O)$ $(CHR')_rR^{9b}$, $(CHR')_rC(O)O(CHR')_rR^{9d}$, $(CHR')_rOC(O)(CHR')_rR^{9b}$, $(CHR')_rC(=NR^{9f})NR^{9a}R^{9a'}$, $(CHR')_rNHC(=NR^{9f})NR^{9f}R^{9f}$, $(CHR')_rS(O)_p(CHR')_rR^{9b}$, $(CHR')_rS(O)_2NR^{9a}R^{9a'}$, $(CHR')_rNR^{9f}S(O)_2(CHR')_rR^{9b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{9e}$, and a $(CH_2)_r$-5–10 membered heterocyclic system containing 1–4 heteroatoms selected from N, O, and S, substituted with 0–2 $R^{9e}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–2 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{9e}$, and $(CH_2)_r$-5–6 membered heterocyclic system containing 1–4 heteroatoms selected from N, O, and S, substituted with 0–2 $R^{9e}$;

$R^{9d}$, at each occurrence, is selected from $C_{2-8}$ alkenyl, $C_{2-8}$ alkynyl, $C_{1-6}$ alkyl substituted with 0–3 $R^{9e}$, a $(CH_2)_r$—$C_{3-10}$ carbocyclic residue substituted with 0–3 $R^{9e}$, and a $(CH_2)_r$5–6 membered heterocyclic system containing 1–4 heteroatoms selected from N, O, and S, substituted with 0–3 $R^{9e}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-5}$ alkyl, $C_{3-6}$ cycloalkyl, and phenyl;

$R^{10}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{10a}R^{10a'}$, $(CHR')_rOH$, $(CHR')_rO(CHR')_rR^{10d}$, $(CHR')_rSH$, $(CHR')_rC(O)H$, $(CHR')_rS(CHR')_rR^{10d}$, $(CHR')_rC(O)OH$, $(CHR')_rC(O)(CHR')_rR^{10b}$, $(CHR')_rC(O)NR^{10a}R^{10a'}$, $(CHR')_rNR^{10f}C(O)(CHR')_rR^{10b}$, $(CHR')_rC(O)O(CHR')_rR^{10d}$, $(CHR')_rOC(O)(CHR')_rR^{10b}$, $(CHR')_rC(=NR^{10f})NR^{10a}R^{10a'}$, $(CHR')_rNHC(=NR^{10f})NR^{10f}R^{10f}$, $(CHR')_rS(O)_p(CHR')_rR^{10b}$, $(CHR')_rS(O)_2NR^{10a}R^{10a'}$, $(CHR')_rNR^{10f}S(O)_2(CHR')_rR^{10b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{10e}$;

$R^{10a}$ and $R^{10a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–2 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{10e}$, and $(CH_2)_r$-5–6 membered heterocyclic system containing 1–4 heteroatoms selected from N, O, and S, substituted with 0–2 $R^{10e}$;

$R^{10d}$, at each occurrence, is selected from $C_{2-8}$ alkenyl, $C_{2-8}$ alkynyl, $C_{1-6}$ alkyl substituted with 0–3 $R^{10e}$, a $(CH_2)_r$—$C_{3-10}$ carbocyclic residue substituted with 0–3 $R^{10e}$, and a $(CH_2)_r$5–6 membered heterocyclic system containing 1–4 heteroatoms selected from N, O, and S, substituted with 0–3 $R^{10e}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$phenyl;

$R^{10f}$, at each occurrence, is selected from H, $C_{1-5}$ alkyl, $C_{3-6}$ cycloalkyl, and phenyl;

$R^{11}$, at each occurrence is selected from H, $C_{1-8}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^{11a}$;

$R^{11a}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11b}R^{11b}$, $(CH_2)_rOH$, $(CH_2)_rOR^{11c}$, $(CH_2)_rSH$, $(CH_2)_rSR^{11c}$, $(CH_2)_rC(O)R^{11b}$, $(CH_2)_rC(O) NR^{11b}R^{11b}$, $(CH_2)_rNR^{11b}C(O)R^{11b}$, $(CH_2)_rC(O)OR^{11b}$, $(CH_2)_rOC(O)R^{11c}$, $(CH_2)_rCH(=NR^{11b})NR^{11b}R^{11b}$, $(CH_2)_rNHC(=NR^{11b})NR^{11b}R^{11b}$, $(CH_2)_rS(O)_pR^{11c}$, $(CH_2)_rS(O)_2NR^{11b}R^{11b}$, $(CH_2)_rNR^{11b}S(O)_2R^{11c}$, and $(CH_2)_r$phenyl;

$R^{11b}$, at each occurrence, is selected from H, $C_{1-6}$ alkyl, $C_{3-6}$ cycloalkyl, and phenyl;

$R^{11c}$, at each occurrence, is selected from $C_{1-5}$ alkyl, $C_{3-6}$ cycloalkyl, and phenyl;

$R^{12a}$ and $R^{12a'}$, at each occurrence, are selected from H, $C_{1-6}$ alkyl substituted with 0–3 $R^{12e}$, $C_{2-8}$ alkenyl, $C_{2-8}$ alkynyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–2 $R^{12e}$;

$R^{12b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{12e}$, and $(CH_2)_r$-5–6 membered heterocyclic system containing 1–4 heteroatoms selected from N, O, and S, substituted with 0–2 $R^{12e}$;

$R^{12}c$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{12f}R^{12f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{12b}$, $(CH_2)_rC(O)NR^{12f}R^{12f}$, $(CH_2)_rNR^{12f}C(O)R^{12a}$, $(CH_2)_rC(O)OC_{1-4}$ alkyl, $(CH_2)_rOC(O)R^{12b}$, $(CH_2)_rC(=NR^{12f})NR^{12f}R^{12f}$, $(CH_2)_rS(O)_pR^{12b}$, $(CH_2)_rNHC(=NR^{12f})NR^{12f}R^{12f}$, $(CH_2)_rS(O)_2NR^{12f}R^{12f}$, $(CH_2)_rNR^{12f}S(O)_2R^{12b}$, and $(CH_2)_r$-phenyl substituted with 0–3 $R^{12e}$;

$R^{12d}$, at each occurrence, is selected from $C_{2-8}$ alkenyl, $C_{2-8}$ alkynyl, $C_{1-6}$ alkyl substituted with 0–3 $R^{12e}$, a $(CH_2)_r$—$C_{3-10}$ carbocyclic residue substituted with 0–3 $R^{12e}$, and a $(CH_2)_r$5–6 membered heterocyclic system containing 1–4 heteroatoms selected from N, O, and S, substituted with 0–3 $R^{12e}$;

$R^{12e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-5}$ alkyl, $C_{3-6}$ cycloalkyl, and phenyl;

w is selected from 2, 3, 4, and 5;
v is selected from 0, 1 and 2;
t is selected from 0, 1 and 2;
r is selected from 0, 1, 2, 3, 4, and 5;
q is selected from 1, 2, 3, 4, and 5; and
p is selected from 1, 2, and 3.

In certain embodiments, the present invention provides compound novel compounds of formula I, wherein:

$R^3$ is selected from H, $C_{1-6}$ alkyl, $C_{2-8}$ alkenyl, and $C_{2-8}$ alkynyl;

$R^4$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0–3 $R^{4c}$;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $CF_3$, $(CH_2)_rOC_{1-5}$ alkyl, $(CH_2)_rOH$;

$R^6$, at each occurrence, is selected from H, $C_{1-4}$ alkyl, $(CH_2)_rC_{3-6}$ cycloalkyl, $(CF_2)_rCF_3$, $(CH_2)_rOH$, $(CH_2)_rOR^{6b}$, and $(CH_2)_r$phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

q is selected from 1, 2, and 3;
r is selected from 0, 1, 2, and 3; and
v is selected from 0, and 1.

In certain embodiments, the present invention provides novel compounds of formula I, wherein:

$R^2$, at each occurrence, is selected from H, $C_{1-8}$ alkyl, $(CH_2)_rC(O)R^{12b}$, $(CH_2)_rC(O)NR^{12a}R^{12a'}$, $(CH_2)_rC(O)OR^{12d}$, $(CH_2)_rS(O)_pR^{12b}$, $(CH_2)_rS(O)_2NR^{12a}R^{12a'}$, $(CR^{2'}R^{2''})_wNR^{12a}C(NR^a)NR^{12a}R^{12a'}$, $(CR^{2'}R^{2''})_rC(NR^a)$ $NR^{12a}R^{12a'}$, $(CR^{2'}R^{2'})_rC(NR^a)R^{12b}$, a $(CH_2)_r$-carbocyclic residue substituted with 0–3 $R^{12c}$, wherein the carbocyclic residue is selected from:

phenyl, $C_{3-6}$ cycloalkyl, napthyl, and adamantyl; and a $(CH_2)_r$-5–6 membered heterocyclic system substituted with 0–2 $R^{12c}$, wherein the heterocyclic system is selected from:

pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoidolyl, piperidinyl, pyrrazolyl, 1,2,4-triazolyl, 1,2,3-triazolyl, tetrazolyl, thiazolyl, oxazolyl, pyrazinyl, and pyrimidinyl;

alternatively, $R^2$ is an amino acid residue;

$R^7$, at each occurrence, is selected from $C_{1-8}$ alkyl, $C_{2-8}$ alkenyl, $C_{2-8}$ alkynyl, F, Cl, Br, I, $(CH_2)_rOH$, $(CH_2)_rOR^{7d}$, $(CH_2)_rNR^{7a}R^{7a'}$, $(CH_2)_rC_{3-6}$ cycloalkyl, and $(CH_2)_r$-phenyl substituted with 0–3 $R^{7e}$;

$R^{7a}$ and $R^{7a'}$, at each occurrence, are selected from H, $C_{1-6}$ alkyl;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7e}$ is selected from H and $C_{1-6}$ alkyl; $R^{7'}$ is H;

$R^{11}$, at each occurrence is selected from H, and $C_{1-8}$ alkyl;

$R^{12a}$ and $R^{12a'}$, at each occurrence, are selected from H, $C_{1-6}$ alkyl, and phenyl with 0–3 $R^{12e}$;

$R^{12b}$, at each occurrence, is selected from $C_{1-6}$ alkyl, $C_{3-6}$ cycloalkyl, and phenyl substituted with 0–3 $R^{12e}$; $R^{12c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{12f}R^{12f}$, $(CH_2)_rOH$, $(CH_2)_rOC_{1-4}$ alkyl, $(CH_2)_rC(O)R^{12b}$, $(CH_2)_rC(O)NR^{12f}R^{2f}$, $(CH_2)_rNR^{12f}C(O)R^{12a}$, $(CH_2)_rS(O)_2NR^{12f}R^{12f}$, $(CH_2)_rNR^{12f}S(O)_2R^{12b}$, and $(CH_2)_r$phenyl substituted with 0–3 $R^{12e}$;

$R^{12e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, $(CH_2)_rNR^{12f}R^{12f}$, and $(CH_2)_r$phenyl; and $R^{12f}$, at each occurrence, is selected from H, $C_{1-5}$ alkyl, $C_{3-6}$ cycloalkyl, and phenyl.

In certain embodiments, the present invention provides compounds of formula I, wherein:

A is selected from phenyl, cyclohexyl, cyclopentyl, and cyclopropyl;

$R^1$ is selected from a $(CR^1H)_r$-carbocyclic residue substituted with 0–5 $R^9$, wherein the carbocyclic residue is selected from phenyl, $C_{3-6}$ cycloalkyl, napthyl, and adamantyl; and a $(CR^1H)_r$-heterocyclic system substituted with 0–3 $R^9$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^5$ is selected from $(CR^5H)t$-phenyl substituted with 0–5 $R^{10}$; and a $(CR^5H)t$-heterocyclic system substituted with 0–3 $R^{10}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

In certain embodiments, the present invention provides compounds of formula I, wherein:

X is selected from $C_{1-5}$ alkylene substituted with 0–5 $R^7$, $C_{2-10}$, $C_{2-6}$ alkynylene substituted with 0–5 $R^7$, and $(CR^7R^7)_r$—A—$(CR^7R^7)_t$ substituted with 0–4 $R^8$; and Y is selected from NHC(=O)NH, NHC(=S)NH, NHC(=NR$^a$)NH, NHC(=CHCN)NH, NHC(=CHNO$_2$)NH, NHC(=C(CN)$_2$)NH, C(O)NH, and NHC(O).

In certain embodiments, the present invention provides compounds of formula I-i:

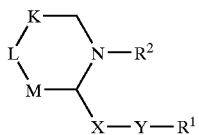

wherein:

$R^8$, at each occurrence, is selected from $C_{1-8}$ alkyl, $(CH_2)_rC_{3-6}$ cycloalkyl, $CF_3$, Cl, Br, I, F, $(CH_2)_rNR^{8a}R^{8a'}$, $NO_2$, CN, OH, $(CH_2)_rOR^{8d}$, $(CH_2)_rC(O)R^{8b}$, $(CH_2)_rC(O)NR^{8a}R^{8a'}$, $(CH_2)_rNR^{8f}C(O)R^{8b}$, $(CH_2)_rS(O)_pR^{8b}$, $(CH_2)_rS(O)_2NR^{8a}R^{8a'}$, $(CH_2)_rNR^{8f}S(O)_2R^{8b}$, and $(CH_2)_r$phenyl substituted with 0–3 $R^{8e}$;

$R^{8a}$ and $R^{8a'}$, at each occurrence, are selected from H, $C_{1-6}$ alkyl, $C_{3-6}$ cycloalkyl, and $(CH_2)_r$phenyl substituted with 0–3 $R^{8e}$;

$R^{8b}$, at each occurrence, is selected from H, $C_{1-6}$ alkyl, $C_{3-6}$ cycloalkyl, and $(CH_2)_r$phenyl substituted with 0–3 $R^{8e}$;

$R^{8d}$, at each occurrence, is selected from $C_{1-6}$ alkyl and phenyl;

$R^{8e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{8f}$, at each occurrence, is selected from H, and $C_{1-5}$ alkyl.

$R^{10}$, at each occurrence, is selected from $C_{1-8}$ alkyl, $(CH_2)_rC_{3-6}$ cycloalkyl, $CF_3$, Cl, Br, I, F, $(CH_2)_rNR^{10a}R^{10a'}$, $NO_2$, CN, OH, $(CH_2)_rOR^{10d}$, $(CH_2)_rC(O)R^{10b}$, $(CH_2)_rC(O)NR^{10a}R^{10a'}$, $(CH_2)_rNR^{10f}C(O)R^{10b}$, $(CH_2)_rS(O)_pR^{10b}$, $(CH_2)_rS(O)_2NR^{10a}R^{10a'}$, $(CH_2)_rNR^{10f}S(O)_2R^{10b}$, and $(CH_2)_r$phenyl substituted with 0–3 $R^{10e}$;

$R^{10a}$ and $R^{10a'}$, at each occurrence, are selected from H, $C_{1-6}$ alkyl, $C_{3-6}$ cycloalkyl, and $(CH_2)_r$phenyl substituted with 0–3 $R^{10e}$;

$R^{10b}$, at each occurrence, is selected from H, $C_{1-6}$ alkyl, $C_{3-6}$ cycloalkyl, and $(CH_2)_r$phenyl substituted with 0–3 $R^{10e}$;

$R^{10d}$, at each occurrence, is selected from $C_{1-6}$ alkyl and phenyl;

$R^{10e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{10f}$, at each occurrence, is selected from H, and $C_{1-5}$ alkyl.

In certain embodiments of formula I-i, the present invention provides novel compounds, wherein:

$R^5$ is $CH_2$phenyl substituted with 0–3 $R^{10}$;

K is selected from $CH_2$ and $CHR^5$;

L is selected from $CH_2$ and $CHR^5$;

M is selected from $CH_2$ and $CHR^5$;

$R^9$, at each occurrence, is selected from $C_{1-8}$ alkyl, $(CH_2)_rC_{3-6}$ cycloalkyl, $CF_3$, Cl, Br, I, F, $(CH_2)_rNR^{9a}R^{9a'}$, $NO_2$, CN, OH, $(CH_2)_rOR^{9d}$, $(CH_2)_rC(O)R^{9b}$, $(CH_2)_rC(O)NR^{9a}R^{9a'}$, $(CH_2)_rNR^{9f}C(O)R^{9b}$, $(CH_2)_rS(O)_pR^{9b}$, $(CH_2)_rS(O)_2NR^{9a}R^{9a'}$, $(CH_2)_rNR^{9f}S(O)_2R^{9b}$, $(CH_2)_r$phenyl substituted with 0–3 $R^{9e}$, and a $(CH_2)_r$-5–6 membered heterocyclic system containing 1–4 heteroatoms selected from N, O, and S, substituted with 0–2 $R^{9e}$;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9b}$, at each occurrence, is selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{9f}$, at each occurrence, is selected from H, and $C_{1-5}$ alkyl.

In certain embodiments of formula I-i, the present invention provides novel compounds, wherein:

X is $C_{1-4}$ alkylene selected from methylene, ethylene, propylene, and butylene; wherein $C_{1-4}$ alkylene is substituted with 0–2 $R^7$;

$R^7$, at each occurrence, is selected from $C_{1-3}$ alkyl, $(CH_2)_rOH$, $(CH_2)_rOR^{7d}$, $(CH_2)_rC_{3-6}$ cycloalkyl, and $(CH_2)_r$phenyl substituted with 0–3 $R^{7e}$;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, Cl, F, Br, I, CN, $NO_2$, $(CF_2)_rCF_3$, $(CH_2)_rOC_{1-5}$ alkyl, OH, $(CH_2)_rNR^{7f}R^{7f}$;

$R^{7f}$ is selected from H and $C_{1-6}$ alkyl; and

Y is selected from NHC(=O)NH, NHC(=NR$^a$)NH, NHC(=CHCN)NH, C(O)NH, and NHC(O).

In certain embodiments, the present invention provides novel compounds of formula I-ii:

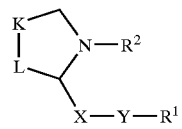

wherein:

$R^8$, at each occurrence, is selected from $C_{1-8}$ alkyl, $(CH_2)_rC_{3-6}$ cycloalkyl, $CF_3$, Cl, Br, I, F, $(CH_2)_rNR^{8a}R^{8a'}$, $NO_2$, CN, OH, $(CH_2)_rOR^{8d}$, $(CH_2)_rC(O)R^{8b}$, $(CH_2)_rC(O)NR^{8a}R^{8a'}$, $(CH_2)_rNR^{8f}C(O)R^{8b}$, $(CH_2)_rS(O)_pR^{8b}$, $(CH_2)_rS(O)_2NR^{8a}R^{8a'}$, $(CH_2)_rNR^{8f}S(O)_2R^{8b}$, and $(CH_2)_r$phenyl substituted with 0–3 $R^{8e}$;

$R^{8a}$ and $R^{8a'}$, at each occurrence, are selected from H, $C_{1-6}$ alkyl, $C_{3-6}$ cycloalkyl, and $(CH_2)_r$phenyl substituted with 0–3 $R^{8e}$;

$R^{8b}$, at each occurrence, is selected from H, $C_{1-6}$ alkyl, $C_{3-6}$ cycloalkyl, and $(CH_2)_r$phenyl substituted with 0–3 $R^{8e}$;

$R^{8d}$, at each occurrence, is selected from $C_{1-6}$ alkyl and phenyl;

$R^{8e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{8f}$, at each occurrence, is selected from H, and $C_{1-5}$ alkyl.

$R^{10}$, at each occurrence, is selected from $C_{1-8}$ alkyl, $(CH_2)_rC_{3-6}$ cycloalkyl, $CF_3$, Cl, Br, I, F, $(CH_2)_rNR^{10a}R^{10a'}$, $NO_2$, CN, OH, $(CH_2)_rOR^{10d}$, $(CH_2)_rC(O)R^{10b}$, $(CH_2)_rC(O)NR^{10a}R^{10a'}$, $(CH_2)_rNR^{10f}C(O)R^{10b}$, $(CH_2)_rS(O)_pR^{10b}$, $(CH_2)_rS(O)_2NR^{10a}R^{10a'}$, $(CH_2)_rNR^{10f}S(O)_2R^{10b}$, and $(CH_2)_r$phenyl substituted with 0–3 $R^{10e}$;

$R^{10a}$ and $R^{10a'}$, at each occurrence, are selected from H, $C_{1-6}$ alkyl, $C_{3-6}$ cycloalkyl, and $(CH_2)_r$phenyl substituted with 0–3 $R^{10e}$;

$R^{10b}$, at each occurrence, is selected from H, $C_{1-6}$ alkyl, $C_{3-6}$ cycloalkyl, and $(CH_2)_r$phenyl substituted with 0–3 $R^{10e}$;

$R^{10d}$, at each occurrence, is selected from $C_{1-6}$ alkyl and phenyl;

$R^{10e}$, at each occurrence, is selected from $C_{1-6}$ alkyl, Cl, F, Br, I, CN, NO$_2$, (CF$_2$)$_r$CF$_3$, OH, and (CH$_2$)$_r$OC$_{1-5}$ alkyl; and $R^{10f}$, at each occurrence, is selected from H, and $C_{1-5}$ alkyl.

In certain embodiments of formula I-ii, the present invention provides novel compounds, wherein:

$R^5$ is CH$_2$phenyl substituted with 0–3 $R^{10}$;

K is selected from CH$_2$ and CHR$^5$;

L is selected from CH$_2$ and CHR$^5$;

$R^9$, at each occurrence, is selected from $C_{1-8}$ alkyl, (CH$_2$)$_r$C$_{3-6}$ cycloalkyl, CF$_3$, Cl, Br, I, F, (CH$_2$)$_r$NR$^{9a}$R$^{9a'}$, NO$_2$, CN, OH, (CH$_2$)$_r$OR$^{9d}$, (CH$_2$)$_r$C(O)R$^{9b}$, (CH$_2$)$_r$C(O)NR$^{9a}$R$^{9a'}$, (CH$_2$)$_r$NR$^{9f}$C(O)R$^{9b}$, (CH$_2$)$_r$S(O)$_p$R$^{9b}$, (CH$_2$)$_r$S(O)$_2$NR$^{9a}$R$^{9a'}$, (CH$_2$)$_r$NR$^{9f}$S(O)$_2$R$^{9b}$, (CH$_2$)$_r$phenyl substituted with 0–3 R$^{9e}$, and a (CH$_2$)$_r$-5–6 membered heterocyclic system containing 1–4 heteroatoms selected from N, O, and S, substituted with 0–2 R$^{9e}$;

$R^{9a}$ and $R^{9a'}$, at each occurrence, are selected from H, $C_{1-6}$ alkyl, $C_{3-6}$ cycloalkyl, and (CH$_2$)$_r$phenyl substituted with 0–3 R$^{9e}$;

$R^{9b}$, at each occurrence, is selected from H, $C_{1-6}$ alkyl, $C_{3-6}$ cycloalkyl, and (CH$_2$)$_r$phenyl substituted with 0–3 R$^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, NO$_2$, (CF$_2$)$_r$CF$_3$, OH, and (CH$_2$)$_r$OC$_{1-5}$ alkyl; and $R^{9f}$, at each occurrence, is selected from H, and $C_{1-5}$ alkyl.

In certain embodiments of formula I-ii, the present invention provides novel compounds, wherein:

X is $C_{1-4}$ alkylene selected from methylene, ethylene, propylene, and butylene; wherein $C_{1-4}$ alkylene is substituted with 0–2 R$^7$;

$R^7$, at each occurrence, is selected from $C_{1-3}$ alkyl, (CH$_2$)$_r$OH, (CH$_2$)$_r$OR$^{7d}$, (CH$_2$)$_r$C$_{3-6}$ cycloalkyl, and (CH$_2$)$_r$phenyl substituted with 0–3 R$^{7e}$;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, Cl, F, Br, I, CN, NO$_2$, (CF$_2$)$_r$CF$_3$, (CH$_2$)$_r$OC$_{1-5}$ alkyl, OH, (CH$_2$)$_r$NR$^{7f}$R$^{7f}$;

$R^{7f}$ is selected from H and $C_{1-6}$ alkyl; and

Y is selected from NHC(=O)NH, NHC(=NR$^a$)NH, NHC(=CHCN)NH, C(O)NH, and NHC(O).

In certain embodiments, the present invention provides novel compounds of formula I, wherein:

when v is 0, L is CH$_2$;
when v is 1, M is CH$_2$; or
when v is 2, the M adjacent to the carbon bearing R$^3$ is CH$_2$.

In certain embodiments, the present invention provides novel compounds of formula I, wherein:

A is selected from phenyl, cyclohexyl, cyclopentyl, and cyclopropyl;

$R^7$, at each occurrence, is selected from $C_{1-8}$ alkyl, $C_{2-8}$ alkenyl, $C_{2-8}$ alkynyl, F, Cl, Br, I, (CH$_2$)$_r$OH, (CH$_2$)$_r$OR$^{7d}$, (CH$_2$)$_r$NR$^{7a}$R$^{7a'}$, (CH$_2$)$_r$C$_{3-6}$ cycloalkyl, and (CH$_2$)$_r$phenyl substituted with 0–3 R$^{7e}$;

$R^{7a}$ and $R^{7a'}$, at each occurrence, are selected from H, $C_{1-6}$ alkyl;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

$R^{7e}$ is selected from H and $C_{1-6}$ alkyl;

$R^{7f}$ is H;

$R^8$, at each occurrence, is selected from $C_{1-8}$ alkyl, (CH$_2$)$_r$C$_{3-6}$ cycloalkyl, CF$_3$, Cl, Br, I, F, (CH$_2$)$_r$NR$^{8a}$R$^{8a'}$, NO$_2$, CN, OH, (CH$_2$)$_r$OR$^{8d}$, (CH$_2$)$_r$C(O)R$^{8b}$, (CH$_2$)$_r$C(O)NR$^{8a}$R$^{8a'}$, (CH$_2$)$_r$NR$^{8f}$C(O)R$^{8b}$, (CH$_2$)$_r$S(O)$_p$R$^{8b}$, (CH$_2$)$_r$S(O)$_2$NR$^{8a}$R$^{8a'}$, (CH$_2$)$_r$NR$^{8f}$S(O)$_2$R$^{8b}$, and (CH$_2$)$_r$phenyl substituted with 0–3 R$^{8e}$;

$R^{8a}$ and $R^{8a'}$, at each occurrence, are selected from H, $C_{1-6}$ alkyl, $C_{3-6}$ cycloalkyl, and (CH$_2$)$_r$phenyl substituted with 0–3 R$^{8e}$;

$R^{8b}$, at each occurrence, is selected from H, $C_{1-6}$ alkyl, $C_{3-6}$ cycloalkyl, and (CH$_2$)$_r$phenyl substituted with 0–3 R$^{8e}$;

$R^{8d}$, at each occurrence, is selected from $C_{1-6}$ alkyl and phenyl;

$R^{8e}$, at each occurrence, is selected from $C_{1-6}$ alkyl, Cl, F, Br, I, CN, NO$_2$, (CF$_2$)$_r$CF$_3$, OH, and (CH$_2$)$_r$OC$_{1-5}$ alkyl; and $R^{8f}$, at each occurrence, is selected from H and $C_{1-5}$ alkyl; and $R^{11}$, at each occurrence, is selected from H, and $C_{1-8}$ alkyl.

In certain embodiments, the present invention provides novel compounds of formula I, wherein:

$R^1$ is selected from a carbocyclic residue substituted with 0–3 R$^9$, wherein the carbocyclic residue is selected from phenyl and $C_{3-6}$ cycloalkyl; and a heterocyclic system substituted with 0–3 R$^9$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

In certain embodiments, the present invention provides novel compounds of formula I, wherein:

$R^5$ is selected from (CR$^{5'}$H)$_r$-phenyl substituted with 0–3 R$^{10}$; and a (CR$^{5'}$H)$_r$-heterocyclic system substituted with 0–3 R$^{10}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

In certain embodiments, the present invention provides novel compounds of formula I, wherein v is 1, M is CH$_2$, and J is CH$_2$.

In certain embodiments, the present invention provides novel compounds of formula I, wherein R$^3$ is H and R$^4$ is absent.

In certain embodiments, the present invention provides novel compounds of formula I, wherein:

$R^9$, at each occurrence, is selected from $C_{1-8}$ alkyl, (CH$_2$)$_r$C$_{3-6}$ cycloalkyl, CF$_3$, Cl, Br, I, F, (CH$_2$)$_r$NR$^{9a}$R$^{9a'}$, NO$_2$, CN, OH, (CH$_2$)$_r$OR$^{9d}$, (CH$_2$)$_r$C(O)R$^{9b}$, (CH$_2$)$_r$C(O)NR$^{9a}$R$^{9a'}$, (CH$_2$)$_r$NR$^{9f}$C(O)R$^{9b}$, (CH$_2$)$_r$S(O)$_p$R$^{9b}$, (CH$_2$)$_r$S(O)$_2$NR$^{9a}$R$^{9a'}$, (CH$_2$)$_r$NR$^{9f}$S(O)$_2$R$^{9b}$, (CH$_2$)$_r$phenyl substituted with 0–3 R$^{9e}$, and a (CH$_2$)$_r$-5–6 membered heterocyclic system containing 1–4 heteroatoms selected from N, O, and S, substituted with 0–2 R$^{9e}$;

$R^{9a}$ and $R^{9a'}$, at each occurrence, are selected from H, $C_{1-6}$ alkyl, $C_{3-6}$ cycloalkyl, and (CH$_2$)$_r$phenyl substituted with 0–3 R$^{9e}$;

$R^{9b}$, at each occurrence, is selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{9f}$, at each occurrence, is selected from H, and $C_{1-5}$ alkyl;

$R^{10}$, at each occurrence, is selected from $C_{1-8}$ alkyl, $(CH_2)_rC_{3-6}$ cycloalkyl, $CF_3$, Cl, Br, I, F, $(CH_2)_rNR^{10a}R^{10a'}$, $NO_2$, CN, OH, $(CH_2)_rOR^{10d}$, $(CH_2)_rC(O)R^{10b}$, $(CH_2)_rC(O)NR^{10a}R^{10a'}$, $(CH_2)_rNR^{10f}C(O)R^{10b}$, $(CH_2)_rS(O)_pR^{10b}$, $(CH_2)_rS(O)_2NR^{10a}R^{10a'}$, $(CH_2)_rNR^{10f}S(O)_2R^{10b}$, and $(CH_2)_r$phenyl substituted with 0–3 $R^{10e}$;

$R^{10a}$ and $R^{10a'}$, at each occurrence, are selected from H, $C_{1-6}$ alkyl, $C_{3-6}$ cycloalkyl, and $(CH_2)_r$phenyl substituted with 0–3 $R^{10e}$;

$R^{10b}$, at each occurrence, is selected from H, $C_{1-6}$ alkyl, $C_{3-6}$ cycloalkyl, and $(CH_2)_r$phenyl substituted with 0–3 $R^{10e}$;

$R^{10d}$, at each occurrence, is selected from $C_{1-6}$ alkyl and phenyl;

$R^{10e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{10f}$, at each occurrence, is selected from H, and $C_{1-5}$ alkyl.

In certain preferred embodiments, the present invention provides novel compounds of formula I, wherein K is $CH_2$, L is $CHR^5$, wherein $R^5$ is substituted with 0–3 $R^{10}$.

In certain embodiments, the present invention provides novel compounds of formula I, wherein $R^5$ is a benzyl group ($CH_2$-phenyl) substituted with 0–3 $R^{10}$.

In certain embodiments, the present invention provides novel compounds of formula I, wherein $R^1$ is phenyl substituted with 0–3 $R^9$.

In certain embodiments, the present invention provides novel compounds of formula I, wherein X is propylene substituted with 0–3 $R^7$.

In a certain embodiments, the present invention provides novel compounds of formula I, wherein:

$R^7$, at each occurrence, is selected from $C_{1-3}$ alkyl, $(CH_2)_rOH$, $(CH_2)_rOR^{7d}$, $(CH_2)_rC_{3-6}$ cycloalkyl, and $(CH_2)_r$-phenyl substituted with 0–3 $R^{7e}$;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, Cl, F, Br, I, CN, $NO_2$, $(CF_2)_rCF_3$, $(CH_2)_rOC_{1-5}$ alkyl, OH, $(CH_2)_rNR^{7f}R^{7f}$; and $R^{7f}$ is selected from H and $C_{1-6}$ alkyl.

In certain embodiments, the present invention provides novel compounds of formula I, wherein:

$R^2$, at each occurrence, is selected from H, $C_{1-8}$ alkyl, $(CR^{2'}R^{2''})_qNR^{12a}R^{12a'}$, $(CR^{2'}R^{2''})_wOH$, $(CR^{2'}R^{2''})_wO(CR^{2'}R^{2''})_rR^{12d}$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a''}$, $(CR^{2'}R^{2''})_rC(O)NR^{12a}R^{12a'}$, $(CR^{2'}R^{2''})_qNR^{12f}C(O)(CR^{2'}R^{2''})_rR^{12b}$, $(CR^{2'}R^{2''})_wS(O)_2NR^{12a}R^{12a'}$, $(CR^{2'}R^{2''})_qNR^{12f}S(O)_2(CR^{2'}R^{2''})_rR^{12b}$, $C_{1-6}$ haloalkyl, $C_{2-8}$ alkenyl substituted with 0–3 $R^{12c}$, $C_{2-8}$ alkynyl substituted with 0–3 $R^{12c}$, a $(CR^{2'}R^{2''})_r$—$C_{3-10}$ carbocyclic residue substituted with 0–3 $R^{12c}$, and a $(CH_2)_r$-5–10 membered heterocyclic system containing 1–4 heteroatoms selected from N, O, and S, substituted with 0–2 $R^{12c}$;

alternatively, $R^2$ is an amino acid residue; and $R^{2'}$ and $R^{2''}$, at each occurrence, are selected from H, $C_{1-8}$ alkyl, $C_{2-8}$ alkenyl, $(CH_2)_rOH$, $(CH_2)_rOR^{2b}$, $(CH_2)_rC(O)R^{2b}$, $(CH_2)_rC(O)NR^{2a}R^{2a'}$, $(CH_2)_rNR^{2d}C(O)R^{2a}$.

In certain embodiments, the present invention provides novel compounds of formula I, wherein:

$R^2$, at each occurrence, is selected from H, $C_{1-8}$ alkyl, $(CH_2)_qNR^{12a}R^{12a'}$, $(CH_2)_wOH$, $(CH)_wO(CR^{2'}R^{2''})_rR^{12d}$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a'}$, $(CR^{2'}R^{2''})_rC(O)NR^{12a}R^{12a'}$, $(CR^{2'}R^{2''})_qNR^{12f}C(O)(CR^{2'}R^{2''})_rR^{12b}$, $(CR^{2'}R^{2''})_wS(O)_2NR^{12a}R^{12a'}$, $(CR^{2'}R^{2''})_qNR^{12f}S(O)_2(CR^{2'}R^{2''})_rR^{12b}$;

$R^{2'}$ and $R^{2''}$ are H;

r is selected from 0, 1, and 2; and w and q are selected from 2 and 3.

In certain embodiments, the present invention provides novel compounds of formula I, wherein X is unsubstituted propylene.

In certain embodiments, the present invention provides novel compounds of formula I, wherein $R^5$ is substituted with 0–2 $R^{10}$.

In certain embodiments, the present invention provides novel compounds of formula I, wherein:

$R^{10}$, at each occurrence, is selected from $C_{1-8}$ alkyl, $(CH_2)_rC_{3-6}$ cycloalkyl, $CF_3$, Cl, Br, I, F, $C(O)C_{1-4}$ alkyl, $(CH_2)_rNR^{10a}R^{10a'}$, CN, OH, $OCF_3$, $(CH_2)_rOR^{10d}$;

$R^{10a}$ and $R^{10a'}$, at each occurrence, are selected from H, $C_{1-6}$ alkyl, and $C_{3-6}$ cycloalkyl; and $R^{10d}$ is $C_{1-6}$ alkyl.

In certain embodiments, the present invention provides novel compounds of formula I, wherein $R^{10}$ is selected from F, Cl, Br, $OCF_3$, and $CF_3$.

In certain embodiments, the present invention provides novel compounds of formula I, wherein $R^1$ is substituted with 0–2 $R^9$.

In certain embodiments, the present invention provides novel compounds of formula I, wherein:

$R^9$, at each occurrence, is selected from $C_{1-8}$ alkyl, $(CH_2)_rC_{3-6}$ cycloalkyl, Cl, Br, F, $NO_2$, CN, $(CHR')_rNR^{9a}R^{9a'}$, $(CHR')_rOH$, $(CHR')_rO(CHR')_rR^{9d}$, $(CHR')_rC(O)(CHR')_rR^{9b}$, $(CHR')_rC(O)NR^{9a}R^{9a'}$, $(CHR')_rNR^{9f}C(O)(CHR')_rR^{9b}$, $(CHR')_rC(O)O(CHR')_rR^{9d}$, $(CHR')_rS(O)_p(CHR')_rR^{9b}$, $(CHR')_rS(O)_2NR^{9a}R^{9a'}$, $(CHR')_rNR^{9f}S(O)_2(CHR')_rR^{9b}$, $CF_3$, $OCF_3$, $(CHR')_r$phenyl substituted with 0–3 $R^{9e}$, and a $(CH_2)_r$-5–10 membered heterocyclic system containing 1–4 heteroatoms selected from N, O, and S, substituted with 0–2 $R^{9e}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–2 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{9e}$, and $(CH_2)_r$-5–6 membered heterocyclic system containing 1–4 heteroatoms selected from N, O, and S, substituted with 0–2 $R^{9e}$;

$R^{9d}$, at each occurrence, is selected from $C_{2-8}$ alkenyl, $C_{2-8}$ alkynyl, $C_{1-6}$ alkyl substituted with 0–3 $R^{9e}$, a $(CH_2)_r$—$C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl; and $R^{9f}$, at each occurrence, is selected from H, $C_{1-5}$ alkyl, $C_{3-6}$ cycloalkyl, and phenyl.

In certain embodiments, the present invention provides novel compounds of formula I, wherein $R^1$ is phenyl substituted with $R^9$ groups which occupy the 3, or the 5, or both the 3 and 5 positions on the phenyl ring.

In certain embodiments, the present invention provides novel compounds of formula I, wherein $R^9$, at each occurrence, is selected from $C(O)R^{9b}$, $C(O)OR^d$, $C(O)OH$, CN, and a $(CH_2)_r$-5–6 membered heterocyclic system containing 1–4 heteroatoms selected from N, O, and S, substituted with 0–2 $R^{9e}$.

In certain embodiments, the present invention provides novel compounds of formula I, wherein Y is selected from $NR^{11}C(=S)NR^{11}$, $NR^{11}C(=NR^a)NR^{11}$, $NR^{11}C(=CHCN)NR^{11}$, $NR^{11}C(=CHNO_2)NR^{11}$, $NR^{11}C(=C(CN)_2)NR^{11}$, $NR^{11}$, $C(O)$, $S(O)_2NR^{11}$, $NR^{11}S(O)_2$, $NR^{11}S(O)_2NR^{11}$, $C(O)NR^{11}$, $NR^{11}C(O)$, $NR^{11}C(O)O$, $OC(O)NR^{11}$, and $S(O)_p$.

In certain embodiments, the present invention provides novel compounds of formula I, wherein Y is selected from $NR^{11}C(=NR^a)NR^{11}$, $NR^{11}C(=CHCN)NR^{11}$, $NR^{11}C(=CHNO_2)NR^{11}$, and $NR^{11}C(=C(CN)_2)NR^{11}$.

In certain embodiments, the present invention provides novel compounds of formula I, wherein Y is $NR^{11}C(=NCN)NR^{11}$.

In certain embodiments, the present invention provides novel compounds of formula I, wherein Y is $NR^{11}C(=C(CN)_2)NR^{11}$.

In certain embodiments, the present invention provides novel compounds of formula I, wherein Y is selected from $NR^{11}C(=C(CN)_2)NR^{11}$ and $NR^{11}C(=NCN)NR^{11}$, and $R^{11}$, at each occurrence, is selected from H and $C_{1-6}$ alkyl.

In certain embodiments, the present invention provides novel compounds of formula I, wherein $R^9$, at each occurrence, is selected from $C(O)R^{9b}$, $C(O)OR^d$, $C(O)OH$, CN, and a $(CH_2)_r$-5–6 membered heterocyclic system containing 1–4 heteroatoms selected from N, O, and S, substituted with 0–2 $R^{9e}$.

In certain embodiments, the present invention provides novel compounds of formula I, wherein:

X is $(CR^7R^7)_t—A—(CR^7R^7)_t$ substituted with 0–3 $R^8$;

$R^7$, at each occurrence, is selected from $C_{1-3}$ alkyl, $(CH_2)_rOH$, $(CH_2)_rOR^{7d}$, $(CH_2)_rC_{3-6}$ cycloalkyl, and $(CH_2)_r$-phenyl substituted with 0–3 $R^{7e}$;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, Cl, F, Br, I, CN, $NO_2$, $(CF_2)_rCF_3$, $(CH_2)_rOC_{1-5}$ alkyl, OH, $(CH_2)_rNR^{7f}R^{7f}$;

$R^{7f}$ is selected from H and $C_{1-6}$ alkyl;

$R^8$, at each occurrence, is selected from $C_{1-8}$ alkyl, $(CH_2)_rC_{3-6}$ cycloalkyl, $CF_3$, Cl, Br, I, F, $(CH_2)_rNR^{8f}R^{8f}$, $NO_2$, CN, OH, $(CH_2)_rOR^{8d}$, and $(CH_2)_r$phenyl substituted with 0–3 $R^{8e}$;

$R^{8d}$, at each occurrence, is selected from $C_{1-6}$ alkyl and phenyl;

$R^{8e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{8f}$, at each occurrence, is selected from H and $C_{1-5}$ alkyl.

In certain preferred embodiments, the present invention provides novel compounds of formula I, wherein the compound of formula I is selected from:

(+)-trans-N-(3-cyanophenyl)-N'-[3-[4-(phenylmethyl)-2-piperidinyl]propyl urea, (±)-trans-N-(3-cyanophenyl)-N'-[3-[4-(4-phenylmethyl)-1-methyl-2-piperidinyl]propyl urea, (±)-trans-N-(3-cyanophenyl)-N'-[3-[4-(4-phenylmethyl)-1-acetyl-2-piperidinyl]propyl urea, (±)-trans-N-phenyl-N'-[3-[4-(phenylmethyl)-2-piperidinyl]propyl urea, (±)-trans-N-(3-cyanophenyl)-N'-[3-[4-(phenylmethyl)-2-piperidinyl]propyl urea, (±)-trans-N-(3-acetylphenyl)-N'-[3-[4-(phenylmethyl)-2-piperidinyl]propyl urea, (±)-trans-N-(3-carbomethoxyphenyl)-N'-[3-[4-(phenylmethyl)-2-piperidinyl]propyl urea, (±)-trans-N-(3-carboethoxyphenyl)-N'-[3-[4-(phenylmethyl)-2-piperidinyl]propyl urea, (±)-trans-N-(3-fluorophenyl)-N'-[3-[4-(phenylmethyl)-2-piperidinyl]propyl urea, (±)-trans-N-(4-fluorophenyl)-N'-[3-[4-(phenylmethyl)-2-piperidinyl]propyl urea, (±)-trans-N-(3-chlorophenyl)-N'-[3-[4-(phenylmethyl)-2-piperidinyl]propyl urea, (±)-trans-N-(4-chlorophenyl)-N'-[3-[4-(phenylmethyl)-2-piperidinyl]propyl urea, (±)-trans-N-(3-methoxyphenyl)-N'-[3-[4-(phenylmethyl)-2-piperidinyl]propyl urea, (±)-trans-N-phenyl-N'-[3-[4-(4-fluorophenylmethyl)-2-piperidinyl]propyl urea, (±)-trans-N-(3-cyano-phenyl)-N'3-[3-[4-(4-fluorophenylmethyl)-2-piperidinyl]propyl urea, (±)-trans-N-(3-acetyl-phenyl)-N'-[3-[4-(4-fluorophenylmethyl)-2-piperidinyl]propyl urea, (±)-trans-N-(3-carbomethoxy-phenyl)-N'-[3-[4-(4-fluorophenylmethyl)-2-piperidinyl]propyl urea, (±)-trans-N-(3-carboethoxy-phenyl)-N'-[3-[4-(4-fluorophenylmethyl)-2-piperidinyl]propyl urea, (±)-trans-N-(3-fluoro-phenyl)-N'-[3-[4-(4-fluorophenylmethyl)-2-piperidinyl]propyl urea, (±)-trans-N-(4-fluoro-phenyl)-N'-[3-[4-(4-fluorophenylmethyl)-2-piperidinyl]propyl urea, (±)-trans-N-(3-chloro-phenyl)-N'-[3-[4-(4-fluorophenylmethyl)-2-piperidinyl]propyl urea, (±)-trans-N-(4-chloro-phenyl)-N'-[3-[4-(4-fluorophenylmethyl)-2-piperidinyl]propyl urea, (±)-trans-N-(3-methoxy-phenyl)-N'-[3-[4-(4-fluorophenylmethyl)-2-piperidinyl]propyl urea, (±)-trans-N-phenyl-N'-[2-[4-(phenylmethyl)-2-piperidinyl]ethyl urea, (±)-trans-N-(3-cyanophenyl)-N'-[2-[4-(phenylmethyl)-2-piperidinyl]ethyl urea, (±)-trans-N-(3-acetylphenyl)-N'-[2-[4-(phenylmethyl)-2-piperidinyl]ethyl urea, (±)-trans-N-(3-carbomethoxyphenyl)-N'-[2-[4-(phenylmethyl)-2-piperidinyl]ethyl urea, (±)-trans-N-(3-carboethoxyphenyl)-N'-[2-[4-(phenylmethyl)-2-piperidinyl]ethyl urea, (±)-trans-N-(3-fluorophenyl)-N'-[2-[4-(phenylmethyl)-2-piperidinyl]ethyl urea, (±)-trans-N-(4-fluorophenyl)-N'-[2-[4-(phenylmethyl)-2-piperidinyl]ethyl urea, (±)-trans-N-(3-chlorophenyl)-N'-[2-[4-(phenylmethyl)-2-piperidinyl]ethyl urea, (±)-trans-N-(4-chlorophenyl)-N'-[2-[4-(phenylmethyl)-2-piperidinyl]ethyl urea, (±)-trans-N-(3-methoxyphenyl)-N'-[2-[4-(phenylmethyl)-2-piperidinyl]ethyl urea,
(±)-trans-N-phenyl-N'-[2-[4-(4-fluorophenylmethyl)-2-piperidinyl]ethyl urea,
(±)-trans-N-(3-cyano-phenyl)-N'-[2-[4-(4-fluorophenylmethyl)-2-piperidinyl]ethyl urea,
(±)-trans-N-(3-acetyl-phenyl)-N'-[2-[4-(4-fluorophenylmethyl)-2-piperidinyl]ethyl urea,
(±)-trans-N-(3-carbomethoxy-phenyl)-N'-[2-[4-(4-fluorophenylmethyl)-2-piperidinyl]ethyl urea,
(±)-trans-N-(3-carboethoxy-phenyl)-N'-[2-[4-(4-fluorophenylmethyl)-2-piperidinyl]ethyl urea,
(±)-trans-N-(3-fluoro-phenyl)-N'-[2-[4-(4-fluorophenylmethyl)-2-piperidinyl]ethyl urea,
(±)-trans-N-(4-fluoro-phenyl)-N'-[2-[4-(4-fluorophenylmethyl)-2-piperidinyl]ethyl urea,
(±)-trans-N-(3-chloro-phenyl)-N'-[2-[4-(4-fluorophenylmethyl)-2-piperidinyl]ethyl urea,
(±)-trans-N-(4-chloro-phenyl)-N'-[2-[4-(4-fluorophenylmethyl)-2-piperidinyl]ethyl urea,
(±)-trans-N-(3-methoxy-phenyl)-N'-[2-[4-(4-fluorophenylmethyl)-2-piperidinyl]ethyl urea,
(±)-trans-N-phenyl-N'-[4-(phenylmethyl)-2-piperidinyl]methyl urea,
(±)-trans-N-(3-cyanophenyl)-N'-[4-(phenylmethyl)-2-piperidinyl]methyl urea,
(±)-trans-N-(3-acetylphenyl)-N'-[4-(phenylmethyl)-2-piperidinyl]methyl urea,
(±)-trans-N-(3-carbomethoxyphenyl)-N'-[4-(phenylmethyl)-2-piperidinyl]methyl urea,
(±)-trans-N-(3-carboethoxyphenyl)-N'-[4-(phenylmethyl)-2-piperidinyl]methyl urea,
(±)-trans-N-(3-fluorophenyl)-N'-[4-(phenylmethyl)-2-piperidinyl]methyl urea,
(±)-trans-N-(4-fluorophenyl)-N'-[4-(phenylmethyl)-2-piperidinyl]methyl urea,
(±)-trans-N-(3-chlorophenyl)-N'-[4-(phenylmethyl)-2-piperidinyl]methyl urea,
(±)-trans-N-(4-chlorophenyl)-N'-[4-(phenylmethyl)-2-piperidinyl]methyl urea,
(±)-trans-N-(3-methoxyphenyl)-N'-[4-(phenylmethyl)-2-piperidinyl]methyl urea,
(±)-trans-N-phenyl-N'-[4-(4-fluorophenylmethyl)-2-piperidinyl]methyl urea,
(±)-trans-N-(3-cyano-phenyl)-N'-[4-(4-fluorophenylmethyl)-2-piperidinyl]methyl urea,
(±)-trans-N-(3-acetyl-phenyl)-N'-[4-(4-fluorophenylmethyl)-2-piperidinyl]methyl urea,
(±)-trans-N-(3-carbomethoxy-phenyl)-N'-[4-(4-fluorophenylmethyl)-2-piperidinyl]methyl urea,
(±)-trans-N-(3-carboethoxy-phenyl)-N'-[4-(4-fluorophenylmethyl)-2-piperidinyl]methyl urea,
(±)-trans-N-(3-fluoro-phenyl)-N'-[4-(4-fluorophenylmethyl)-2-piperidinyl]methyl urea,
(±)-trans-N-(4-fluoro-phenyl)-N'-[4-(4-fluorophenylmethyl)-2-piperidinyl]methyl urea,
(±)-trans-N-(3-chloro-phenyl)-N'-[4-(4-fluorophenylmethyl)-2-piperidinyl]methyl urea,
(±)-trans-N-(4-chloro-phenyl)-N'-[4-(4-fluorophenylmethyl)-2-piperidinyl]methyl urea,
(±)-trans-N-(3-methoxy-phenyl)-N'-[4-(4-fluorophenylmethyl)-2-piperidinyl]methyl urea,
(±)-cis-N-phenyl-N'-[3-[4-(phenylmethyl)-2-piperidinyl]propyl urea,
(±)-cis-N-(3-cyanophenyl)-N'-[3-[4-(phenylmethyl)-2-piperidinyl]propyl urea,
(±)-cis-N-(3-acetylphenyl)-N'-[3-[4-(phenylmethyl)-2-piperidinyl]propyl urea,
(±)-cis-N-(3-carbomethoxyphenyl)-N'-[3-[4-(phenylmethyl)-2-piperidinyl]propyl urea,
(±)-cis-N-(3-carboethoxyphenyl)-N'-[3-[4-(phenylmethyl)-2-piperidinyl]propyl urea,
(±)-cis-N-(3-fluorophenyl)-N'-[3-[4-(phenylmethyl)-2-piperidinyl]propyl urea,
(±)-cis-N-(4-fluorophenyl)-N'-[3-[4-(phenylmethyl)-2-piperidinyl]propyl urea,
(±)-cis-N-(3-chlorophenyl)-N'-[3-[4-(phenylmethyl)-2-piperidinyl]propyl urea,
(±)-cis-N-(4-chlorophenyl)-N'-[3-[4-(phenylmethyl)-2-piperidinyl]propyl urea,
(±)-cis-N-(3-methoxyphenyl)-N'-[3-[4-(phenylmethyl)-2-piperidinyl]propyl urea,
(±)-cis-N-phenyl-N'-[3-[4-(4-fluorophenylmethyl)-2-piperidinyl]propyl urea,
(±)-cis-N-(3-cyano-phenyl)-N'-[3-[4-(4-fluorophenylmethyl)-2-piperidinyl]propyl urea,
(±)-cis-N-(3-acetyl-phenyl)-N'-[3-[4-(4-fluorophenylmethyl)-2-piperidinyl]propyl urea,
(±)-cis-N-(3-carbomethoxy-phenyl)-N'-[3-[4-(4-fluorophenylmethyl)-2-piperidinyl]propyl urea,
(±)-cis-N-(3-carboethoxy-phenyl)-N'-[3-[4-(4-fluorophenylmethyl)-2-piperidinyl]propyl urea,
(±)-cis-N-(3-fluoro-phenyl)-N'-[3-[4-(4-fluorophenylmethyl)-2-piperidinyl]propyl urea,
(±)-cis-N-(4-fluoro-phenyl)-N'-[3-[4-(4-fluorophenylmethyl)-2-piperidinyl]propyl urea,
(±)-cis-N-(3-chloro-phenyl)-N'-[3-[4-(4-fluorophenylmethyl)-2-piperidinyl]propyl urea,
(±)-cis-N-(4-chloro-phenyl)-N'-[3-[4-(4-fluorophenylmethyl)-2-piperidinyl]propyl urea,
(±)-cis-N-(3-methoxy-phenyl)-N'-[3-[4-(4-fluorophenylmethyl)-2-piperidinyl]propyl urea,
(±)-cis-N-phenyl-N'-[2-[4-(phenylmethyl)-2-piperidinyl]ethyl urea,
(±)-cis-N-(3-cyanophenyl)-N'-[2-[4-(phenylmethyl)-2-piperidinyl]ethyl urea,
(±)-cis-N-(3-acetylphenyl)-N'-[2-[4-(phenylmethyl)-2-piperidinyl]ethyl urea,
(±)-cis-N-(3-carbomethoxyphenyl)-N'-[2-[4-(phenylmethyl)-2-piperidinyl]ethyl urea,
(±)-cis-N-(3-carboethoxyphenyl)-N'-[2-[4-(phenylmethyl)-2-piperidinyl]ethyl urea,
(±)-cis-N-(3-fluorophenyl)-N'-[2-[4-(phenylmethyl)-2-piperidinyl]ethyl urea,
(±)-cis-N-(4-fluorophenyl)-N'-[2-[4-(phenylmethyl)-2-piperidinyl]ethyl urea,
(±)-cis-N-(3-chlorophenyl)-N'-[2-[4-(phenylmethyl)-2-piperidinyl]ethyl urea,
(±)-cis-N-(4-chlorophenyl)-N'-[2-[4-(phenylmethyl)-2-piperidinyl]ethyl urea,
(±)-cis-N-(3-methoxyphenyl)-N'-[2-[4-(phenylmethyl)-2-piperidinyl]ethyl urea,
(±)-cis-N-phenyl-N'-[2-[4-(4-fluorophenylmethyl)-2-piperidinyl]ethyl urea,
(±)-cis-N-(3-cyano-phenyl)-N'-[2-[4-(4-fluorophenylmethyl)-2-piperidinyl]ethyl urea,
(±)-cis-N-(3-acetyl-phenyl)-N'-[2-[4-(4-fluorophenylmethyl)-2-piperidinyl]ethyl urea,
(±)-cis-N-(3-carbomethoxy-phenyl)-N'-[2-[4-(4-fluorophenylmethyl)-2-piperidinyl]ethyl urea,
(±)-cis-N-(3-carboethoxy-phenyl)-N'-[2-[4-(4-fluorophenylmethyl)-2-piperidinyl]ethyl urea,
(±)-cis-N-(3-fluoro-phenyl)-N'-[2-[4-(4-fluorophenylmethyl)-2-piperidinyl]ethyl urea,
(±)-cis-N-(4-fluoro-phenyl)-N'-[2-[4-(4-fluorophenylmethyl)-2-piperidinyl]ethyl urea, (±)-cis-N-(3-chloro-phenyl)-N'-[2-[4-(4-fluorophenylmethyl)-2-piperidinyl]ethyl urea,
(±)-cis-N-(4-chloro-phenyl)-N'-[2-[4-(4-fluorophenylmethyl)-2-piperidinyl]ethyl urea,
(±)-cis-N-(3-methoxy-phenyl)-N'-[2-[4-(4-fluorophenylmethyl)-2-piperidinyl]ethyl urea,
(±)-cis-N-phenyl-N'-[4-(phenylmethyl)-2-piperidinyl]methyl urea,
(±)-cis-N-(3-cyanophenyl)-N'-[4-(phenylmethyl)-2-piperidinyl]methyl urea,
(±)-cis-N-(3-acetylphenyl)-N'-[4-(phenylmethyl)-2-piperidinyl]methyl urea,
(±)-cis-N-(3-carbomethoxyphenyl)-N'-[4-(phenylmethyl)-2-piperidinyl]methyl urea,
(±)-cis-N-(3-carboethoxyphenyl)-N'-[4-(phenylmethyl)-2-piperidinyl]methyl urea,
(±)-cis-N-(3-fluorophenyl)-N'-[4-(phenylmethyl)-2-piperidinyl]methyl urea,
(±)-cis-N-(4-fluorophenyl)-N'-[4-(phenylmethyl)-2-piperidinyl]methyl urea,
(±)-cis-N-(3-chlorophenyl)-N'-[4-(phenylmethyl)-2-piperidinyl]methyl urea,
(±)-cis-N-(4-chlorophenyl)-N'-[4-(phenylmethyl)-2-piperidinyl]methyl urea,
(±)-cis-N-(3-methoxyphenyl)-N'-[4-(phenylmethyl)-2-piperidinyl]methyl urea,
(±)-cis-N-phenyl-N'-[4-(4-fluorophenylmethyl)-2-piperidinyl]methyl urea,
(±)-cis-N-(3-cyano-phenyl)-N'-[4-(4-fluorophenylmethyl)-2-piperidinyl]methyl urea,
(±)-cis-N-(3-acetyl-phenyl)-N'-[4-(4-fluorophenylmethyl)-2-piperidinyl]methyl urea,
(±)-cis-N-(3-carbomethoxy-phenyl)-N'-[4-(4-fluorophenylmethyl)-2-piperidinyl]methyl urea,
(±)-cis-N-(3-carboethoxy-phenyl)-N'-[4-(4-fluorophenylmethyl)-2-piperidinyl]methyl urea,
(±)-cis-N-(3-fluoro-phenyl)-N'-[4-(4-fluorophenylmethyl)-2-piperidinyl]methyl urea,
(±)-cis-N-(4-fluoro-phenyl)-N'-[4-(4-fluorophenylmethyl)-2-piperidinyl]methyl urea,
(±)-cis-N-(3-chloro-phenyl)-N'-[4-(4-fluorophenylmethyl)-2-piperidinyl]methyl urea,
(±)-cis-N-(4-chloro-phenyl)-N'-[4-(4-fluorophenylmethyl)-2-piperidinyl]methyl urea,
(±)-cis-N-(3-methoxy-phenyl)-N'-[4-(4-fluorophenylmethyl)-2-piperidinyl]methyl urea,
(±)-trans-N-phenyl-N'-[3-[5-(phenylmethyl)-2-piperidinyl]propyl urea,
(±)-trans-N-(3-cyanophenyl)-N'-[3-[5-(phenylmethyl)-2-piperidinyl]propyl urea,
(±)-trans-N-(3-acetylphenyl)-N'-[3-[5-(phenylmethyl)-2-piperidinyl]propyl urea,
(±)-trans-N-(3-carbomethoxyphenyl)-N'-[3-[5-(phenylmethyl)-2-piperidinyl]propyl urea,
(±)-trans-N-(3-carboethoxyphenyl)-N'-[3-[5-(phenylmethyl)-2-piperidinyl]propyl urea,
(±)-trans-N-(3-fluorophenyl)-N'-[3-[5-(phenylmethyl)-2-piperidinyl]propyl urea,
(±)-trans-N-(4-fluorophenyl)-N'-[3-[5-(phenylmethyl)-2-piperidinyl]propyl urea,
(±)-trans-N-(3-chlorophenyl)-N'[3-[5-(phenylmethyl)-2-piperidinyl]propyl urea,
(±)-trans-N-(4-chlorophenyl)-N'[3-[5-(phenylmethyl)-2-piperidinyl]propyl urea,
(±)-trans-N-(3-methoxyphenyl)-N'-[3-[5-(phenylmethyl)-2-piperidinyl]propyl urea,
(±)-trans-N-phenyl-N'-[3-[5-(4-fluorophenylmethyl)-2-piperidinyl]propyl urea,
(±)-trans-N-(3-cyano-phenyl)-N'-[3-[5-(4-fluorophenylmethyl)-2-piperidinyl]propyl urea,
(±)-trans-N-(3-acetyl-phenyl)-N'-[3-[5-(4-fluorophenylmethyl)-2-piperidinyl]propyl urea,
(±)-trans-N-(3-carbomethoxy-phenyl)-N'-[3-[5-(4-fluorophenylmethyl)-2-piperidinyl]propyl urea,
(±)-trans-N-(3-carboethoxy-phenyl)-N'-[3-[5-(4-fluorophenylmethyl)-2-piperidinyl]propyl urea,
(±)-trans-N-(3-fluoro-phenyl)-N'-[3-[5-(4-fluorophenylmethyl)-2-piperidinyl]propyl urea,
(±)-trans-N-(4-fluoro-phenyl)-N'-[3-[5-(4-fluorophenylmethyl)-2-piperidinyl]propyl urea,
(±)-trans-N-(3-chloro-phenyl)-N'-[3-[5-(4-fluorophenylmethyl)-2-piperidinyl]propyl urea,
(±)-trans-N-(4-chloro-phenyl)-N'-[3-[5-(4-fluorophenylmethyl)-2-piperidinyl]propyl urea,
(±)-trans-N-(3-methoxy-phenyl)-N'-[3-[5-(4-fluorophenylmethyl)-2-piperidinyl]propyl urea,
(±)-trans-N-phenyl-N'-[2-[5-(phenylmethyl)-2-piperidinyl]ethyl urea,
(±)-trans-N-(3-cyanophenyl)-N'2-[5-(phenylmethyl)-2-piperidinyl]ethyl urea,
(±)-trans-N-(3-acetylphenyl)-N'-[2-[5-(phenylmethyl)-2-piperidinyl]ethyl urea,
(±)-trans-N-(3-carbomethoxyphenyl)-N'-[2-[5-(phenylmethyl)-2-piperidinyl]ethyl urea,
(±)-trans-N-(3-carboethoxyphenyl)-N'-[2-[5-(phenylmethyl)-2-piperidinyl]ethyl urea,
(±)-trans-N-(3-fluorophenyl)-N'-[2-[5-(phenylmethyl)-2-piperidinyl]ethyl urea,
(±)-trans-N-(4-fluorophenyl)-N'-[2-[5-(phenylmethyl)-2-piperidinyl]ethyl urea,
(±)-trans-N-(3-chlorophenyl)-N'-[2-[5-(phenylmethyl)-2-piperidinyl]ethyl urea,
(±)-trans-N-(4-chlorophenyl)-N'-[2-[5-(phenylmethyl)-2-piperidinyl]ethyl urea,
(±)-trans-N-(3-methoxyphenyl)-N'-[2-[5-(phenylmethyl)-2-piperidinyl]ethyl urea,
(±)-trans-N-phenyl-N'-[2-[5-(4-fluorophenylmethyl)-2-piperidinyl]ethyl urea,
(±)-trans-N-(3-cyano-phenyl)-N'-[2-[5-(4-fluorophenylmethyl)-2-piperidinyl]ethyl urea,
(±)-trans-N-(3-acetyl-phenyl)-N'-[2-[5-(4-fluorophenylmethyl)-2-piperidinyl]ethyl urea,
(±)-trans-N-(3-carbomethoxy-phenyl)-N'-[2-[5-(4-fluorophenylmethyl)-2-piperidinyl]ethyl urea,
(±)-trans-N-(3-carboethoxy-phenyl)-N'-[2-[5-(4-fluorophenylmethyl)-2-piperidinyl]ethyl urea,
(±)-trans-N-(3-fluoro-phenyl)-N'-[2-[5-(4-fluorophenylmethyl)-2-piperidinyl]ethyl urea,
(±)-trans-N-(4-fluoro-phenyl)-N'-[2-[5-(4-fluorophenylmethyl)-2-piperidinyl]ethyl urea,
(±)-trans-N-(3-chloro-phenyl)-N'-[2-[5-(4-fluorophenylmethyl)-2-piperidinyl]ethyl urea,
(±)-trans-N-(4-chloro-phenyl)-N'-[2-[5-(4-fluorophenylmethyl)-2-piperidinyl]ethyl urea,
(±)-trans-N-(3-methoxy-phenyl)-N'-[2-[5-(4-fluorophenylmethyl)-2-piperidinyl]ethyl urea,
(±)-trans-N-phenyl-N'-[5-(phenylmethyl)-2-piperidinyl]methyl urea,
(±)-trans-N-(3-cyanophenyl)-N'-[5-(phenylmethyl)-2-piperidinyl]methyl urea,
(±)-trans-N-(3-acetylphenyl)-N'-[5-(phenylmethyl)-2-piperidinyl]methyl urea,
(±)-trans-N-(3-carbomethoxyphenyl)-N'-[5-(phenylmethyl)-2-piperidinyl]methyl urea,
(±)-trans-N-(3-carboethoxyphenyl)-N'-[5-(phenylmethyl)-2-piperidinyl]methyl urea, (±)-trans-N-(3-fluorophenyl)-N'-[5-(phenylmethyl)-2-piperidinyl]methyl urea,
(±)-trans-N-(4-fluorophenyl)-N'-[5-(phenylmethyl)-2-piperidinyl]methyl urea,
(±)-trans-N-(3-chlorophenyl)-N'-[5-(phenylmethyl)-2-piperidinyl]methyl urea,
(±)-trans-N-(4-chlorophenyl)-N'-[5-(phenylmethyl)-2-piperidinyl]methyl urea,
(±)-trans-N-(3-methoxyphenyl)-N'-[5-(phenylmethyl)-2-piperidinyl]methyl urea,
(±)-trans-N-phenyl-N'-[5-(4-fluorophenylmethyl)-2-piperidinyl]methyl urea,
(±)-trans-N-(3-cyano-phenyl)-N'-[5-(4-fluorophenylmethyl)-2-piperidinyl]methyl urea,
(±)-trans-N-(3-acetyl-phenyl)-N'-[5-(4-fluorophenylmethyl)-2-piperidinyl]methyl urea,
(±)-trans-N-(3-carbomethoxy-phenyl)-N'-[5-(4-fluorophenylmethyl)-2-piperidinyl]methyl urea,
(±)-trans-N-(3-carboethoxy-phenyl)-N'-[5-(4-fluorophenylmethyl)-2-piperidinyl]methyl urea,
(±)-trans-N-(3-fluoro-phenyl)-N'-[5-(4-fluorophenylmethyl)-2-piperidinyl]methyl urea,
(±)-trans-N-(4-fluoro-phenyl)-N'-[5-(4-fluorophenylmethyl)-2-piperidinyl]methyl urea,
(±)-trans-N-(3-chloro-phenyl)-N'-[5-(4-fluorophenylmethyl)-2-piperidinyl]methyl urea,
(±)-trans-N-(4-chloro-phenyl)-N'-[5-(4-fluorophenylmethyl)-2-piperidinyl]methyl urea,
(±)-trans-N-(3-methoxy-phenyl)-N'-[5-(4-fluorophenylmethyl)-2-piperidinyl]methyl urea,
(±)-cis-N-phenyl-N'-[3-[5-(phenylmethyl)-2-piperidinyl]propyl urea,
(±)-cis-N-(3-cyanophenyl)-N'-[3-[5-(phenylmethyl)-2-piperidinyl]propyl urea,
(±)-cis-N-(3-acetylphenyl)-N'-[3-[5-(phenylmethyl)-2-piperidinyl]propyl urea,
(±)-cis-N-(3-carbomethoxyphenyl)-N'-[3-[5-(phenylmethyl)-2-piperidinyl]propyl urea,
(±)-cis-N-(3-carboethoxyphenyl)-N'-[3-[5-(phenylmethyl)-2-piperidinyl]propyl urea,
(±)-cis-N-(3-fluorophenyl)-N'-[3-[5-(phenylmethyl)-2-piperidinyl]propyl urea,
(±)-cis-N-(4-fluorophenyl)-N'-[3-[5-(phenylmethyl)-2-piperidinyl]propyl urea,
(±)-cis-N-(3-chlorophenyl)-N'-[3-[5-(phenylmethyl)-2-piperidinyl]propyl urea,
(±)-cis-N-(4-chlorophenyl)-N'-[3-[5-(phenylmethyl)-2-piperidinyl]propyl urea,
(±)-cis-N-(3-methoxyphenyl)-N'-[3-[5-(phenylmethyl)-2-piperidinyl]propyl urea,
(±)-cis-N-phenyl-N'-[3-[5-(4-fluorophenylmethyl)-2-piperidinyl]propyl urea,
(±)-cis-N-(3-cyano-phenyl)-N'-[3-[5-(4-fluorophenylmethyl)-2-piperidinyl]propyl urea,
(±)-cis-N-(3-acetyl-phenyl)-N'-[3-[5-(4-fluorophenylmethyl)-2-piperidinyl]propyl urea,
(±)-cis-N-(3-carbomethoxy-phenyl)-N'-[3-[5-(4-fluorophenylmethyl)-2-piperidinyl]propyl urea,
(±)-cis-N-(3-carboethoxy-phenyl)-N'-[3-[5-(4-fluorophenylmethyl)-2-piperidinyl]propyl urea,
(±)-cis-N-(3-fluoro-phenyl)-N'-[3-[5-(4-fluorophenylmethyl)-2-piperidinyl]propyl urea,
(±)-cis-N-(4-fluoro-phenyl)-N'-[3-[5-(4-fluorophenylmethyl)-2-piperidinyl]propyl urea,
(±)-cis-N-(3-chloro-phenyl)-N'-[3-[5-(4-fluorophenylmethyl)-2-piperidinyl]propyl urea,
(±)-cis-N-(4-chloro-phenyl)-N'-[3-[5-(4-fluorophenylmethyl)-2-piperidinyl]propyl urea,
(±)-cis-N-(3-methoxy-phenyl)-N'3-[5-(4-fluorophenylmethyl)-2-piperidinyl]propyl urea,
(±)-cis-N-phenyl-N'-[2-[5-(phenylmethyl)-2-piperidinyl]ethyl urea,
(±)-cis-N-(3-cyanophenyl)-N'-[2-[5-(phenylmethyl)-2-piperidinyl]ethyl urea,
(±)-cis-N-(3-acetylphenyl)-N'-[2-[5-(phenylmethyl)-2-piperidinyl]ethyl urea,
(±)-cis-N-(3-carbomethoxyphenyl)-N'-[2-[5-(phenylmethyl)-2-piperidinyl]ethyl urea,
(±)-cis-N-(3-carboethoxyphenyl)-N'-[2-[5-(phenylmethyl)-2-piperidinyl]ethyl urea,
(±)-cis-N-(3-fluorophenyl)-N'-[2-[5-(phenylmethyl)-2-piperidinyl]ethyl urea,
(±)-cis-N-(4-fluorophenyl)-N'-[2-[5-(phenylmethyl)-2-piperidinyl]ethyl urea,
(±)-cis-N-(3-chlorophenyl)-N'-[2-[5-(phenylmethyl)-2-piperidinyl]ethyl urea,
(±)-cis-N-(4-chlorophenyl)-N'-[2-[5-(phenylmethyl)-2-piperidinyl]ethyl urea,
(±)-cis-N-(3-methoxyphenyl)-N'-[2-[5-(phenylmethyl)-2-piperidinyl]ethyl urea,
(±)-cis-N-phenyl-N'-[2-[5-(4-fluorophenylmethyl)-2-piperidinyl]ethyl urea,
(±)-cis-N-(3-cyano-phenyl)-N'-[2-[5-(4-fluorophenylmethyl)-2-piperidinyl]ethyl urea,
(±)-cis-N-(3-acetyl-phenyl)-N'-[2-[5-(4-fluorophenylmethyl)-2-piperidinyl]ethyl urea,
(±)-cis-N-(3-carbomethoxy-phenyl)-N'-[2-[5-(4-fluorophenylmethyl)-2-piperidinyl]ethyl urea,
(±)-cis-N-(3-carboethoxy-phenyl)-N'-[2-[5-(4-fluorophenylmethyl)-2-piperidinyl]ethyl urea,
(±)-cis-N-(3-fluoro-phenyl)-N'-[2-[5-(4-fluorophenylmethyl)-2-piperidinyl]ethyl urea,
(±)-cis-N-(4-fluoro-phenyl)-N'-[2-[5-(4-fluorophenylmethyl)-2-piperidinyl]ethyl urea,
(±)-cis-N-(3-chloro-phenyl)-N'-[2-[5-(4-fluorophenylmethyl)-2-piperidinyl]ethyl urea,
(±)-cis-N-(4-chloro-phenyl)-N'-[2-[5-(4-fluorophenylmethyl)-2-piperidinyl]ethyl urea,
(±)-cis-N-(3-methoxy-phenyl)-N'-[2-[5-(4-fluorophenylmethyl)-2-piperidinyl]ethyl urea,
(±)-cis-N-phenyl-N'-[5-(phenylmethyl)-2-piperidinyl]methyl urea,
(±)-cis-N-(3-cyanophenyl)-N'-[5-(phenylmethyl)-2-piperidinyl]methyl urea,
(±)-cis-N-(3-acetylphenyl)-N'-[5-(phenylmethyl)-2-piperidinyl]methyl urea,
(±)-cis-N-(3-carbomethoxyphenyl)-N'-[5-(phenylmethyl)-2-piperidinyl]methyl urea,
(±)-cis-N-(3-carboethoxyphenyl)-N'-[5-(phenylmethyl)-2-piperidinyl]methyl urea,
(±)-cis-N-(3-fluorophenyl)-N'-[5-(phenylmethyl)-2-piperidinyl]methyl urea,
(±)-cis-N-(4-fluorophenyl)-N'-[5-(phenylmethyl)-2-piperidinyl]methyl urea,
(±)-cis-N-(3-chlorophenyl)-N'-[5-(phenylmethyl)-2-piperidinyl]methyl urea,
(±)-cis-N-(4-chlorophenyl)-N'-(5-(phenylmethyl)-2-piperidinyl]methyl urea,
(±)-cis-N-(3-methoxyphenyl)-N'-[5-(phenylmethyl)-2-piperidinyl]methyl urea,
(±)-cis-N-phenyl-N'-[5-(4-fluorophenylmethyl)-2-piperidinyl]methyl urea,
(±)-cis-N-(3-cyano-phenyl)-N'-[5-(4-fluorophenylmethyl)-2-piperidinyl]methyl urea,
(±)-cis-N-(3-acetyl-phenyl)-N'-[5-(4-fluorophenylmethyl)-2-piperidinyl]methyl urea, (±)-cis-N-(3-carbomethoxy-phenyl)-N'-[5-(4-fluorophenylmethyl)-2-piperidinyl]methyl urea,
(±)-cis-N-(3-carboethoxy-phenyl)-N'-[5-(4-fluorophenylmethyl)-2-piperidinyl]methyl urea,
(±)-cis-N-(3-fluoro-phenyl)-N'-[5-(4-fluorophenylmethyl)-2-piperidinyl]methyl urea,
(±)-cis-N-(4-fluoro-phenyl)-N'-[5-(4-fluorophenylmethyl)-2-piperidinyl]methyl urea,
(±)-cis-N-(3-chloro-phenyl)-N'-[5-(4-fluorophenylmethyl)-2-piperidinyl]methyl urea,
(±)-cis-N-(4-chloro-phenyl)-N'-[5-(4-fluorophenylmethyl)-2-piperidinyl]methyl urea, and
(±)-cis-N-(3-methoxy-phenyl)-N'-[5-(4-fluorophenylmethyl)-2-piperidinyl]methyl urea.

In other preferred embodiments, the present invention provides novel compounds of formula I, wherein the compound of formula I is selected from:

(±)-cis-N-{3-[4-benzyl-2-piperidinyl]propyl}-N'-(3-cyanophenyl)urea,
(±)-trans-N-(3-cyanophenyl)-N'-[2-[4-(benzyl)-2-piperidinyl]ethyl urea,
(±)-trans-N-{3-[4-benzyl-2-piperidinyl]propyl}-3-cyanobenzamide,
(±)-trans-N-(3-acetylphenyl)-N'-[2-[4-(benzyl)-2-piperidinyl]ethyl urea,
(±)-trans-N-{3-[4-benzyl-2-piperidinyl]propyl}-4-fluorobenzenesulfonamide,
(±)-trans-N-{3-[4-benzyl-2-piperidinyl]propyl}benzamide,
(±)-cis-N-(3-cyanophenyl)-N'-[3-[4-(4-fluorobenzyl)-2-piperidinyl]propyl urea,
(±)-trans-N-(3-acetylphenyl)-N'-[3-[4-(4-fluorobenzyl)-2-piperidinyl]propyl urea,
(±)-cis-N-(3-acetylphenyl)-N'-[3-[4-(4-fluorobenzyl)-2-piperidinyl]propyl urea,
(±)-trans-N-(3-chlorophenyl)-N'-[3-[4-(benzyl)-2-piperidinyl]propyl urea,
(±)-trans-N—(phenyl)-N'-[3-[4-(benzyl)-2-piperidinyl]propyl urea,
(±)-trans-N-(3-fluorophenyl)-N'-[3-[4-(benzyl)-2-piperidinyl]propyl urea,
(±)-trans-N-(3-methoxyphenyl)-N'-[3-[4-(benzyl)-2-piperidinyl]propyl urea,
(±)-trans-N-(4-carboethoxyphenyl)-N'-[3-[4-(benzyl)-2-piperidinyl]propyl urea,
(±)-trans-N-(4-fluorophenyl)-N'-[3-[4-(benzyl)-2-piperidinyl]propyl urea,
(±)-trans-N-(3-acetylphenyl)-N'-[3-[4-(benzyl)-2-piperidinyl]propyl urea,
(±)-trans-N-(3-trifluoromethylphenyl)-N'-[3-[4-(benzyl)-2-piperidinyl]propyl urea,
(±)-cis-N-(3-cyanophenyl)-N'-[3-[4-(benzyl)-1-propyl-2-piperidinyl]propyl urea,
(±)-trans-N-(3-acetylphenyl)-N'-[3-[4-(benzyl)-1-propyl-2-piperidinyl]propyl urea,
(±)-cis-N-(3-acetylphenyl)-N'-[3-[4-(4-fluorobenzyl)-1-propyl-2-piperidinyl]propyl urea,
(±)-trans-N-(3-acetylphenyl)-N'-[3-[4-(4-fluorobenzyl)-1-propyl-2-piperidinyl]propyl urea,
(±)-trans-N-(3-cyanophenyl)-N'-[4-[4-(benzyl)-2-piperidinyl]butyl urea,
(±)-trans-N-(3-acetylphenyl)-N'-[4-[4-(benzyl)-2-piperidinyl]butyl urea,
N-(3-acetylphenyl)-N'-{[3-[2S, 4S]-4-(4-fluorobenzyl)piperidinyl]propyl}urea,
N-(3-acetylphenyl)-N'-{[4-[2R, 4R]-4-(4-fluorobenzyl)-2-piperidinyl]butyl}urea,
N-(3-cyanophenyl)-N'-{[4-[2R, 4R]-4-(4-fluorobenzyl)piperidinyl]butyl}urea,
N-(3-acetylphenyl)-N'-{3-[(2S,4R)-4-(2,4-difluorobenzyl)piperidinyl]propyl}urea,
N-{3-[(2S,4R)-1-allyl-4-(4-fluorobenzyl)piperidinyl]propyl}-N'-(3,5-diacetylphenyl)urea,
N-(3,5-diacetylphenyl)-N'-{3-[(2S,4R)-4-(4-fluorobenzyl)-1-(2-hydroxyethyl)piperidinyl]propyl}urea,
N-{3-[(2S,4R)-1-acetyl-4-(4-fluorobenzyl)piperidinyl]propyl}-N'-(3,5-diacetylphenyl)urea,
N-(3,5-diacetylphenyl)-N'-{3-[(2S)-4-(4-fluorobenzyl)-1-(2-fluoroethyl)piperidinyl]propyl}urea,
(±)-trans-N-(3-acetylphenyl)-N'-[3-[4-(benzyl)-1-(2-hydroxyethyl)-2-piperidinyl]propyl urea,
(±)-trans-N-(3-acetylphenyl)-N'-[3-[4-(benzyl)-1-methyl-2-piperidinyl]propyl urea,
(±)-trans-N-(3-acetylphenyl)-N'-[3-[4-(benzyl)-1-ethyl-2-piperidinyl]propyl urea,
N-(3-acetylphenyl)-N'-{[3-(2R, 4R)-4-(4-fluorobenzyl)piperidinyl]propyl}urea,
N-(3-acetylphenyl)-N'-{[3-(2S, 4R)-4-(4-fluorobenzyl)piperidinyl]propyl}urea,
N-(3-acetylphenyl)-N'-{[3-(2S, 4R)-4-(4-fluorobenzyl)1-propylpiperidinyl]propyl}urea,
N-(3-acetylphenyl)-N'-{[3-(2S, 4R)-4-(4-fluorobenzyl)1-methylpiperidinyl]propyl}urea,
N-(3-acetylphenyl)-N'-{[3-(2S, 4R)-4-(4-fluorobenzyl)-1-(2-hydroxyethyl)piperidinyl]propyl}urea,
[(2S,4R)-2-(3-{[[(3-acetylanilino)carbonyl]amino}propyl)-4-(4-fluorobenzyl)piperidinyl]acetic acid,
N-(3-acetylphenyl)-N'-{3-[(2S,4R)-1-benzyl-4-(4-fluorobenzyl)piperidinyl]propyl}urea,
(±)-trans-N-{3-[(4-benzyl-2-piperidinyl]propyl}-N'-(3-fluoro-4-methylphenyl)urea,
(±)-trans-N-{3-[4-benzyl-2-piperidinyl]propyl}-N'-(3,4-dimethoxyphenyl)urea,
(±)-trans-N-{3-[4-benzyl-2-piperidinyl]propyl}-N'-(6-methoxy-3-pyridinyl)urea,
(±)-trans-N-{3-[4-benzyl-2-piperidinyl]propyl}-N'-(1H-indazol-6-yl)urea,
N-(3-acetylphenyl)-N'-{3-[(2S,4R)-1-(cyclopropylmethyl)-4-(4-fluorobenzyl)piperidinyl]propyl}urea,
N-(3-cyanophenyl)-N'-{3-[(2S,4R)-4-(4-fluorobenzyl)piperidinyl]propyl}urea,
N-(3-cyanophenyl)-N'-{3-[(2S,4R)-4-(4-fluorobenzyl)-1-propylpiperidinyl]propyl}urea,
N-(3-acetylphenyl)-N'-{3-[(2S,4R)-1-allyl-4-(4-fluorobenzyl)piperidinyl]propyl}urea,
N-{3-[(2S,4R)-4-(4-fluorobenzyl)piperidinyl]propyl}-N'-[3-(1-methyl-1H-tetraazol-5-yl)phenyl]urea,
N-{3-[(2S,4R)-4-(4-fluorobenzyl)-1-propylpiperidinyl]propyl}-N'-[3-(1-methyl-1H-tetraazol-5-yl)phenyl]urea,
(2S,4R)-2-(3-{[(E)-{[(E)-amino(oxo)methyl]imino}(3,5-diacetylanilino)methyl]amino}propyl)-4-(4-fluorobenzyl)-N-methyl-1-piperidinecarboxamide,
N-[(E)-({3-[(2S,4R)-1-acetyl-4-(4-fluorobenzyl)piperidinyl]propyl}amino)(3,5-diacetylanilino)methylidene]urea,
N''-cyano-N-(3,5-diacetylphenyl)-N'-{3-[(2S,4R)-4-(4-fluorobenzyl)-1-(2-hydroxyethyl)piperidinyl]propyl}guanidine,
N-(3,5-diacetylphenyl)-N'-{3-[(2S,4R)-4-(4-fluorobenzyl)piperidinyl]propyl}urea,
N-(3,5-diacetylphenyl)-N'-{3-[(2S)-4-(4-fluorobenzyl)-1-propylpiperidinyl]propyl}urea,
N-[(E)-(3,5-diacetylanilino)({3-[(2S,4R)-4-(4-fluorobenzyl)piperidinyl]propyl}amino)methylidene]urea, N"-cyano-N-(3,5-diacetylphenyl)-N'-}3-[(2S,4R)-4-(4-fluorobenzyl)piperidinyl]propyl}guanidine,
(2S,4R)-2-(3-{[(3,5-diacetylanilino)carbonyl]amino}propyl)-4-(4-fluorobenzyl)-1-piperidinecarboximidamide,
N"-cyano-N-(3,5-diacetylphenyl)-N'-{3-[(2S,4R)-4-(4-fluorobenzyl)-1-propylpiperidinyl]propyl}guanidine,
(2S,4S)-2-(3-{[(3-acetylanilino)carbonyl]amino}propyl)-4-(4-fluorobenzyl)-1-piperidinecarboximidamide,
N-{3-[(2S,4R)-1-(aminoacetyl)-4-(4-fluorobenzyl)piperidinyl]propyl}-N'-(3,5-diacetylphenyl)urea,
N-{3-[(2S,4R)-1-allyl-4-(4-fluorobenzyl)piperidinyl]propyl}-N"-cyano-N'-(3,5-diacetylphenyl)guanidine,
N"-cyano-N-(3,5-diacetylphenyl)-N'-{3-[(2S,4R)-4-(4-fluorobenzyl)-1-(2-fluoroethyl)piperidinyl]propyl}guanidine,
N"-cyano-N-(3,5-diacetylphenyl)-N'-[3-[(2S,4R)-4-(4-fluorobenzyl)-1-(2-propynyl)piperidinyl]propyl}guanidine,
N"-cyano-N-(3,5-diacetylphenyl)-N'-{3-[(2S,4R)-4-(4-fluorobenzyl)-1-methylpiperidinyl]propyl}guanidine,
N"-cyano-N-(3,5-diacetylphenyl)-N'-{3-[(2S,4R)-1-ethyl-4-(4-fluorobenzyl)piperidinyl]propyl}guanidine,
N-[3,5-bis(1-methyl-1H-tetraazol-5-yl)phenyl]-N'-}3-[(2S,4R)-4-(4-fluorobenzyl)piperidinyl]propyl}urea,
N-{3-[(2S,4R)-1-acetyl-4-(4-fluorobenzyl)piperidinyl]propyl}-N'-[3,5-bis(1-methyl-1H-tetraazol-5-yl)phenyl]urea,
N-(3,5-diacetylphenyl)-N'-{3-[(2S, 4R)-1-(2,2-difluoroethyl)-4-(4-fluorobenzyl)piperidinyl]propyl}urea,
N-(3,5-diacetylphenyl)-N'-{3-[(2S, 4R)-4-(4-fluorobenzyl)-1-(methylsulfonyl)piperidinyl]propyl}urea,
N-(3,5-diacetylphenyl)-N'-{3-[(2S, 4R)-4-(4-fluorobenzyl)-1-propionylpiperidinyl]propyl}urea,
N-(3,5-diacetylphenyl)-N'-{3-[(2S, 4R)-4-(4-fluorobenzyl)-1-isobutyrylpiperidinyl]propyl}urea,
(2S, 4R)-2-(3-{[(3,5-diacetylanilino)carbonyl]amino}propyl)-4-(4-fluorobenzyl)-N-methyl-1-piperidinecarboxamide,
(2S, 4R)-2-(3-{[(3,5-diacetylanilino)carbonyl]amino}propyl)-4-(4-fluorobenzyl)-1-piperidinecarboxamide,
N-(3,5-diacetylphenyl)-N'-{3-[(2S, 4R)-4-(4-fluorobenzyl)-1-(2-pyridinylmethyl)piperidinyl]propyl}urea, 2-[(2S, 4R)-2-(3-{[(3,5-diacetylanilino)carbonyl]amino}propyl)-4-(4-fluorobenzyl)piperidinyl]acetamide,
N-{3-[(2S, 4R)-1-[(2S)-2-aminopropanoyl]-4-(4-fluorobenzyl)piperidinyl]propyl}-N'-(3,5-diacetylphenyl)urea,
N-{3-[(2S, 4R)-1-[(2R)-2-aminopropanoyl]-4-(4-fluorobenzyl)piperidinyl]propyl}-N'-(3,5-diacetylphenyl)urea,
N-(3,5-diacetylphenyl)-N'-(3-[(2S, 4R)-4-(4-fluorobenzyl)-1-(2-propynyl)piperidinyl]propyl}urea,
1-(3-{[(E)-1-({3-[(2S)-4-(4-fluorobenzyl)piperidinyl]propyl}amino)-2-nitroethenyl]amino}phenyl)ethanone,
(±)-trans-N-{3-[4-(benzyl)-2-piperidinyl]propyl}-N'-[3-(phenylsulfonyl)phenyl]urea,
(±)-trans-N-{3-[4-(benzyl)-2-piperidinyl]propyl}-N'-[3-chloro-4-(diethylamino)phenyl]urea,
(±)-trans-N-(3-{[({3-[4-benzyl-2-piperidinyl]propyl}amino)carbonyl]amino}phenyl) acetamide,
(±)-trans-N-{3-[4-benzylpiperidinyl]-2-propyl}-N'-[3-(1-hydroxyethyl)phenyl]urea,
(±)-trans-dimethyl 5-{[({3-[4-benzyl-2-piperidinyl]propyl}amino)carbonyl]amino}isophthalate,
(±)-trans-ethyl 3-{[({3-[4-benzyl-2-piperidinyl]propyl}amino)carbonyl]amino}benzoate,
(±)-trans-N-{3-[4-benzyl-2-piperidinyl]propyl}-N'-(3-chlorophenyl)urea,
N-(3,5-diacetylphenyl)-N'-{3-[(2S,4R)-4-(4-fluorobenzyl)-1-(2-oxo-propyl)piperidinyl]propyl}urea,
N-[3-(2-{3-[(3,5-diacetylanilinocarbonyl) amino}propyl]-4-(4-fluorobenzyl)-1-piperidinyl)propyl]acetamide,
N-(3,5-diacetylphenyl)-N'-(3-[(2S,4R)-4-(4-fluorobenzyl)-1-(3-hydroxypropyl)piperidinyl]propyl}urea,
N"-cyano-N-(3,5-diacetylphenyl)-N'-{3-[(2S,4R)-4-(4-fluorobenzyl)-1-(2-oxo-propyl)piperidinyl]propyl}guanidine, and
N"-cyano-N-(3,5-diacetylphenyl)-N'-{3-[(2S,4R)-4-(4-fluorobenzyl)-1-(3-hydroxypropyl)piperidinyl]propyl}guanidine.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides a method for treating inflammatory disorders comprising administering to a patient in need thereof a therapeutically effective amount of a compound of the present invention In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The compounds of Formula I can also be quaternized by standard techniques such as alkylation of the piperidine or pyrrolidine with an alkyl halide to yield quaternary piperidinium salt products of Formula I. Such quaternary piperidinium salts would include a counterion. As used herein, "counterion" is used to represent a small, negatively charged species such as chloride, bromide, hydroxide, acetate, sulfate, and the like.

As used herein, the term "piperidinium spirocycle or pyrrolidinium spirocycle" is intended to mean a stable spirocycle ring system, in which the two rings form a quarternary nitrogene at the ring junction.

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3- to 10-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, (4.4.0)bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated, partially unsaturated, or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

As used herein, the term "amino acid" or "amino acid residue" is intended to have its art-recognized meaning as a molecule containing both an amino group and a carboxyl group separated by a carbon. Embodiments of amino acids include α-amino acids; i.e., carboxylic acids of general formula HOOC—CH(NH2)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, Biochemistry, Second Edition, Worth Publishers, Inc, 1975, pages 73–75, the disclosure of which is hereby incorporated by reference. In certain embodiments, substituent groups for the compounds include the residue of an amino acid after removal of the hydroxyl moiety of the carboxyl group thereof; i.e., groups of Formula —C(=O)CH(side chain) (N(G)$_2$)—, wherein G is a group including, but not limited to, hydrogen, a nitrogen protecting group, or another amino acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The following abbreviations are used herein: "THF" as used herein is intended to mean tetrahydrofuran, "EtOAc" as used herein is intended to mean ethyl acetate, "DMAP" as used herein is intended to mean 4-N,N-dimethylamino pyridine, "9-BBN" as used herein is intended to mean 9-borabicyclo [3.3.1]nonane, "Boc$_2$O" as used herein is intended to mean Di-tert-Butyl dicarbonate, "NMO" as used herein is intended to mean N-methyl morpholine-N-oxide, "TPAP" as used herein is intended to mean tetrapropylammonium perruthenate, "TFA" as used herein is intended to mean trifluoroacetic acid. The compounds of Formula I can be prepared using the reactions and techniques described below.

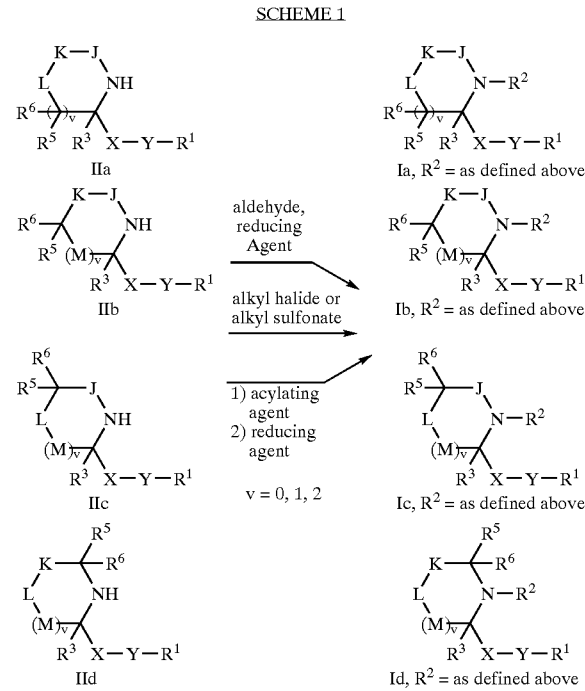

SCHEME 1

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

SCHEME 2

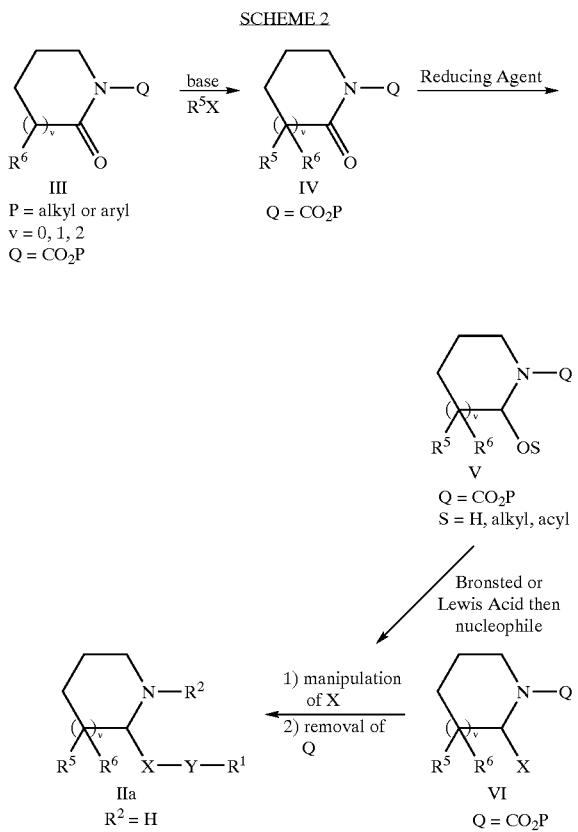

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Compounds of the Formula Ia–d are prepared by alkylating heterocycles IIa–d by using the appropriate conditions according to Scheme 1. Thus, heterocycles Ia–d can be alkylated with an alkyl sulfonate or alkyl halide according to the general methods described for this transformation in March, J. *"Advanced Organic Chemistry,"* 4th Ed., John Wiley and Sons, New York, 1992, pp. 411–413 (Herein after March, 4th Ed.) Heterocycles IIa–d can also be treated with an aldehyde and an appropriate reducing agent to give Ia–d as described in March, 4th Ed. (pp. 898–900.)

The required aldehydes can be prepared by methods generally known to those skilled in the art of organic synthesis. Furthermore, heterocycles IIa–d can be acylated and the resulting amides reduced by the appropriate reducing agent to give Ia–d using procedures described in March, 4th Ed. (pp. 419–421 and 1212–1213, respectively.) Heterocycle IIa can be prepared by the following sequence outlined in Scheme 2. Imide III can be alkylated with an alkyl sulfonate, triflate or halide according to the methods described in the literature, more specifically, but not limited to, as described by Dieter, R. K. et al., *Journal of Organic Chemistry*, 1996, Vol. 61, pp. 4180–4184 to give IV. Substituted imide IV can then be reduced to the α-alkoxy or α-hydroxy urethane V according to the methods described in the literature, more specifically, but not limited to, as described by Nagasaka, T. et. al, *Heterocycles*, Vol. 24, No. 5, 1986.

Ionization of urethane V with a Bronstead or Lewis Acid generates an electrophilic acyl iminium ion which can be treated with a variety of nucleophiles according to the general methods outlined by, but not limited to, Shono, T. *Tetrahedron*, Vol. 40. No. 5, pp. 811–850, 1984., to give heterocycle VI. The side chain functionality (X) of VI can then be further modified or functionalized, if necessary, and the nitrogen deprotected (removal of Q), both using methods known to those skilled in the art of organic synthesis to provide heterocycle IIa.

SCHEME 2A

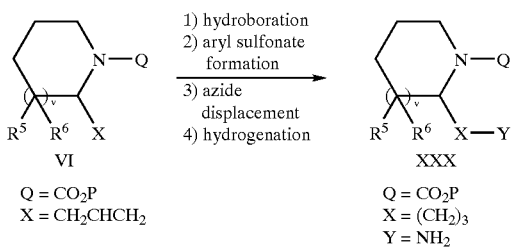

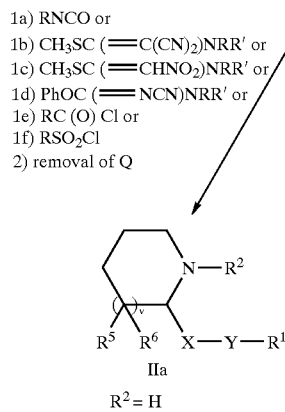

By way of further illustration (Scheme 2a), when X=—CH$_2$CH=CH$_2$ (allyl), manipulation by hydroboration, conversion to an alkyl or aryl sulfonate, displacement with azide and hydrogenation provides amine XXX. Reaction with the appropriate acylating reagent and removal of Q will provide heterocycles of the formula IIa. All of these simple transformations are known to those skilled in the art of organic synthesis. Furthermore, the preparation and use of several of the acylating reagents described in Scheme 2a is illustrated in P. Traxler, et al., J. Med. Chem. (1997), 40, 3601–3616 for reagent 1b and 1d; see K. S. Atwal, J. Med. Chem. (1998) 41, 271 for reagent 1c; and see also J. M. Hoffman, et al., J. Med. Chem. (1983) 26, 140–144).

SCHEME 3

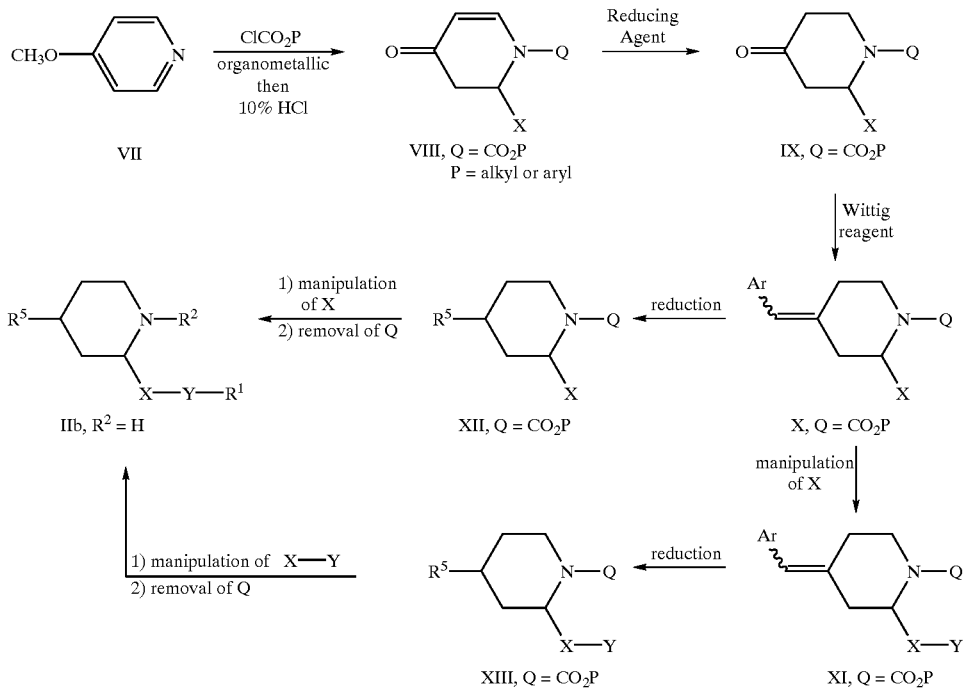

Heterocycle IIb can be prepared by the sequence outlined in Scheme 3. Unsaturated imide VIII can be prepared by the methods described in the literature, more specifically, but not limited to, as described by Comins, D., et al., *Adv. Nitrogen Heterocycl.*, 1996, Vol. 2, pp. 251–294. Thus, pyridines of the formula VII can be converted to their pyridinium salts at low temperature, treated with an appropriate nucleophile and subsequently hydrolized to vinylogous imides of the formula VIII. This procedure can be conveniently performed to produce racemic material or be slightly modified to produce material of high enantiomeric excess. At this juncture, the urethane functionality (O) can be modified, if warranted, to facilitate more convenient removal of Q at the end of the synthetic sequence. Imide VIII can be reduced according to methods known to those skilled in the art of organic synthesis to give ketone IX. Ketone IX can be converted to urethane X according to methods described in March, 4th Ed., pp. 956–963. The resulting urethane X can be processed in two separate manners. The side chain X can be manipulated prior to reduction of the olefin to give XI. Olefin XI and/or urethane X can then be reduced with reagents known to those skilled in the art of organic synthesis.

For example, by treatment with $H_2(g)$ accompanied by the appropriate catalyst (including, but not limited, to $PtO_2$ or Pd on carbon) or by treatment with an alkaline earth metal such as lithium, sodium or calcium in the appropriate solvent mixture (ammonia mixed with THF or diethyl ether) to give XII or XIII, respectively. Heterocycle IIb can be prepared from XIII and/or XII with similar transformations described above for heterocycle VI.

SCHEME 4

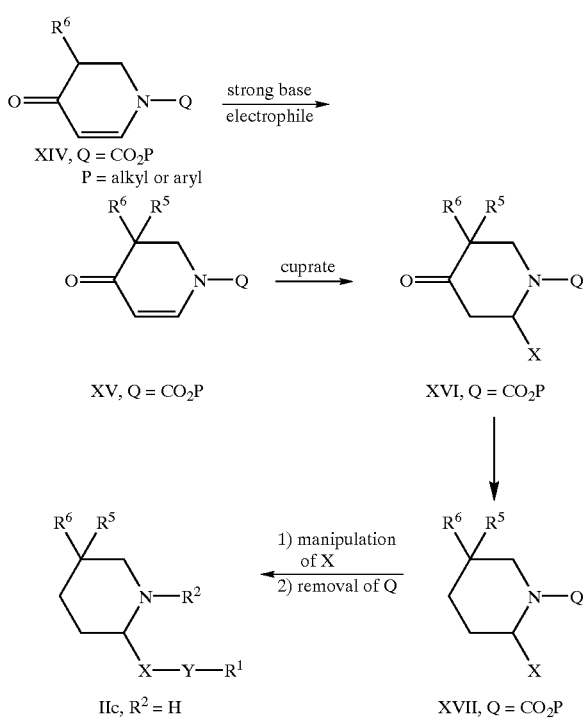

Imides similar to VIII (XIV) can also be converted into heterocycles of the formula IIc according to Scheme 4. Thus, treatment of XIV with strong base followed by alkylation of the resulting enolate with an appropriate electrophile generates unsaturated imide XV. Reaction of XV with an organometallic derivative according to, but not limited to, procedures described in March, 4th Ed., pp. 797–803 would provide ketone XVI. Reduction of ketone XVI using a variety of conditions described in, but not limited to, March, 4th Ed., pp. 1209–1211 would provide urethane XVII. Manipulation of XVII as previously described for VI and XII will yield heterocyles of the formula IIc.

SCHEME 5

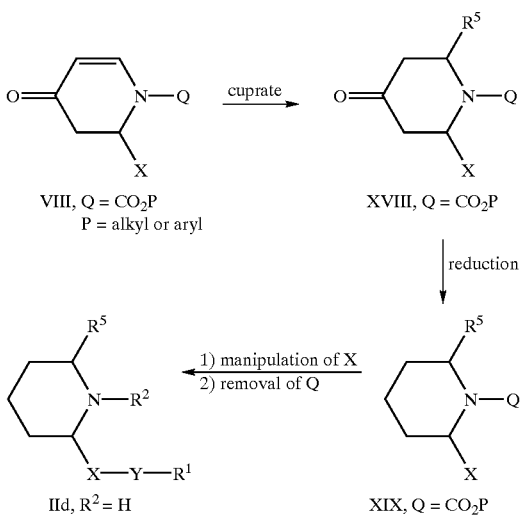

VIII, Q = $CO_2P$
P = alkyl or aryl

XVIII, Q = $CO_2P$

IId, $R^2$ = H

XIX, Q = $CO_2P$

Imide VIII can also be used in the formation of compounds of the formula IId (Scheme 5). Thus, reaction of VIII with an organometallic reagent in an analogous fashion to the formation of XVI would provide XVIII. Reduction of the ketone XVIII using conditions described for ketone XVI would provide XIX. Conversion of XIX using the conditions previously described for VI, XII and XVII would give compounds of the formula IId.

SCHEME 6

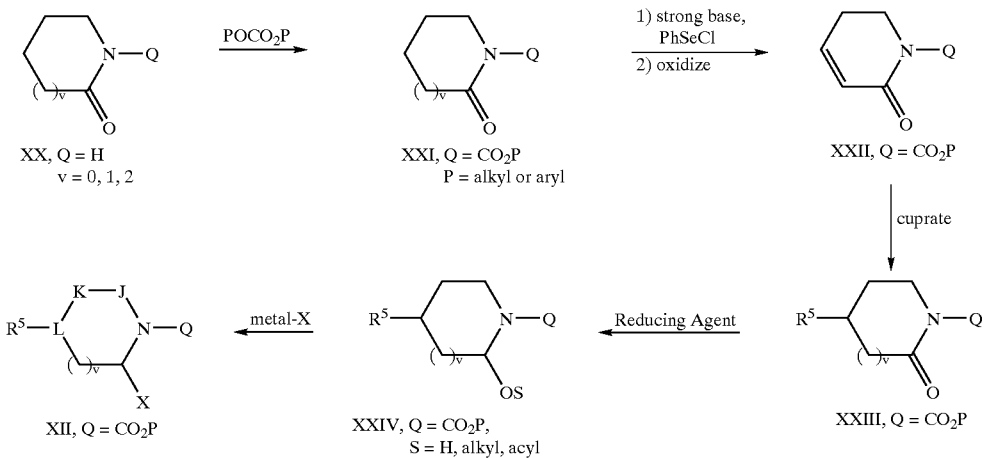

XX, Q = H
v = 0, 1, 2

XXI, Q = $CO_2P$
P = alkyl or aryl

XXII, Q = $CO_2P$

XII, Q = $CO_2P$

XXIV, Q = $CO_2P$,
S = H, alkyl, acyl

XXIII, Q = $CO_2P$

Heterocycles of the formula XII can also be prepared according to the procedure described in Scheme 6. Imide XXI can be prepared by the acylation of amide XX using the procedure described by, but not limited to, Hansen, M. M., et al., *Tetrahedron Letters*, Vol. 36. 1995, pp. 8949–8952. Imide XXI is then converted to unsaturated imide XXII by sulfenylation and oxidative elimination according to the procedures described in, but not limited to, Zoretic, P. A., et al., *Journal of Organic Chemistry*, Vol. 41, 1976, pp. 3587–89 and Torisawa, Y., et al., *Journal of Organic Chemistry*, Vol. 57, 1992, pp. 5741–5747, repectively. The $R^5$ substituent can then be introduced using methods described in Scheme 4 for the conversion of XV to XVI. Imide XXIII can then be converted to heterocycle XII (via the intermediacy of XXIV) using the sequence described in Scheme 2 for the conversion of IV (via V) to VI.

Heterocycles of the formula VI, XII, XVII and XIX can also be prepared by the sequence described in Scheme 7. Aldehydes of the formula XXVa–d can be converted to acyl iminium ion precursors using the conditions described by, but not limited to, Speckamp, W. N. et al, in "*Comprehensive Organic Synthesis*" B. M. Trost, Editor, Volume 2, pp. 1047–1082. The resulting protected lactamols of the formula XXVIa–d can also be prepared from amino acids of the formula XXVIIa–d. Cyclization of XXVIIa–d using conditions previously described for, but not limited to, IIa–d (Scheme 1, March, 4th. Ed. pp. 419–421) followed by partial reduction of the resulting imide (see the synthesis of V and XXIII, Scheme 2 and 6, respectively) and subsequent protection of the lactamol will provide XXVIa–d.

SCHEME 7

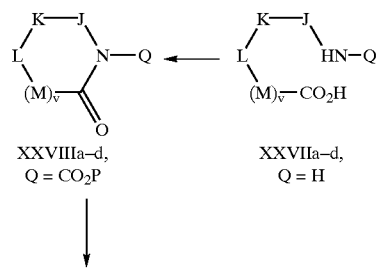

XXVIIIa–d,
Q = $CO_2P$

XXVIIa–d,
Q = H

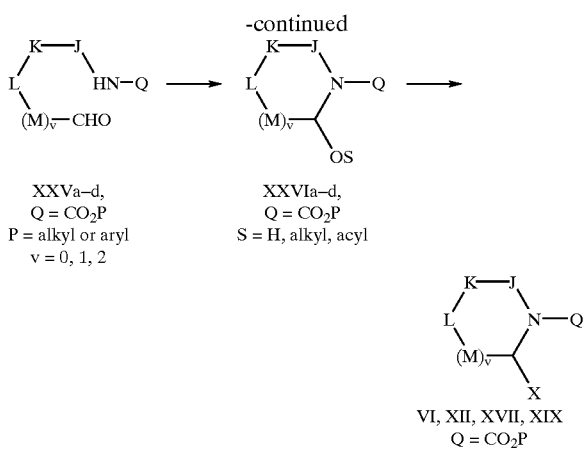

XXVa–d,
Q = CO₂P
P = alkyl or aryl
v = 0, 1, 2

XXVIa–d,
Q = CO₂P
S = H, alkyl, acyl

VI, XII, XVII, XIX
Q = CO₂P

The resulting lactamols (or their protected counterparts) can then be transformed into compounds of the formula VI, XII, XVII and XIX using conditions previously described for v (Scheme 2) or XXIV (Scheme 6). Acyclic precursors of the formula XXVa–d and XXVIIa–d can be prepared using methods know to those skilled in the art of organic synthesis.

Compounds of Formula XXIXa–d can be prepared by the method depicted in Scheme 8. The quaternary salts can be synthesized according to the methods described by, but not limited to, March, 4th Ed., pp. 411–413. The N-oxides of Formula XXIXa–d can be synthesized according to the methods described by, but not limited to, March, 4th Ed., pp. 1200-1201.

SCHEME 8

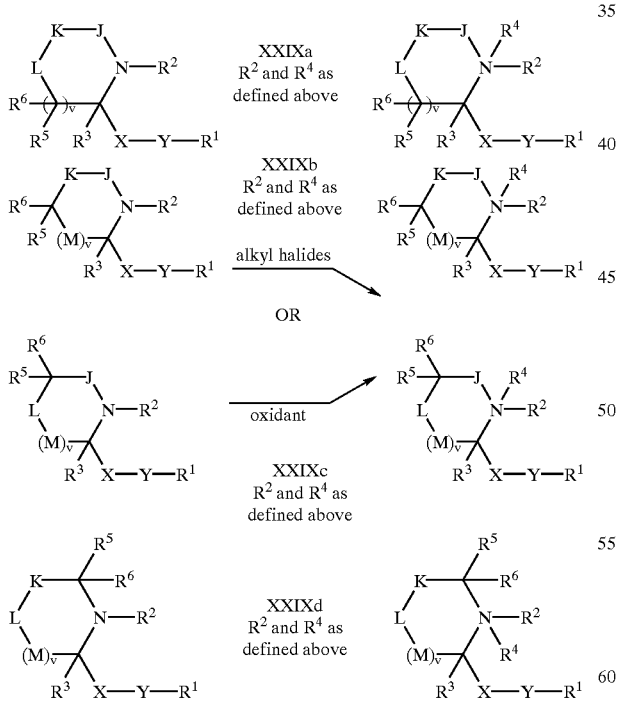

XXIXa
R² and R⁴ as defined above

XXIXb
R² and R⁴ as defined above alkyl halides

OR oxidant

XXIXc
R² and R⁴ as defined above

XXIXd
R² and R⁴ as defined above

The compounds of this invention and their preparation can be further understood by the following working examples. These examples are meant to be illustrative of the present invention and are not meant to be taken as limiting thereof.

EXAMPLE 1

(+)-N-(3-cyanophenyl)-N'-{[3-(2S, 4R)-4-(benzyl)piperidinyl]propyl}urea
and
(−)-N-(3-cyanophenyl)-N'-{[3-(2R, 4S)-4-(benzyl)piperidinyl]propyl}urea Step 1

To a −23° C. solution of 4-methoxypyridine (45.8 mmol) in 200 mL of THF was added dropwise phenylchloroformate (50.4 mmol). The resulting slurry was stirred at this temperature for 1 hour. After cooling to −78° C., allylmagnesium chloride was added dropwise and the resulting solution stirred at this temperature for 2 hours. The reaction was then quenched by the addition of 40 mL of 1N HCl, warmed to room temperature and stirred for 12 hours. The resulting aqueous layer was extracted with EtOAc (3 times). The combined organic layer was washed successively with saturated NaHCO₃ and brine. The resulting solution was dried over magnesium sulfate, filtered, and concentrated in vacuo. The remaining oil was purified using flash chromatography (silica, 0–50% EtOAc/hexanes) to give 7.2 g of 1 (Scheme 9). ¹³C NMR (CDCl₃) δ 35.4, 39.5, 53.1, 108.1, 119.4, 121.2, 126.4, 129.6, 132.8, 141.0, 150.5, 182.4, 192.5 ppm. Mass spectrum [NH₃/CI], [(M+H)⁺]=258.

SCHEME 9

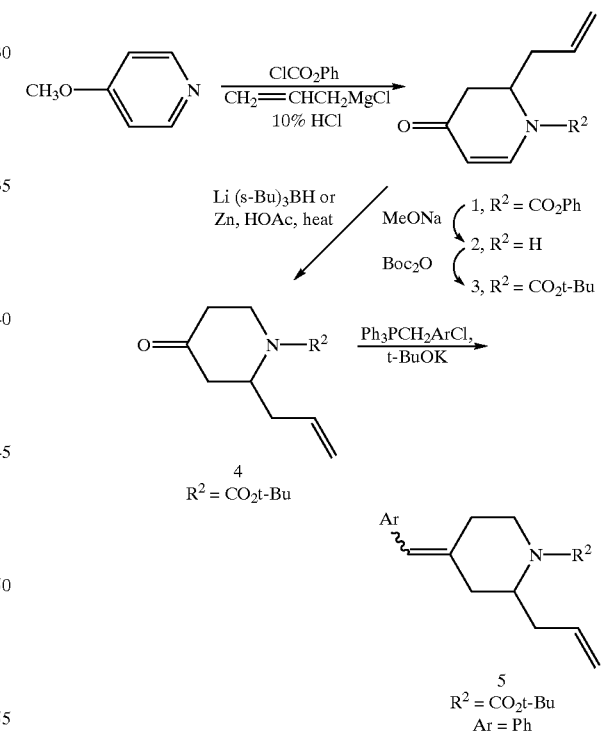

Step 2

To a solution of 1 (6.40 g) in 60 mL of methanol was added 6.3 mL of a 25% solution of sodium methoxide in methanol. The resulting solution was warmed to reflux for 30 minutes and then cooled to room temperature. The pH of the solution was adjusted to a pH of seven by the careful addition of the appropriate amount of 1 N HCl. The resulting solution was concentrated in vacuo and the remaining aqueous layer extracted with ether (3 times). The aqueous layer was freeze dried, suspended in EtOAc, filtered and concentrated in vacuo. The ether layer was concentrated in vacuo and the residue purified by column chromatography (silica, 50% EtOAc/hexanes then 0–10% MeOH/CH$_2$Cl$_2$). The two resulting oils (2) (3.1 g) were combined and dissolved in acetonitrile (50 mL). This reaction mixture was charged with Boc$_2$O (1.28 g) and 4-dimethylamino pyridine (0.024 g) and stirred for one hour. It was then diluted with EtOAc and washed successively with 1N HCl, saturated NaHCO$_3$ and brine. The organic layer was dried over magnesium sulfate, filtered and concentrated in vacuo. The residue was purified by flash chromatography (silica, 0–50% EtOAc/hexanes) to give 5.9 g of 3. $^{13}$C NMR (CDCl$_3$) δ 27.9, 35.0, 39.2, 52.3, 83.2, 106.1, 118.7, 133.1, 141.8, 151.1, 192.6 ppm. Mass spectrum [NH3/CI], [(M+H)$^+$]=238.

Step 3

To a solution of 3 (6.73 g) in 60 mL of THF at −78° C. was added dropwise lithium-tri-sec-butyl borohydride (31.2 mL of a 1M THF solution) over a 15 minute period. The resulting solution was stirred at −78° C. for an additional 60 minutes, quenched by the dropwise addition of water and warmed to room temperature. Concentration in vacuo followed by purification using flash chromatography (silica, 0–50% EtOAc/hexanes) provided 4.98 g of 4. $^{13}$C NMR (CDCl$_3$) δ 28.3, 37.2, 38.4, 40.5, 44.5, 51.6, 80.4, 118.1, 133.5, 154.6, 208.0 ppm. Mass spectrum [NH$_3$/CI], [(M+H)$^+$]=240.

Step 3a

Alternatively, enone 3 can be reduced by the following procedure. To a solution of enone 3 (18.7 g, 78.8 mmol) in 180 mL of glacial acetic acid was added in small portions Zn dust (278 mmol) so that the internal temperature never rises above 50° C. After complete addition of the metal, the reaction was allowed to stir 12 h at 45° C. After cooling to room temperature the reaction mixture was filtered and the zinc salts washed with 5–15 mL portions of EtOAc. Concentration of the combined organic layers in vacuo followed by purification using flash chromatography (silica, 20% EtOAc/hexanes) provided 17.1 g of ketone 4.

Step 4

To a suspension of benzyltriphenyl phosphonium chloride (32.2 g) in 75 mL of THF was added 79 mL (1M in THF) of potassium t-butoxide. After stirring at room temperature for 20 minutes, ketone 4 was added dropwise in 100 mL of THF. The resulting solution was stirred for 12 hours. The reaction was then quenched by the addition of 2N HCl and poured into ether. The aqueous layer was extracted twice with ether. The combined organic layer was washed successively with saturated NaHCO$_3$ and brine. The resulting solution was then dried over magnesium sulfate, filtered and concentrated in vacuo. The residue was slurried in hexanes, filtered and concentrated in vacuo. Purification using flash chromatography (silica, 0–20% EtOAc/hexanes) provided an approximately 1:1 mixture of E and Z-5. Mass spectrum [NH$_3$/CI], [(M+H)$^+$]=314.

Step 5

To a solution of 9-BBN dimer (3.48 g) in 40 mL of THF at 0° C. was added dropwise a mixture of E and Z-5 (6.5 g) in 40 mL of THF. The reaction was warmed to room temperature and stirred for 75 minutes. The reaction was then cooled to 0° C., treated with 35 mL of pH=7.2 phosphate buffer and 35 mL of 35% hydrogen peroxide. The resulting mixture was allowed to warm to room temperature and stirred for an additional 1 hour. The solution was then concentrated in vacuo and the remaining residue dissolved in ether. The resulting organic layer was washed successively with 1N NaHSO$_3$ and brine. The organic layer was then dried over magnesium sulfate, filtered and concentrated in vacuo. The residue was then purified using flash chromatography (silica, 0–50% EtOAc/hexanes) to provide 6.85 g of an approximately 1:1 mixture of E and Z-6 (Scheme 10). Mass spectrum [ESI], [(M+H)$^+$]=332.

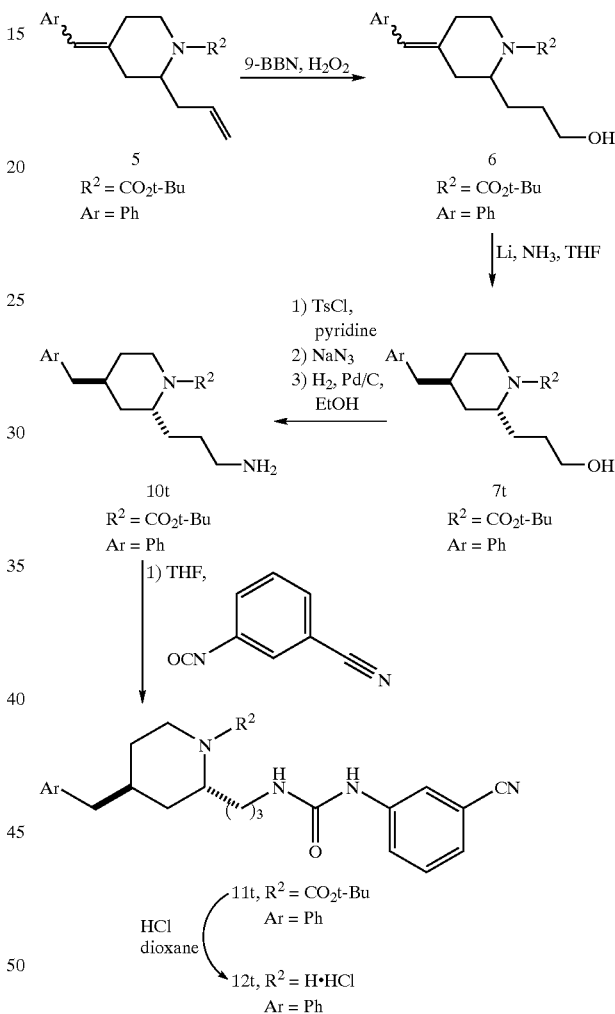

SCHEME 10

Step 6

To a solution of approximately 100 mL of dry doubly-distilled ammonia at −78° C. was added 66 mL of THF and 733 mg of lithium metal. The resulting solution was allowed to stir for 20 minutes and then 3.42 g of a mixture of E and Z-6 was added dropwise in 33 mL of THF. The reaction was then quenched by the slow addition of ammonium chloride and warmed to room temperature. After stirring for 60 minutes the residue was poured into ether and washed successively with water and brine. The organic layer was dried over magnesium sulfate, filtered and concentrated in vacuo. Purification using flash chromatography (silica, 0–35% EtOAc/hexanes) provided 2.43 g of 7t. $^{13}$C NMR (DMSO, d$_6$, 90° C.) δ 25.9, 27.7, 29.1, 31.3, 34.6, 37.8, 42.3, 49.8, 60.2, 77.8, 125.2, 127.6, 128.4, 139.5, 153.7 ppm. Mass spectrum [ESI], [(M+H)$^+$]=334.

Step 7

To a solution of alcohol 7t (2.43 g) in 20 mL of anhydrous pyridine at 0° C. was added p-toluenesulfonyl chloride (2.1 g). The reaction mixture was then slowly warmed to room temperature and stirred for 5 hours. The resulting solution was concentrated in vacuo and poured into a large volume of ether. The organic layer was washed successively with 1 N HCl (3 repetitions), saturated NaHCO$_3$ and brine. The resulting solution was dried over magnesium sulfate, filtered and concentrated in vacuo. The remaining oil was purified using flash chromatography (silica, 0–25% EtOAc/hexanes) to give 2.86 g of 8t. $^{13}$C NMR (CDCl$_3$) δ 21.6, 25.8, 26.2, 28.4, 31.8, 32.5, 35.9, 37.8, 43.4, 49.7, 70.2, 79.2, 126.0, 127.8, 128.2, 129.0, 129.8, 133.1, 139.9, 144.7, 154.8 ppm. Mass spectrum [ESI], [(M+H)$^+$]=488.

Step 8

To a solution of tosylate 8t in 30 mL of anhydrous DMSO was added sodium azide (1.9 g). The resulting slurry was stirred for 18 hours. The reaction mixture was diluted with a partially saturated mixture of sodium chloride and then poured into ether. The aqueous layer was then extracted with ether (three repetitions). The combined organic layer was washed with a partially saturated solution of sodium chloride. The remaining organic layer was dried over magnesium sulfate, filtered and concentrated in vacuo. Purification by flash chromatography (silica, 0–10% EtOAc/hexanes) provided 1.95 g of 9t. $^{13}$C NMR (CDCl$_3$) δ 25.6, 27.5, 28.5, 31.7, 32.6, 35.6, 38.5, 43.5, 49.9, 51.1, 79.4, 126.0, 128.2, 129.1, 140.0, 154.9 ppm. Mass spectrum [NH$_3$/CI], (M+H)$^+$=359.

Step 9

A solution of azide 9t in ethyl acetate (30 mL) was treated with 10% palladium on carbon (0.500 g) and stirred under an atmosphere of hydrogen gas for two hours. Filtration through celite and concentration in vacuo gave crude amine 10t.

Step 10

To a 0° C. solution of crude amine 10t (1.3 g) in THF (30 mL) was added 3-cyanophenyl isocyanate (4.08 mmol) dropwise in 5 mL of THF. Concentration in vacuo followed by flash chromatography provided 1.35 g of 11t. $^{13}$C NMR (CDCl$_3$) δ 14.1, 22.6, 25.3, 28.2, 28.5, 31.5, 31.8, 32.3, 35.4, 39.5, 40.2, 43.3, 49.8, 80.3, 112.6, 118.9, 121.4, 122.6, 125.3, 126.0, 128.3, 129.0, 129.7, 139.7, 140.7, 155.3, 155.9 ppm. Mass spectrum [ESI], [(M+Na)$^+$]=499.

Step 11

Urethane 11t (1.3 g) was dissolved in 25 mL of 4M HCl in dioxane and stirred for 2 hours. The resulting solution was concentrated in vacuo to provide 1.17 g of 12t. $^{13}$C NMR (CDCl$_3$) δ 14.1, 22.6, 25.5, 26.1, 30.7, 31.1, 31.5, 36.7, 38.7, 40.3, 51.8, 112.9, 118.6, 121.5, 123.3, 125.7, 126.6, 128.6, 128.7, 128.9, 130.1, 139.1, 140.7, 157.7 ppm. Mass spectrum [ESI], [(M+H)$^+$]=377.

Resolution 1

The enantiomers of 12t can be resolved by HPLC using the following conditions.

Mixture A: 98% acetonitrile, 1% ethanol, 0.9% methanol, 0.1% diethyl amine; Mixture B: 50% ethanol, 50% methanol; Eluting solvent mixture: 94% Mixture A: 6% Mixture B; Flow rate: 1 mL/min; Injection solvent: 94% Mixture A: 6% Mixture B; Column: Chiral Pak AD (4.6 mm×250 mm)

The hydrogen chloride salt of (+) and (−)-12t can be regenerated by dissolving the respective free base in CH$_2$Cl$_2$ and adding one equivalent of 1N HCl in ether. The resulting solution can be concentrated in vacuo to provide (+)-12t ([α]$_D^{25}$=+8.6°, c=0.488, CH$_3$OH) and (−)-12t ([α]$_D^{25}$=−7.20, c=0.426, CH$_3$OH).

EXAMPLE 2

(±)-cis-N-(3-cyanophenyl)-N'-{[3-(4-(benzyl)-2-piperidinyl]propyl}urea

Step 12

A deoxygenated ethanolic solution of an approximately 1:1 mixture of E and Z—6 (0.072 g) was charged with 0.026 g of 10% Pd on carbon and allowed to stir under an atmosphere 1.5:1 mixture of 7c and 7t, respectively.

SCHEME 11

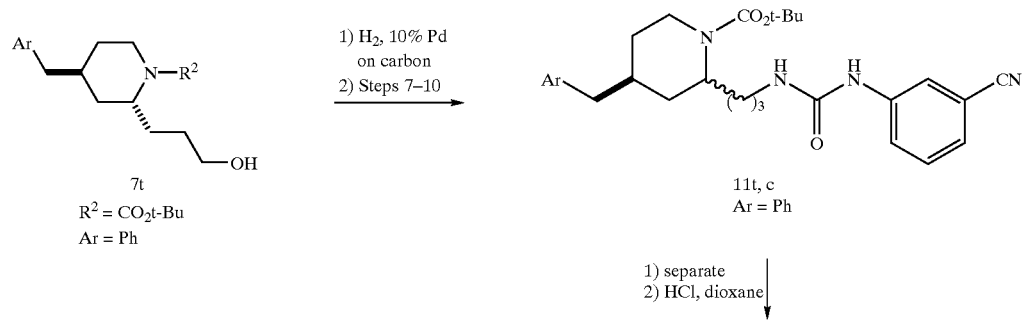

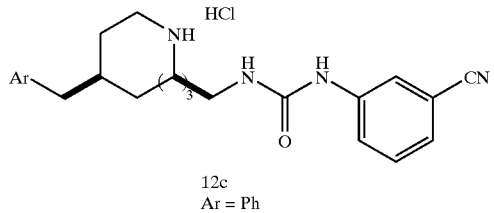

12c
Ar = Ph of hydrogen gas for 12 hours. Filtration through celite and concentration in vacuo provided 0.065 g of an approximately Conversion of this mixture of alcohols using steps 7–10 from example 1 provided an approximately 1.5:1 mixture of 11c and 11t, respectively (Scheme 11.)

Separation 1

Separation of 11c and 11t could be accomplished by high performance liquid chromatography (column: silica; [41.5 mm (diameter)×25 cm (length)]; solvent: 1% methanol/methylene chloride; flow rate: 45 mL/min; detector wavelength: 260 nm). Retention time: 11c=24.6 minutes, 11t=27.3 minutes.

Step 13

To a 0° C. solution of 11c in 2 mL of $CH_2Cl_2$ was added dropwise 2 mL of TFA. Concentration in vacuo after 2 hours provided 12c. Mass spectrum [ESI], $[(M+H)^+]$=377.

EXAMPLE 3

(±)-trans-N-(3-cyanophenyl)-N'-[3-[4-(4-fluorobenzyl)-2-piperidinyl]propyl urea

The above compound was prepared by substituting 4-fluoro benzyltriphenyl phosphonium chloride in step 4 (example 1), then performing step 5, step 12, steps 7–10, separation 1 and step 12. Mass spectrum [ESI], $[(M+H)^+]$=395.

EXAMPLE 4

(±)-trans-N-(3-cyanophenyl)-N'-[3-[4-(4-benzyl)-1-methyl-2-piperidinyl]propyl urea To a solution of (±)-12t (0.006 g) in 1 mL of 1,2-dichloroethane was added a drop of formaldehyde and 0.050 g of of crushed 4 Å molecular sieves. After stirring for 15 minutes, an excess (0.050 g) of sodium triacetoxyborohydride was added and the mixture stirred for an additional 12 hours. The reaction mixture was then quenched by the addition of 1 N NaOH and poured into EtOAc. The resulting organic layer was dried over magnesium sulfate filtered and concentrated in vacuo. Purification by reverse phase chromatography provided the TFA salt of the above compound. Mass spectrum [ESI], $[(M+H)^+]$=391.

EXAMPLE 5

(±)-trans-N-(3-cyanophenyl)-N'-[3-[4-(4-benzyl)-1-acetyl-2-piperidinyl]propyl urea To a solution of (±)-12t (0.006 g) in 1 mL of $CH_2Cl_2$ was added an excess (0.050 mL) of acetic anhydride and triethyl amine (0.050 mL). After stirring for 15 minutes the solution was poured into EtOAc and washed with 1 N HCl, saturated $NaHCO_3$ and brine. The organic layer was dried over magnesium sulfate, filtered, and concentrated in vacuo. Purification by flash chromatography (0–4% $CH_2Cl_2$/MeOH) provided the above compound. Mass spectrum [ESI], $[(M+H)^+]$=419.

EXAMPLE 47

N-(3-acetylphenyl)-N'-{[3-(2S, 4R)-4-(4-fluorobenzyl)piperidinyl]propyl}urea

Ketone 17 (the S-enantiomer of ketone 4, see Scheme 9) can be prepared by a slight modification of the procedure described in Example 1.

To a −23° C. solution of 2-tri-1-propylsilyl-3-methoxy pyridine (65.5 g, 247 mmol) in 1.5 mL of toluene and 400 mL of anhydrous THF was added 1.7 L of a 0.16 M solution of B in toluene. The resulting solution was stirred for 2 h and then cooled to −78° C. To this solution was added dropwise 247 mL of a 2 M THF solution of allyl magnesium chloride. After stirring for 1 h at this temperature the reaction was quenched with 3 L of 1 N HCl and stirred at room temperature for 12 h. After separating the two phases, the aqueous layer was washed with $Et_2O$ and combined with the original organic layer. This combined layer was washed with brine and dried over magnesium sulfate. Concentration, chromatography (silica, 5% EtOAc/hexanes) and recrystalization from hot hexanes provided enone 13.

SCHEME 12

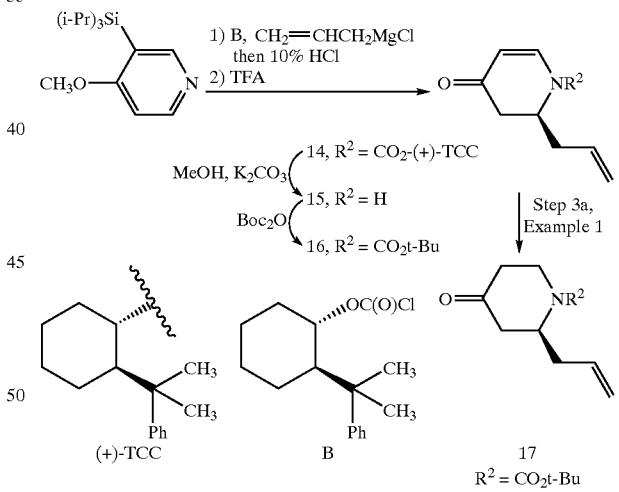

Enone 13 was dissolved in 360 mL of a 75% solution of TFA in $CH_2Cl_2$ and stirred for 10 h. Concentration, reconcentration from methanol and chromatography (silica, 20% EtOAc/hexanes) of the residue provided enone 14.

To a solution of enone 14 in 1 L of methanol was added 70 g of potassium carbonate. After stirring for 4 h at reflux, the reaction was cooled to room temperature, concentrated, slurried in EtOAc and filtered. The resulting solution was concentrated and the residue chromatographed (silica, 20% MeOH/EtOAc) to provide vinylogous amide 15.

To a solution of amide 15 (30 g) in 1 L of acetonitrile was added DMAP (35.4 g) and $Boc_2O$. After stirring for 12 h, the reaction mixture was concentrated and diluted with EtOAc. The resulting solution was washed with 1 N HCl, saturated NaHCO$_3$ and brine. The remaining solution was then dried over magnesium sulfate, filtered, and concentrated in vacuo. Purification by flash chromatography (20% EtOAc/hexanes) provided enone 16. Reduction of enone 16 using the method described in Example 1, Step 3a provided ketone 17. Mass spectrum [NH$_3$/CI], [(M+H)$^+$]=240; ([α]$_D^{25}$=+36.9°, c=0.396, CH$_3$OH); $^{13}$C NMR (CDCl$_3$) δ 28.3, 37.2, 38.4, 40.5, 44.5, 51.6, 80.4, 118.1, 133.5, 154.6, 208.0 ppm.

To a −78° C. solution of A (65 g, 121 mmole, see Scheme 14) in 250 mL of THF was added dropwise 241 mL of a 1M KOt-Bu solution (Scheme 13). After complete addition of the base the reaction mixture was slowly warmed to room temperature

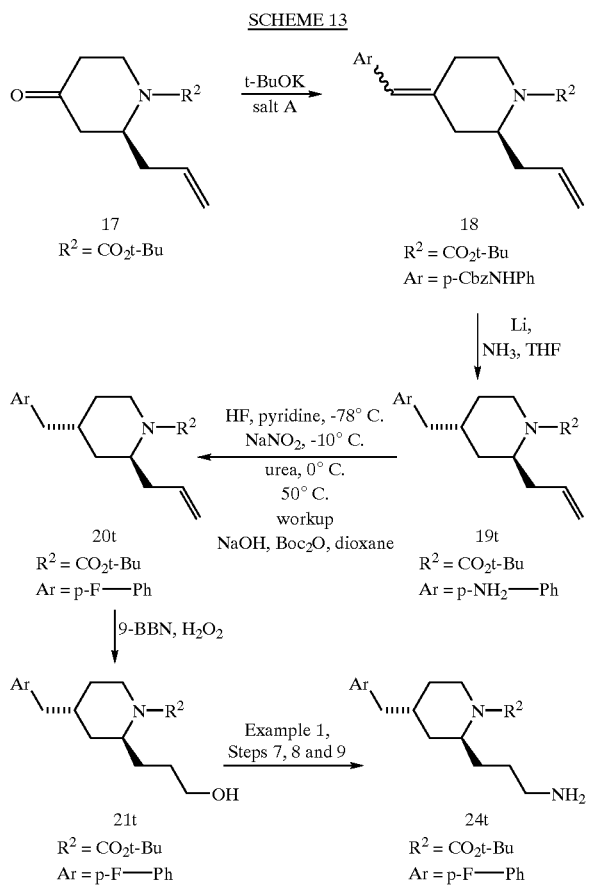

SCHEME 13 and stirred for 1 h. Ketone 17 (17 g, 17 mmole) was then added dropwise in 50 mL of THF and the solution stirred until the complete disappearance of starting ketone. The reaction mixture was quenched by the addition of 1N HCl. The organic layer was washed with saturated NaHCO$_3$ and brine. The remaining solution was then dried over magnesium sulfate, filtered, and concentrated in vacuo. Purification by flash chromatography (0–20% EtOAc/hexanes) provided a mixture of olefins 18 (Scheme 13.)

Reduction of this mixture of olefins 18 according to the conditions described in Example 1, Step 6 provided olefin 19t. To a −78° C. solution of 70% HF/pyridine (39 mL) was slowly added a solution of 19t (13.4 g, 40.4 mmole) in 13 mL of pyridine. The resulting solution was allowed to stabilize at −30° C. (internal temperature) after which sodium nitrite (5.6 g, 81 mmole) was added in one portion. The reaction mixture was allowed to stir at −10° C. for 30 min after which 4.9 g of urea was added and the temperature allowed to rise to 0° C. After stirring for 30 min, the temperature was raised to 50° C. and the mixture stirred until all signs of gas evolution had ceased.

After cooling to 0° C. the reaction was quenched by the careful addition of 1 N NaOH and then diluted with a large portion of EtOAc. The resulting aqueous layer was exhaustively extracted with additional EtOAc. The combined organic layers were concentrated in vacuo and dissolved in dioxane (80 mL). To this solution was added Boc$_2$O (13.2 g) and 1 N NaOH (60 mL). After stirring for 1 h the reaction mixture was concentrated and dissolved in Et$_2$O. The organic layer was washed with saturated NaCl. This solution was then dried over magnesium sulfate, filtered, and concentrated in vacuo. Purification by flash chromatography (0–10% EtOAc/hexanes) provided 20t. Hydroboration of 20t using the conditions described in Example 1, Step 5 provided alcohol 21t. Preparation of the amine via the tosylation, azide displacement and reduction protocol provided amine 25t. For amine 25t ([α]$_D^{25}$=+29.2°, c=0.896, CH$_3$OH); $^{13}$C NMR (CDCl$_3$) δ 27.8, 28.5, 30.5, 32.0, 32.6, 35.3, 38.5, 42.0, 42.7, 50.3, 79.2, 115.0, 130.3, 135.7, 155.0, 161.3 ppm. To a 0° C. solution of amine 25t (4 mmol) in THF (20 mL) was added 3-acetylphenyl isocyanate (0.562 mL). Concentration in vacuo followed by flash chromatography (silica, 0–60% EtOAc/hexanes) provided crude 26t. To a solution of 26t in 5 mL of CH$_2$Cl$_2$ was added 15 mL of trifluoroacetic acid. After stirring for 2 h the solution was concentrated and then reconcentrated from methanol (10 mL). Purification using flash chromatography (silica, 0–12% methanol/CH$_2$Cl$_2$/NH$_4$OH, lower layer) provided Example 47. ([α]$_D^{25}$=+5.7°, c=0.474, CH$_3$OH); $^{13}$C NMR (CDCl$_3$) δ 25.4, 25.6, 26.4, 28.1, 30.9, 31.2, 37.8, 38.6, 39.3, 51.7, 114.7, 118.2, 121.9, 123.2, 128.7, 130.2, 135.4, 137.5, 140.2, 156.7, 161.5, 199.1 ppm.

Salt A

To 23 mL of benzyl alcohol (222 mmol) was added a small piece of lithium metal (8 mg). The solution was heated with vigorous stirring until all of the metal was consumed and then allowed to cool to room temperature. The resulting solution was diluted with 800 mL of diethyl ether after which a solution of p-chloromethylphenyl isocyanate (34 g, 202 mmol) in 200 mL of EtOAc was added over 5 min. The resulting reaction mixture was stirred for 12 h and then quenched by

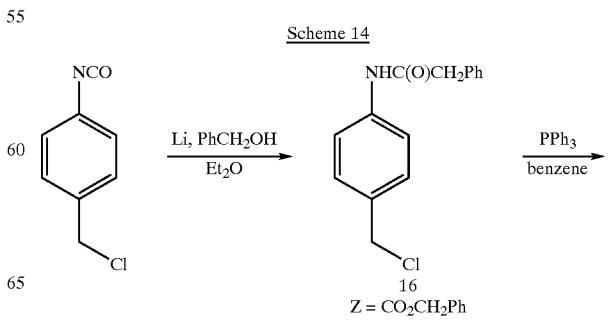

Scheme 14

-continued

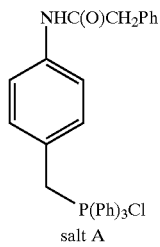
salt A the addition of water. The organic layer was washed with saturated NaCl, dried over magnesium sulfate, filtered, and concentrated in vacuo. The resulting solid was washed with generous portions of hexanes and used without further purification. To a slurry of the resulting chloride in benzene (250 mL) was added triphenyl phosphine (160 g). This mixture was heated for 12 h at reflux and then cooled to room temperature. Filtration provided phosphonium salt A which was used without further purification.

EXAMPLE 48
N-(3-acetylphenyl)-N'-{[3-(2S, 4R)-4-(4-fluorobenzyl)1-propylpiperidinyl]propyl}urea To a solution of the compound prepared in Example 47 (0.077 g) in 2 mL of $CH_2Cl_2$ was added 0.140 mL of a 1 M solution of HCl in diethyl ether. The mixture was diluted with 5 mL of hexane and concentrated. The precipitate was dissolved in 5 mL of 1,2-dichloroethane and charged with 0.022 g of propionaldehyde and 0.053 g of sodium triacetoxy borohydride, respectively. After stirring for 30 min. the reaction was quenched with 0.100 mL of 1N NaOH and concentrated. Purification using flash chromatography (silica, 0–3% methanol/$CH_2Cl_2$/$NH_4OH$, lower layer) provided Example 48. $^{13}C$ NMR ($CDCl_3$) δ 11.3, 18.7, 23.1, 26.9, 28.3, 30.8, 31.1, 39.8, 41.0, 47.8, 55.4, 59.4, 115.8, 119.2, 123.5, 124.9, 130.3, 131.6, 136.7, 138.5, 141.1, 157.6, 162.2, 202.0 ppm.

EXAMPLE 65
N"-cyano-N-(3,5-diacetylphenyl)-N'-{3-[(2S,4R)-4-(4-fluorobenzyl)-1-(2-hydroxyethyl)piperidinyl]propyl}guanidine To a slurry of 3,5-diacetyl aniline (20 g) (see P. Ulrich, *J. Med. Chem.*, 1984, 27, 35–40 for the preparation of this substance) in acetonitrile (150 mL) was added diphenyl-cyanocarbonimidate (26.9 g). The resulting mixture was heated at reflux for 6 h and allowed to cool to room temperature. The resulting soild was filtered, washed with hexanes and used without further purification.

To a solution of amine 24t (0.617 g) in 35 mL of isopropanol was added 0.680 g of the above reagent. The reaction was heated at reflux for 6 h, cooled to room temperature, concentrated and purified by flash chromatography to provide 0.532 g of the resulting cyanoguanidine.

To a solution of the cyanoguanidine (0.532 g) in 5 mL of methylene chloride was added 5 mL of 4N HCl in dioxane at room temperature. After 1 h the reaction mixture was concentrated and purified by flash chromatography (silica, 0–10% methanol/$CH_2Cl_2$/$NH_4OH$, lower layer) to provide 0.334 g of Example 65.

The following table (Table 1) contains examples of the present invention, which may be prepared by procedures described herein, or methods familiar to one skilled in the art.

TABLE 1
Core
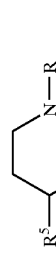
Linkers X-Y
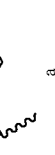 a
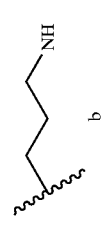 b
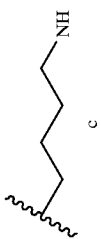 c
| EXAMPLE | NAME | STEREOCHEMISTRY | X-Y | R⁵ | R | R¹ | MASS SPECTRA (ESI) |
|---|---|---|---|---|---|---|---|
| 6 | (±)-cis-N-{3-[4-benzyl-2-piperidinyl]propyl}-N'-(3-cyanophenyl)urea | cis | b | H | benzyl | 3-cyanophenyl-NH-C(O)-NH- | [M + H]⁺ = 377.5 |
| 7 | (±)-trans-N-(3-cyanophenyl)-N'-[2-[4-(benzyl)-2-piperidinyl]ethyl] urea | trans | a | H | benzyl | 3-cyanophenyl-NH-C(O)-NH- | [M + H]⁺ = 363.48 |

TABLE 1-continued

| | | | | | |
|---|---|---|---|---|---|
| 8 | (±)-trans-N-{3-[4-benzyl-2-piperidinyl]propyl}-3-cyanobenzamide | trans | b | H | [M + H]⁺ = 362.49 |
| 9 | (±)-trans-N-(3-acetylphenyl)-N'-{2-[4-(benzyl)-2-piperidinyl]ethyl} urea | trans | a | H | [M + H]⁺ = 380.51 |
| 10 | (±)-trans-N-{3-[4-benzyl-2-piperidinyl]propyl}-4-fluorobenzenesulfonamide | trans | b | H | [M + H]⁺ = 391.52 |
| 11 | (±)-trans-N-{3-[4-benzyl-2-piperidinyl]propyl} benzamide | trans | b | H | [M + H]⁺ = 337.48 |
| 12 | (±)-cis-N-(3-cyanophenyl)-N'-{3-[4-(4-fluorobenzyl)-2-piperidinyl]propyl} urea | cis | b | H | [M + H]⁺ = 395.5 |

TABLE 1-continued

| | | | | | |
|---|---|---|---|---|---|
| 13 | (±)-trans-N-(3-acetylphenyl)-N'-[3-[4-(4-fluorobenzyl)-2-piperidinyl]propyl]urea | trans | 4-fluorobenzyl | H | 3-acetyl-N-acetyl-anilide | $[M + H]^+ = 412.52$ |
| 14 | (±)-cis-N-(3-acetylphenyl)-N'-[3-[4-(4-fluorobenzyl)-2-piperidinyl]propyl]urea | cis | 4-fluorobenzyl | H | 3-acetyl-N-acetyl-anilide | $[M + H]^+ = 412.52$ |
| 15 | (±)-trans-N-(3-chlorophenyl)-N'-[3-[4-(benzyl)-2-piperidinyl]propyl]urea | trans | benzyl | H | 3-chloroacetanilide | $[M + H]^+ = 386.94$ |
| 16 | (±)-trans-N-(phenyl)-N'-[3-[4-(benzyl)-2-piperidinyl]propyl]urea | trans | benzyl | H | acetanilide | $[M + H]^+ = 352.5$ |
| 17 | (±)-trans-N-(3-fluorophenyl)-N'-[3-[4-(benzyl)-2-piperidinyl]propyl]urea | trans | benzyl | H | 3-fluoroacetanilide | $[M + H]^+ = 387.56$ |
| 18 | (±)-trans-N-(3-methoxyphenyl)-N'-[3-[4-(benzyl)-2-piperidinyl]propyl]urea | trans | benzyl | H | 3-methoxyacetanilide | $[M + H]^+ = 382.52$ |
| 19 | (±)-trans-N-(4-carboethoxyphenyl)-N'-[3-[4-(benzyl)-2-piperidinyl]propyl]urea | trans | benzyl | H | 4-CO2Et-acetanilide | $[M + H]^+ = 424.56$ |

TABLE 1-continued

| | | | | | |
|---|---|---|---|---|---|
| 20 | (±)-trans -N-(4-fluorophenyl)-N'-[3-[4-(benzyl)-2-piperidinyl]propyl urea | trans | b | H | [M + H]⁺ = 370.49 |
| 21 | (±)-trans-N-(3-acetylphenyl)-N'-[3-[4-(benzyl)-2-piperidinyl]propyl urea | trans | b | H | [M + H]⁺ = 394.53 |
| 22 | (±)-trans-N-(3-trifluoromethylphenyl)-N'-[3-[4-(benzyl)-2-piperidinyl]propyl urea | trans | b | H | [M + H]⁺ = 420.49 |
| 23 | (±)-cis-N-(3-cyanophenyl)-N'-[3-[4-(benzyl)-1-propyl-2-piperidinyl]propyl urea | cis | b | CH2CH2CH3 | [M + H]⁺ = 419.59 |
| 24 | (±)-trans-N-(3-acetylphenyl)-N'-[3-[4-(benzyl)-1-propyl-2-piperidinyl]propyl urea | trans | b | CH2CH2CH3 | [M + H]⁺ = 436.61 |
| 25 | (±)-cis-N-(3-acetylphenyl)-N'-[3-[4-(4-fluorobenzyl)-1-propyl-2-piperidinyl]propyl urea | cis | b | CH2CH2CH3 | [M + H]⁺ = 454.6 |

TABLE 1-continued

| | | | | | |
|---|---|---|---|---|---|
| 26 | (±)-trans-N-(3-acetylphenyl)-N'-[3-[4-(4-fluorobenzyl)-1-propyl-2-piperidinyl]propyl urea | trans | 4-fluorobenzyl (b) | CH2CH2CH3 | 3-acetamidophenyl | [M + H]+ = 454.6 |
| 27 | (±)-trans-N-[2-[4-benzyl-2-piperidinyl]ethyl]-4-fluorobenzenesulfonamide | trans | benzyl (a) | H | 4-fluorophenylsulfonyl | [M + H]+ = 377.5 |
| 28 | (±)-trans-N-[2-[4-benzyl-2-piperidinyl]ethyl]-3-chlorobenzesulfonamide | trans | benzyl (a) | H | 3-chlorophenylsulfonyl | [M + H]+ = 393.95 |
| 29 | (±)-trans-N-[2-[4-benzyl-2-piperidinyl]ethyl]-3-cyanobenzamide | trans | benzyl (a) | H | 3-cyanobenzoyl | [M + H]+ = 348.46 |
| 30 | (±)-trans-N-(3-cyanophenyl)-N'-[4-[4-(benzyl)-2-piperidinyl]butyl urea | trans | benzyl (c) | H | 3-cyanophenylaminocarbonyl | [M + H]+ = 391.53 |
| 31 | (±)-trans-N-(3-acetylphenyl)-N'-[4-[4-(benzyl)-2-piperidinyl]butyl urea | trans | benzyl (c) | H | 3-acetamidophenylaminocarbonyl | [M + H]+ = 408.56 |

TABLE 1-continued

| | | | | | |
|---|---|---|---|---|---|
| 32 | N-(3-acetylphenyl)-N'-{[3-[2S,4S]-4-(4-fluorobenzyl)piperidinyl]propyl}urea | 2S, 4S | b | H | [M + H]⁺ = 412.518 |
| 33 | N-(3-acetylphenyl)-N'-{[4-[2R,4R]-4-(4-fluorobenzyl)-2-piperidinyl]butyl}urea | 2R, 4R | c | H | [M + H]⁺ = 426.545 |
| 34 | N-(3-cyanophenyl)-N'-{[4-[2R,4R]-4-(4-fluorobenzyl)piperidinyl]butyl}urea | 2R, 4R | c | H | [M + H]⁺ = 409.518 |
| 35 | N-(3-acetylphenyl)-N'-{3-[(2S,4R)-4-(2,4-difluorobenzyl)piperidinyl]propyl}urea | 2S, 4R | b | H | [M + H]⁺ = 430.508 |
| 36 | N-{3-[(2S,4R)-1-allyl-4-(4-fluorobenzyl)piperidinyl]propyl}-N'-(3,5-diacetylphenyl)urea | 2S, 4R | b | CH2CHCH2 | [M + H]⁺ = 494.619 |

TABLE 1-continued

| | | | | | [M + H]+ |
|---|---|---|---|---|---|
| 37 | N-(3,5-diacetylphenyl)-N'-{3-[(2S,4R)-4-(4-fluorobenzyl)piperidinyl]propyl}urea | 2S, 4R | b | CH2CH2OH | 498.607 |
| 38 | N-{3-[(2S,4R)-1-acetyl-4-(4-fluorobenzyl)piperidinyl]propyl}-N'-(3,5-diacetylphenyl)urea | 2S, 4R | b | C(O)CH3 | 496.592 |
| 39 | N-(3,5-diacetylphenyl)-N'-{3-[(2S)-4-(4-fluorobenzyl)-1-(2-fluoroethyl)piperidinyl]propyl}urea | 2S, 4R | b | CH2CH2F | 500.599 |
| 40 | (±)-trans-N-(3-acetylphenyl)-N'-[3-[4-(benzyl)-1-(2-hydroxyethyl)-2-piperidinyl]propyl]urea | trans | b | CH2CH2OH | 438.59 |
| 41 | (±)-trans-N-(3-acetylphenyl)-N'-[3-[4-(benzyl)-1-methyl-2-piperidinyl]propyl]urea | trans | b | CH3 | 408.56 |

TABLE 1-continued

| # | Name | Stereo | b | R | Ar | [M+H]+ |
|---|------|--------|---|---|-----|--------|
| 42 | (±)-trans-N-(3-acetylphenyl)-N'-[3-[4-(benzyl)-1-ethyl-2-piperidinyl]propyl] urea | trans | b | CH2CH3 | phenyl | 422.59 |
| 45 | N-(3-acetylphenyl)-N'-{[3-(2R,4R)-4-(4-fluorobenzyl)piperidinyl]propyl} urea | 2R, 4R | b | H | 4-fluorophenyl | 412.518 |
| 46 | N-(3-acetylphenyl)-N'-{[3-(2S,4R)-4-(4-fluorobenzyl)piperidinyl]propyl} urea | 2S, 4R | b | H | 4-fluorophenyl | 412.518 |
| 47 | N-(3-acetylphenyl)-N'-{[3-(2S,4R)-4-(4-fluorobenzyl)1-propylpiperidinyl]propyl} urea | 2S, 4R | b | CH2CH2CH3 | 4-fluorophenyl | 454.598 |
| 48 | N-(3-acetylphenyl)-N'-{[3-(2S,4R)-4-(4-fluorobenzyl)1-methylpiperidinyl]propyl} urea | 2S, 4R | b | CH3 | 4-fluorophenyl | 426.545 |

TABLE 1-continued

| | | | | | |
|---|---|---|---|---|---|
| 49 | N-(3-acetylphenyl)-N'-{[3-(2S,4R)-4-(4-fluorobenzyl)-1-(2-hydroxyethyl)piperidinyl]propyl} urea | 2S, 4R | b (4-fluorobenzyl) | CH2CH2OH | 3-acetylphenyl acetamide; $[M+H]^+ = 456.571$ |
| 50 | [(2S,4R)-2-(3-{[(3-acetylanilino)carbonyl]amino}propyl)-4-(4-fluorobenzyl)piperidinyl] acetic acid | 2S, 4R | b (4-fluorobenzyl) | CH2CO2H | 3-acetylphenyl acetamide; $[M+H]^+ = 470.554$ |
| 51 | N-(3-acetylphenyl)-N'-{3-[(2S,4R)-1-benzyl-4-(4-fluorobenzyl)piperidinyl]propyl}urea | 2S, 4R | b (4-fluorobenzyl) | benzyl | 3-acetylphenyl acetamide; $[M+H]^+ = 502.642$ |
| 52 | (±)-trans-N-{3-[(4-benzyl-2-piperidinyl]propyl}-N'-(3-fluoro-4-methylphenyl)urea | trans | b (benzyl) | H | 3-fluoro-4-methylphenyl acetamide; $[M+H]^+ = 384.508$ |
| 53 | (±)-trans-N-{3-[4-benzyl-2-piperidinyl]propyl}-N'-(3,4-dimethoxyphenyl)urea | trans | b (benzyl) | H | 3,4-dimethoxyphenyl acetamide; $[M+H]^+ = 412.543$ |
| 54 | (±)-trans-N-{3-[4-benzyl-2-piperidinyl]propyl}-N'-(6-methoxy-3-pyridinyl)urea | trans | b (benzyl) | H | 6-methoxy-3-pyridinyl acetamide; $[M+H]^+ = 383.505$ |

TABLE 1-continued

| | | | | | |
|---|---|---|---|---|---|
| 55 | (±)-trans-N-{3-[4-benzyl-2-piperidinyl]propyl}-N'-(1H-indazol-6-yl)urea | trans | b | benzyl | H | indazol-6-yl | [M + H]⁺ = 392.516 |
| 56 | N-(3-acetylphenyl)-N'-{3-[(2S,4R)-1-(cyclopropylmethyl)-4-(4-fluorobenzyl)piperidinyl]propyl}urea | 2S, 4R | b | 4-fluorobenzyl | cyclopropylmethyl | 3-acetylphenyl | [M + H]⁺ = 466.609 |
| 57 | N-(3-cyanophenyl)-N'-{3-E(2S,4R)-4-(4-fluorobenzyl)piperidinyl]propyl}urea | 2S, 4R | b | 4-fluorobenzyl | H | 3-cyanophenyl | [M + H]⁺ = 395.491 |
| 58 | N-(3-cyanophenyl)-N'-{3-[(2S,4R)-4-(4-fluorobenzyl)-1-propylpiperidinyl]propyl}urea | 2S, 4R | b | 4-fluorobenzyl | CH2CH2CH3 | 3-cyanophenyl | [M + H]⁺ = 437.572 |
| 59 | N-(3-acetylphenyl)-N'-{3-[(2S,4R)-1-allyl-4-(4-fluorobenzyl)piperidinyl]propyl}urea | 2S, 4R | b | 4-fluorobenzyl | CH2CHCH2 | 3-acetylphenyl | [M + H]⁺ = 452.583 |
| 60 | N-{3-[(2S,4R)-4-(4-fluorobenzyl)piperidinyl]propyl}-N'-[3-(1-methyl-1H-tetraazol-5-yl)phenyl]urea | 2S, 4R | b | 4-fluorobenzyl | H | 3-(1-methyl-1H-tetraazol-5-yl)phenyl | [M + H]⁺ = 452.547 |

TABLE 1-continued

| | | | | | |
|---|---|---|---|---|---|
| 61 | N-{3-[(2S,4R)-4-(4-fluorobenzyl)-1-propylpiperidinyl]propyl}-N'-[3-(1-methyl-1H-tetraazol-5-yl)phenyl]urea | 2S, 4R | b | CH2CH2CH3 | 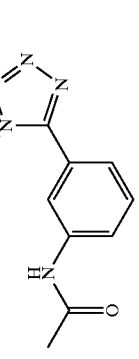 [M + H]⁺ = 494.627 |
| 62 | (2S,4R)-2-(3-{[(E)-amino(oxo)methyl]imino}(3,5-diacetylanilino)methyl amino)propyl)-4-(4-fluorobenzyl)-N-methyl-1-piperidinecarboxamide | 2S, 4R | b | C(O)NHCH3 | 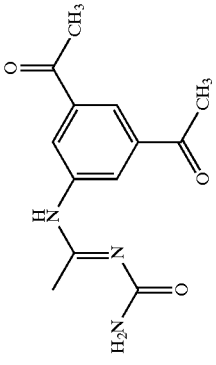 [M + H]⁺ = 553.647 |
| 63 | N-[(E)-({3-[(2S,4R)-1-acetyl-4-(4-fluorobenzyl)piperidinyl]propyl}amino)(3,5-diacetylanilino)methylidene]urea | 2S, 4R | b | C(O)CH3 | 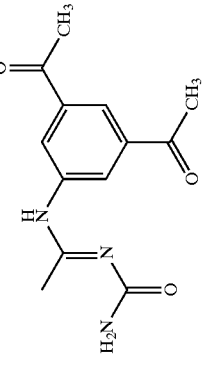 [M + H]⁺ = 538.632 |
| 64 | N''-cyano-N-(3,5-diacetylphenyl)-N'-{3-[(2S,4R)-4-(4-fluorobenzyl)-1-(2-hydroxyethyl)piperidinyl]propyl}guanidine | 2S, 4R | b | CH2CH2OH | 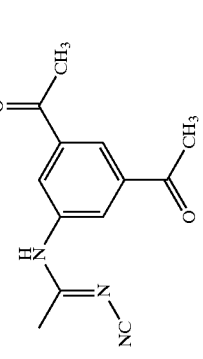 [M + H]⁺ = 522.633 |

TABLE 1-continued

| | | | | | [M + H]⁺ = |
|---|---|---|---|---|---|
| 65 | N-(3,5-diacetylphenyl)-N'-{3-[(2S,4R)-4-(4-fluorobenzyl)piperidinyl]propyl}urea | 2S, 4R | b | H | 454.555 |
| 66 | N-(3,5-diacetylphenyl)-N'-{3-[(2S,4R)-4-(4-fluorobenzyl)-1-propylpiperidinyl]propyl}urea | 2S, 4R | b | CH2CH2CH3 | 496.635 |
| 67 | N-[(E)-(3,5-diacetylanilino){3-[(2S,4R)-4-(4-fluorobenzyl)piperidinyl]propyl}aminomethylidene]urea | 2S, 4R | b | H | 496.596 |
| 68 | N''-cyano-N-(3,5-diacetylphenyl)-N'-{3-[(2S,4R)-4-(4-fluorobenzyl)piperidinyl]propyl}guanidine | 2S, 4R | b | H | 478.581 |

TABLE 1-continued

| | | | | | |
|---|---|---|---|---|---|
| 69 | (2S,4R)-2-(3-[[(3,5-diacetylanilino)carbonyl]amino]propyl)-4-(4-fluorobenzyl)-1-piperidinecarboximidamide | 2S, 4R | b | C(=NH)NH2 | [M + H]$^+$ = 496.596 |
| 70 | N''-cyano-N-(3,5-diacetylphenyl)-N'-{3-[(2S,4R)-4-(4-fluorobenzyl)-1-propylpiperidinyl]propyl}guanidine | 2S, 4R | b | CH2CH2CH3 | [M + H]$^+$ = 520.661 |
| 71 | (2S,4S)-2-(3-[[(3-acetylanilino)carbonyl]amino]propyl)-4-(4-fluorobenzyl)-1-piperidinecarboximidamide | 2S, 4R | b | C(=NH)NH2 | [M + H]$^+$ = 454.559 |
| 72 | N-{3-[(2S,4R)-1-(aminoacetyl)-4-(4-fluorobenzyl)piperidinyl]propyl}-N'-(3,5-diacetylphenyl)urea | 2S, 4R | b | C(O)CH2NH2 | [M + H]$^+$ = 511.607 |

TABLE 1-continued

| | | | | | [M + H]+ |
|---|---|---|---|---|---|
| 73 | N'-{3-[(2S,4R)-1-allyl-4-(4-fluorobenzyl)piperidinyl]propyl}-N''-cyano-N'-(3,5-diacetylphenyl)guanidine | 2S, 4R | b (4-fluorobenzyl) | CH2CHCH2 | 518.645 |
| 74 | N''-cyano-N-(3,5-diacetylphenyl)-N'-{3-[(2S,4R)-4-(4-fluorobenzyl)-1-(2-fluoroethyl)piperidinyl]propyl}guanidine | 2S, 4R | b (4-fluorobenzyl) | CH2CH2F | 524.625 |
| 75 | N''-cyano-N-(3,5-diacetylphenyl)-N'-{3-[(2S,4R)-4-(4-fluorobenzyl)-1-(2-propynyl)piperidinyl]propyl}guanidine | 2S, 4R | b (4-fluorobenzyl) | CH2CCH | 516.63 |
| 76 | N''-cyano-N-(3,5-diacetylphenyl)-N'-{3-[(2S,4R)-4-(4-fluorobenzyl)-1-methylpiperidinyl]propyl}guanidine | 2S, 4R | b (4-fluorobenzyl) | CH3 | 492.608 |

TABLE 1-continued

| | | | | | |
|---|---|---|---|---|---|
| 78 | N''-cyano-N-(3,5-diacetylphenyl)-N'-{3-[(2S,4R)-1-ethyl-4-(4-fluorobenzyl)piperidinyl]propyl}guanidine | 2S, 4R | b | CH2CH3 | $[M+H]^+ = 506.634$ |
| 79 | N-[3,5-bis(1-methyl-1H-tetraazol-5-yl)phenyl]-N'-{3-[(2S,4R)-4-(4-fluorobenzyl)piperidinyl]propyl}urea | 2S, 4R | b | H | $[M+H]^+ = 648.635$ |
| 80 | N-{3-[(2S,4R)-1-acetyl-4-(4-fluorobenzyl)piperidinyl]propyl}-N'-[3,5-bis(1-methyl-1H-tetraazol-5-yl)phenyl]urea | 2S, 4R | b | C(O)CH3 | $[M+H]^+ = 576.65$ |
| 81 | N-(3,5-diacetylphenyl)-N'-{3-[(2S)-4-(4-fluorobenzyl)-1-(2,2,2-trifluoroethyl)piperidinyl]propyl}urea | 2S, 4R | b | CH2CF3 | $[M+H]^+ = 536.579$ |

TABLE 1-continued

| | | | | | |
|---|---|---|---|---|---|
| 82 | N-(3,5-diacetylphenyl)-N'-{3-[(2S,4R)-1-(2,2-difluoroethyl)-4-(4-fluorobenzyl)piperidinyl]propyl}urea | 2S, 4R | b | CH2CHF2 | [M + H]⁺ = 518.589 |
| 83 | N-(3,5-diacetylphenyl)-N'-{3-[(2S,4R)-4-(4-fluorobenzyl)-1-(methylsulfonyl)piperidinyl]propyl}urea | 2S, 4R | b | SO2CH3 | [M + H]⁺ = 532.646 |
| 84 | N-(3,5-diacetylphenyl)-N'-{3-[(2S,4R)-4-(4-fluorobenzyl)-1-propionylpiperidinyl]propyl}urea | 2S, 4R | b | C(O)CH2CH3 | [M + H]⁺ = 510.618 |
| 85 | N-(3,5-diacetylphenyl)-N'-{3-[(2S,4R)-4-(4-fluorobenzyl)-1-isobutyrylpiperidinyl]propyl}urea | 2S, 4R | b | C(O)CH(CH3)2 | [M + H]⁺ = 524.645 |

TABLE 1-continued

| | | | | | |
|---|---|---|---|---|---|
| 86 | (2S,4R)-2-(3-{[(3,5-diacetylanilino)carbonyl]amino}propyl)-4-(4-fluorobenzyl)-N-methyl-1-piperidinecarboxamide | 2S, 4R | b | C(O)NHCH3 | 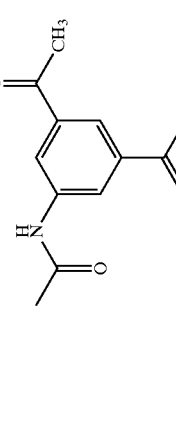 $[M + H]^+ = 511.607$ |
| 87 | (2S,4R)-2-(3-{[(3,5-diacetylanilino)carbonyl]amino}propyl)-4-(4-fluorobenzyl)-1-piperidinecarboxamide | 2S, 4R | b | C(O)NH2 | 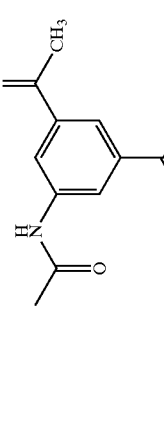 $[M + H]^+ = 497.58$ |
| 88 | N-(3,5-diacetylphenyl)-N'-{3-[(2S,4R)-4-(4-fluorobenzyl)-1-(2-pyridinylmethyl)piperidinyl]propyl}urea | 2S, 4R | b | 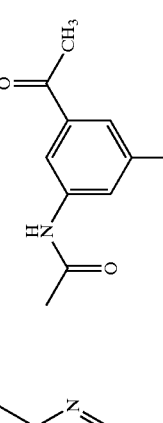 | $[M + H]^+ = 545.667$ |
| 89 | 2-[(2S,4R)-2-(3-{[(3,5-diacetylanilino)carbonyl]amino}propyl)-4-(4-fluorobenzyl)piperidinyl]acetamide | 2S, 4R | b | CH2C(O)NH2 | 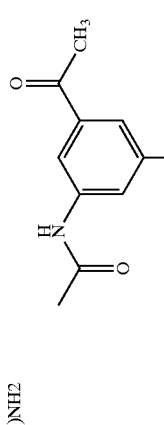 $[M + H]^+ = 511.607$ |

TABLE 1-continued

| | | | | | |
|---|---|---|---|---|---|
| 90 | N-{3-[(2S,4R)-1-[(2S)-2-aminopropanoyl]-4-(4-fluorobenzyl)piperidinyl]propyl}-N'-(3,5-diacetylphenyl)urea | 2S, 4R | b | | $[M + H]^+ = 525.633$ |
| 91 | N-{3-[(2S,4R)-1-[(2R)-2-aminopropanoyl]-4-(4-fluorobenzyl)piperidinyl]propyl}-N'-(3,5-diacetylphenyl)urea | 2S, 4R | b | | $[M + H]^+ = 525.633$ |
| 92 | N-(3,5-diacetylphenyl)-N'-{3-[(2S,4R)-4-(4-fluorobenzyl)-1-(2-propynyl)piperidinyl]propyl}urea | 2S, 4R | b | CH2CCH | $[M + H]^+ = 492.604$ |
| 93 | 1-(3-{[(E)-1-({3-[(2S)-4-(4-fluorobenzyl)piperidinyl]propyl}amino)-2-nitroethenyl]amino}phenyl)ethanone | 2S, 4R | b | H | $[M + H]^+ = 455.543$ |
| 94 | (±)-trans-N-{3-[4-(benzyl)-2-piperidinyl]propyl}-N'-[3-(phenylsulfonyl)phenyl]urea | trans | b | H | $[M + H]^+ = 492.653$ |

TABLE 1-continued

| | | | | |
|---|---|---|---|---|
| 95 | (±)-trans-N-{3-[4-(benzyl)-2-piperidinyl]propyl}-N'-[3-chloro-4-(diethylamino)phenyl]urea | trans | b | H | benzyl | 3-chloro-4-(diethylamino)phenyl-NHC(O)CH3 | [M + H]⁺ = 458.058 |
| 96 | (±)-trans-N-(3-{[({3-[4-benzyl-2-piperidinyl]propyl}amino)carbonyl]amino}phenyl)acetamide | trans | b | H | benzyl | 3-(acetamido)phenyl | [M + H]⁺ = 409.543 |
| 97 | (±)-trans-N-{3-[4-benzylpiperidinyl]-2-propyl}-N'-[3-(1-hydroxyethyl)phenyl]urea | trans | b | H | benzyl | 3-(1-hydroxyethyl)phenyl | [M + H]⁺ = 396.544 |
| 98 | (±)-trans-dimethyl 5-{[({3-[4-benzyl-2-piperidinyl]propyl}amino)carbonyl]amino}isophthalate | trans | b | H | benzyl | 3,5-bis(CO2CH3)phenyl | [M + H]⁺ = 468.563 |
| 99 | (±)-trans-ethyl 3-{[({3-[4-benzyl-2-piperidinyl]propyl}amino)carbonyl]amino}benzoate | trans | b | H | benzyl | 3-(CO2CH3)phenyl | [M + H]⁺ = 424.554 |
| 100 | (±)-trans-N-(3-[4-benzyl-2-piperidinyl]propyl}-N'-(3-chlorophenyl)urea | trans | b | H | benzyl | 3-chlorophenyl | [M + H]⁺ = 386.936 |

TABLE 1-continued

| | | | | | |
|---|---|---|---|---|---|
| 101 | N'-(3-5-diacetylphenyl)-N-{3-[(2S,4R)-4-(4-fluorobenzyl)-1-(2-oxopropyl)piperidinyl]propyl}urea | 2S, 4R | b | CH2C(O)CH3 | 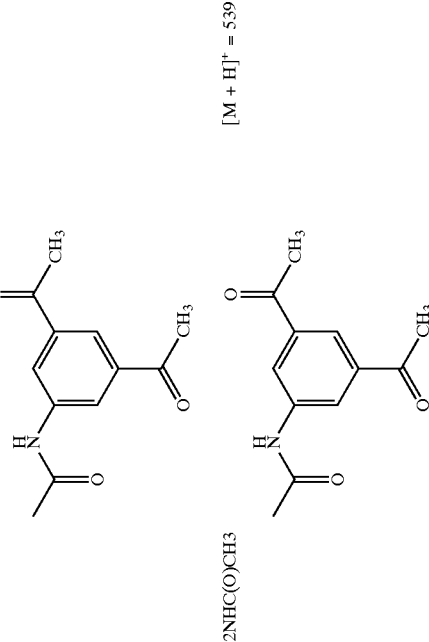 [M + H]+ = 510 |
| 102 | N-[3-(2-{3-[(3,5-diacetylanilinocarbonyl)amino]propyl}-1-piperidinyl)propyl]acetamide | 2S, 4R | b | CH2CH2NHC(O)CH3 | 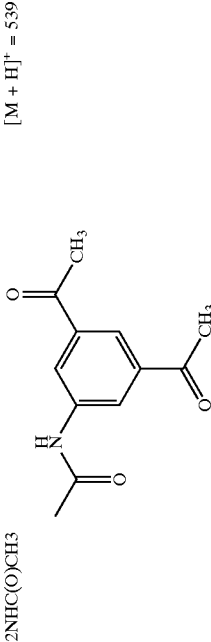 [M + H]+ = 539 |
| 103 | N-(3,5-diacetylphenyl)-N'-{3-[(2S,4R)-4-(4-fluorobenzyl)-1-(3-hydroxypropyl)piperidinyl]propyl}urea | 2S, 4R | b | CH2CH2CH2OH | 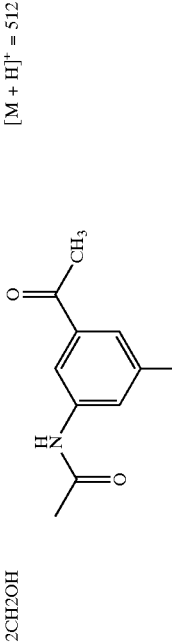 [M + H]+ = 512 |
| 104 | N''-cyano-N-(3,5-diacetylphenyl)-N'-{3-[(2S,4R)-4-(4-fluorobenzyl)-1-(2-oxopropyl)piperidinyl]propyl}guanidine | 2S, 4R | b | CH2C(O)CH3 | 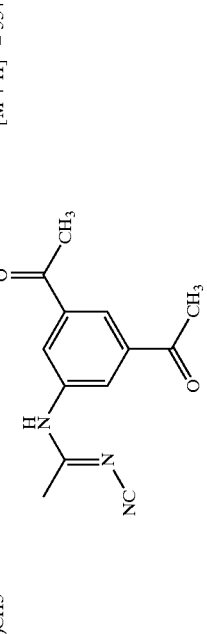 [M + H]+ = 534 |

TABLE 1-continued

| 105 | N''-cyano-N-(3,5-diacetylphenyl)-N'-{3-[(2S,4b)-4-(4-fluorobenzyl)-1-(3-hydroxypropyl)piperidinyl]propyl}guanidine | 2S, 4R | b | CH2CH2CH2OH | [structure] | [M + H]⁺ = 536 |

The following Table 2 contains additional representative examples of the present invention, and may be prepared by procedures described herein, or methods familiar to one skilled in the art. Each entry in the table is intended to be paired with each core and linker formulae at the top of the table. For example, Entry 1 in Table 2 is intended to be paired with Cores a–e, and X—Y linkers f–n.

TABLE 2*

Cores

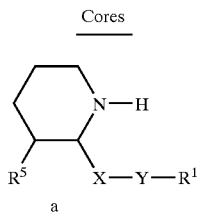
a

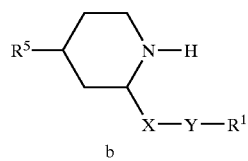
b

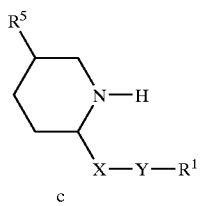
c

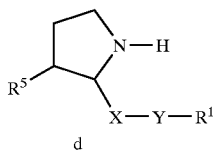
d

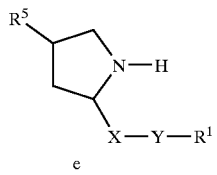
e

Linkers X-Y

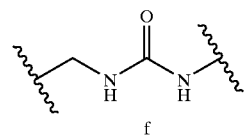
f

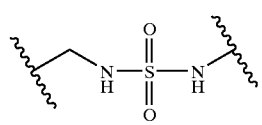
g

TABLE 2*-continued

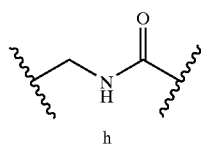
h

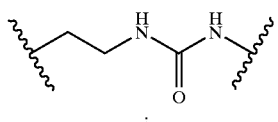
i

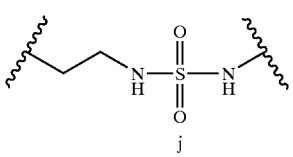
j

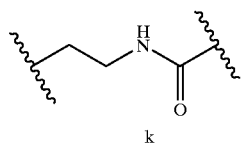
k

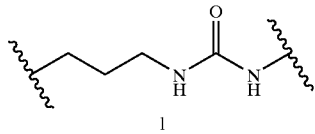
l

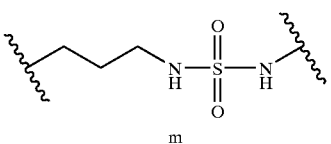
m

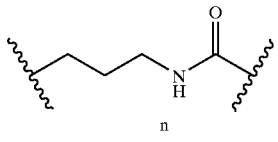
n

| Entry | $R^5$ | $R^1$ |
|---|---|---|
| 1 | Ph-CH$_2$— | Ph |
| 2 | Ph—CH$_2$— | 3-CN—Ph |
| 3 | Ph—CH$_2$— | 3-COCH3—Ph |
| 4 | Ph—CH$_2$— | 3-CO2Me—Ph |
| 5 | Ph—CH$_2$— | 3-CO2Et—Ph |
| 6 | Ph—CH$_2$— | 3-CO2H—Ph |
| 7 | Ph—CH$_2$— | 3-CONH2—Ph |
| 8 | Ph—CH$_2$— | 3-CONHMe—Ph |
| 9 | Ph—CH$_2$— | 3-F—Ph |
| 10 | Ph—CH$_2$— | 3-Cl—Ph |
| 11 | Ph—CH$_2$— | 3-Br—Ph |
| 12 | Ph—CH$_2$— | 3-NO2—Ph |
| 13 | Ph—CH$_2$— | 3-NH2—Ph |
| 14 | Ph—CH$_2$— | 3-NHMe—Ph |
| 15 | Ph—CH$_2$— | 3-NMe2—Ph |
| 16 | Ph—CH$_2$— | 3-NHCOCH3—Ph |
| 17 | Ph—CH$_2$— | 3-SO2NH2—Ph |
| 18 | Ph—CH$_2$— | 3-SO2NHMe—Ph |
| 19 | Ph—CH$_2$— | 3-CF3—Ph |
| 20 | Ph—CH$_2$— | 3-OCH3—Ph |
| 21 | Ph—CH$_2$— | 3-OPh—Ph |
| 22 | Ph—CH$_2$— | 3-OCF3—Ph |
| 23 | Ph—CH$_2$— | 3-SCH3—Ph |

TABLE 2*-continued

| | | |
|---|---|---|
| 24 | Ph—CH$_2$— | 3-SOCH3—Ph |
| 25 | Ph—CH$_2$— | 3-SO2CH3—Ph |
| 26 | Ph—CH$_2$— | 3-OH—Ph |
| 27 | Ph—CH$_2$— | 3-CH2OH—Ph |
| 28 | Ph—CH$_2$— | 3-CHOHCH3—Ph |
| 29 | Ph—CH$_2$— | 3-COH(CH3)2—Ph |
| 30 | Ph—CH$_2$— | 3-CHOHPh—Ph |
| 31 | Ph—CH$_2$— | 3-CH3—Ph |
| 32 | Ph—CH$_2$— | 3-C2H5—Ph |
| 33 | Ph—CH$_2$— | 3-iPr—Ph |
| 34 | Ph—CH$_2$— | 3-tBu—Ph |
| 35 | Ph—CH$_2$— | 3-Ph—Ph |
| 36 | Ph—CH$_2$— | 3-CH2Ph—Ph |
| 37 | Ph—CH$_2$— | 3-CH2CO2Me—Ph |
| 38 | Ph—CH$_2$— | 3-(1-piperidinyl)-Ph |
| 39 | Ph—CH$_2$— | 3-(1-pyrrolidinyl)-Ph |
| 40 | Ph—CH$_2$— | 3-(2-imidazolyl)-Ph |
| 41 | Ph—CH$_2$— | 3-(1-imidazolyl)-Ph |
| 42 | Ph—CH$_2$— | 3-(2-thiazolyl)-Ph |
| 43 | Ph—CH$_2$— | 3-(3-pyrazolyl)-Ph |
| 44 | Ph—CH$_2$— | 3-(1-pyrazolyl)-Ph |
| 45 | Ph—CH$_2$— | 3-(1-tetrazolyl)-Ph |
| 46 | Ph—CH$_2$— | 3-(5-tetrazolyl)-Ph |
| 47 | Ph—CH$_2$— | 3-(2-pyridyl)-Ph |
| 48 | Ph—CH$_2$— | 3-(2-thienyl)-Ph |
| 49 | Ph—CH$_2$— | 3-(2-turanyl)-Ph |
| 50 | Ph—CH$_2$— | 4-CN—Ph |
| 51 | Ph—CH$_2$— | 4-COCH3—Ph |
| 52 | Ph—CH$_2$— | 4-CO2Me—Ph |
| 53 | Ph—CH$_2$— | 4-CO2Et—Ph |
| 54 | Ph—CH$_2$— | 4-CO2H—Ph |
| 55 | Ph—CH$_2$— | 4-CONH2—Ph |
| 56 | Ph—CH$_2$— | 4-CONHMe—Ph |
| 57 | Ph—CH$_2$— | 4-CONHPh—Ph |
| 58 | Ph—CH$_2$— | 4-NHCONH2—Ph |
| 59 | Ph—CH$_2$— | 4-F—Ph |
| 60 | Ph—CH$_2$— | 4-Cl—Ph |
| 61 | Ph—CH$_2$— | 4-Br—Ph |
| 62 | Ph—CH$_2$— | 4-NO2—Ph |
| 63 | Ph—CH$_2$— | 4-NH2—Ph |
| 64 | Ph—CH$_2$— | 4-NHMe—Ph |
| 65 | Ph—CH$_2$— | 4-NMe2—Ph |
| 66 | Ph—CH$_2$— | 4-NHCOCH3—Ph |
| 67 | Ph—CH$_2$— | 4-SO2NH2—Ph |
| 68 | Ph—CH$_2$— | 4-SO2NHMe—Ph |
| 69 | Ph—CH$_2$— | 4-CF3—Ph |
| 70 | Ph—CH$_2$— | 4-OCH3—Ph |
| 71 | Ph—CH$_2$— | 4-OPh—Ph |
| 72 | Ph—CH$_2$— | 4-OCF3—Ph |
| 73 | Ph—CH$_2$— | 4-SCH3—Ph |
| 74 | Ph—CH$_2$— | 4-SOCH3—Ph |
| 75 | Ph—CH$_2$— | 4-SO2CH3—Ph |
| 76 | Ph—CH$_2$— | 4-OH—Ph |
| 77 | Ph—CH$_2$— | 4-CH2OH—Ph |
| 78 | Ph—CH$_2$— | 4-CHOHCH3—Ph |
| 79 | Ph—CH$_2$— | 4-COH(CH3)2—Ph |
| 80 | Ph—CH$_2$— | 4-CH3—Ph |
| 81 | Ph—CH$_2$— | 4-C2H5—Ph |
| 82 | Ph—CH$_2$— | 4-iPr—Ph |
| 83 | Ph—CH$_2$— | 4-tBu—Ph |
| 84 | Ph—CH$_2$— | 4-Ph—Ph |
| 85 | Ph—CH$_2$— | 4-CH2Ph—Ph |
| 86 | Ph—CH$_2$— | 4-CH2CO2Me—Ph |
| 87 | Ph—CH$_2$— | 4-(1-piperidinyl)-Ph |
| 88 | Ph—CH$_2$— | 4-(1-pyrrolidinyl)-Ph |
| 89 | Ph—CH$_2$— | 4-(2-imidazolyl)-Ph |
| 90 | Ph—CH$_2$— | 4-(1-imidazolyl)-Ph |
| 91 | Ph—CH$_2$— | 4-(2-thiazolyl)-Ph |
| 92 | Ph—CH$_2$— | 4-(3-pyrazolyl)-Ph |
| 93 | Ph—CH$_2$— | 4-(1-pyrazolyl)-Ph |
| 94 | Ph—CH$_2$— | 4-(1-tetrazolyl)-Ph |
| 95 | Ph—CH$_2$— | 4-(5-tetrazolyl)-Ph |
| 96 | Ph—CH$_2$— | 4-(2-pyridyl)-Ph |
| 97 | Ph—CH$_2$— | 4-(2-thienyl)-Ph |
| 98 | Ph—CH$_2$— | 4-(2-furanyl)-Ph |
| 99 | Ph—CH$_2$— | 2-CN—Ph |
| 100 | Ph—CH$_2$— | 2-COCH3—Ph |
| 101 | Ph—CH$_2$— | 2-CO2Me—Ph |
| 102 | Ph—CH$_2$— | 2-CO2EL—Ph |
| 103 | Ph—CH$_2$— | 2-CO2H—Ph |
| 104 | Ph—CH$_2$— | 2-CONH2—Ph |
| 105 | Ph—CH$_2$— | 2-CONHMe—Ph |
| 106 | Ph—CH$_2$— | 2-F—Ph |
| 107 | Ph—CH$_2$— | 2-Cl—Ph |
| 108 | Ph—CH$_2$— | 2-Br—Ph |
| 109 | Ph—CH$_2$— | 2-NO2—Ph |
| 110 | Ph—CH$_2$— | 2-NH2—Ph |
| 111 | Ph—CH$_2$— | 2-NHMe—Ph |
| 112 | Ph—CH$_2$— | 2-NMe2—Ph |
| 113 | Ph—CH$_2$— | 2-NHCOCH3—Ph |
| 114 | Ph—CH$_2$— | 2-SO2NH2—Ph |
| 115 | Ph—CH$_2$— | 2-SO2NHMe—Ph |
| 116 | Ph—CH$_2$— | 2-CF3—Ph |
| 117 | Ph—CH$_2$— | 2-OCH3—Ph |
| 118 | Ph—CH$_2$— | 2-OPh—Ph |
| 119 | Ph—CH$_2$— | 2-OCF3—Ph |
| 120 | Ph—CH$_2$— | 2-SCH3—Ph |
| 121 | Ph—CH$_2$— | 2-SOCH3—Ph |
| 122 | Ph—CH$_2$— | 2-SO2CH3—Ph |
| 123 | Ph—CH$_2$— | 2-OH—Ph |
| 124 | Ph—CH$_2$— | 2-CH2OH—Ph |
| 125 | Ph—CH$_2$— | 2-CHOHCH3—Ph |
| 126 | Ph—CH$_2$— | 2-COH(CH3)2—Ph |
| 127 | Ph—CH$_2$— | 2-CHOHPh—Ph |
| 128 | Ph—CH$_2$— | 2-CH3—Ph |
| 129 | Ph—CH$_2$— | 2-C2H5—Ph |
| 130 | Ph—CH$_2$— | 2-iPr—Ph |
| 131 | Ph—CH$_2$— | 2-tBu—Ph |
| 132 | Ph—CH$_2$— | 2-Ph—Ph |
| 133 | Ph—CH$_2$— | 2-CH2Ph—Ph |
| 134 | Ph—CH$_2$— | 2-CH2CO2Me—Ph |
| 135 | Ph—CH$_2$— | 2-(1-piperidinyl)-Ph |
| 136 | Ph—CH$_2$— | 2-(1-pyrrolidinyl)-Ph |
| 137 | Ph—CH$_2$— | 2-(2-imidazolyl)-Ph |
| 138 | Ph—CH$_2$— | 2-(1-imidazolyl)-Ph |
| 139 | Ph—CH$_2$— | 2-(2-thiazolyl)-Ph |
| 140 | Ph—CH$_2$— | 2-(3-pyrazolyl)-Ph |
| 141 | Ph—CH$_2$— | 2-(1-pyrazolyl)-Ph |
| 142 | Ph—CH$_2$— | 2-(1-tetrazolyl)-Ph |
| 143 | Ph—CH$_2$— | 2-(5-tetrazolyl)-Ph |
| 144 | Ph—CH$_2$— | 2-(2-pyridyl)-Ph |
| 145 | Ph—CH$_2$— | 2-(2-thienyl)-Ph |
| 146 | Ph—CH$_2$— | 2-(2-furanyl)-Ph |
| 147 | Ph—CH$_2$— | 2,4-diF—Ph |
| 148 | Ph—CH$_2$— | 2,5-diF—Ph |
| 149 | Ph—CH$_2$— | 2,6-diF—Ph |
| 150 | Ph—CH$_2$— | 3,4-diF—Ph |
| 151 | Ph—CH$_2$— | 3,5-diF—Ph |
| 152 | Ph—CH$_2$— | 2,4-diC—Ph |
| 153 | Ph—CH$_2$— | 2,5-diCl—Ph |
| 154 | Ph—CH$_2$— | 2,6-diCl—Ph |
| 155 | Ph—CH$_2$— | 3,4-diCl—Ph |
| 156 | Ph—CH$_2$— | 3,5-diCl—Ph |
| 157 | Ph—CH$_2$— | 3,4-diCF3—Ph |
| 158 | Ph—CH$_2$— | 3,5-diCF3—Ph |
| 159 | Ph—CH$_2$— | 5-Cl-2-MeO—Ph |
| 160 | Ph—CH$_2$— | 5-Cl-2-Me—Ph |
| 161 | Ph—CH$_2$— | 2-F-5-Me—Ph |
| 162 | Ph—CH$_2$— | 2-F-5-NO2—Ph |
| 163 | Ph—CH$_2$— | 3,4-OCH2O—Ph |
| 164 | Ph—CH$_2$— | 3,4-OCH2CH2O—Ph |
| 165 | Ph—CH$_2$— | 2-MeO-4-Me—Ph |
| 166 | Ph—CH$_2$— | 2-MeO-5-Me—Ph |
| 167 | Ph—CH$_2$— | 1-naphthyl |
| 168 | Ph—CH$_2$— | 2-naphthyl |
| 169 | Ph—CH$_2$— | 2-thienyl |
| 170 | Ph—CH$_2$— | 3-thienyl |
| 171 | Ph—CH$_2$— | 2-furanyl |
| 172 | Ph—CH$_2$— | 3-furanyl |
| 173 | Ph—CH$_2$— | 2-pyridyl |
| 174 | Ph—CH$_2$— | 3-pyridyl |
| 175 | Ph—CH$_2$— | 4-pyridyl |
| 176 | Ph—CH$_2$— | 2-indolyl |
| 177 | Ph—CH$_2$— | 3-indolyl |
| 178 | Ph—CH$_2$— | 5-indolyl |
| 179 | Ph—CH$_2$— | 6-indolyl |
| 180 | Ph—CH$_2$— | 3-indazolyl |
| 181 | Ph—CH$_2$— | 5-indazolyl |

TABLE 2*-continued

| | | |
|---|---|---|
| 182 | Ph—CH₂— | 6-indazolyl |
| 183 | Ph—CH₂— | 2-imidazolyl |
| 184 | Ph—CH₂— | 3-pyrazolyl |
| 185 | Ph—CH₂— | 2-thiazolyl |
| 186 | Ph—CH₂— | 5-tetrazolyl |
| 187 | Ph—CH₂— | 2-benzimidazolyl |
| 188 | Ph—CH₂— | 5-benzimidazolyl |
| 189 | Ph—CH₂— | 2-benzothiazolyl |
| 190 | Ph—CH₂— | 5-benzothiazolyl |
| 191 | Ph—CH₂— | 2-benzoxazolyl |
| 192 | Ph—CH₂— | 5-benzoxazolyl |
| 193 | Ph—CH₂— | 1-adamantyl |
| 194 | Ph—CH₂— | 2-adamantyl |
| 195 | Ph—CH₂— | t-Bu |
| 196 | Ph—CH₂— | Ph |
| 197 | Ph—CH₂— | 3-CN—Ph |
| 198 | 4-F—Ph—CH₂— | 3-COCH3—Ph |
| 199 | 4-F—Ph—CH₂— | 3-CO2Me—Ph |
| 200 | 4-F—Ph—CH₂— | 3-CO2Et—Ph |
| 201 | 4-F—Ph—CH₂— | 3-CO2H—Ph |
| 202 | 4-F—Ph—CH₂— | 3-CONH2—Ph |
| 203 | 4-F—Ph—CH₂— | 3-CONHMe—Ph |
| 204 | 4-F—Ph—CH₂— | 3-F—Ph |
| 205 | 4-F—Ph—CH₂— | 3-Cl—Ph |
| 206 | 4-F—Ph—H₂— | 3-Br—Ph |
| 207 | 4-F—Ph—CH₂— | 3-NO2—Ph |
| 208 | 4-F—Ph—CH₂— | 3-NH2—Ph |
| 209 | 4-F—Ph—CH₂— | 3-NHMe—Ph |
| 210 | 4-F—Ph—CH₂— | 3-NMe2—Ph |
| 211 | 4-F—Ph—CH₂— | 3-NHCOCH3—Ph |
| 212 | 4-F—Ph—CH₂— | 3-SO2NH2—Ph |
| 213 | 4-F—Ph—CH₂— | 3-SO2NHMe—Ph |
| 214 | 4-F—Ph—CH₂— | 3-CF3—Ph |
| 215 | 4-F—Ph—CH₂— | 3-OCH3—Ph |
| 216 | 4-F—Ph—CH₂— | 3-OPh—Ph |
| 217 | 4-F—Ph—CH₂— | 3-OCF3—Ph |
| 218 | 4-F—Ph—CH₂— | 3-SCH3—Ph |
| 219 | 4-F—Ph—CH₂— | 3-SOCH3—Ph |
| 220 | 4-F—Ph—CH₂— | 3-SO2CH3—Ph |
| 221 | 4-F—Ph—CH₂— | 3-OH—Ph |
| 222 | 4-F—Ph—CH₂— | 3-CH2OH—Ph |
| 223 | 4-F—Ph—CH₂— | 3-CHOHCH3—Ph |
| 224 | 4-F—Ph—CH₂— | 3-COH(CH3)2-Ph |
| 225 | 4-F—Ph—CH₂— | 3-CHOHPh—Ph |
| 226 | 4-F—Ph—CH₂— | 3-CH3—Ph |
| 227 | 4-F—Ph—CH₂— | 3-C2H5—Ph |
| 228 | 4-F—Ph—CH₂— | 3-iPr—Ph |
| 229 | 4-F—Ph—CH₂— | 3-tBu—Ph |
| 230 | 4-F—Ph—CH₂— | 3-Ph—Ph |
| 231 | 4-F—Ph—CH₂— | 3-CH2Ph—Ph |
| 232 | 4-F—Ph—CH₂— | 3-CH2CO2Me—Ph |
| 233 | 4-F—Ph—CH₂— | 3-(1-piperidinyl)—Ph |
| 234 | 4-F—Ph—CH₂— | 3-(1-pyrrolidinyl)—Ph |
| 235 | 4-F—Ph—CH₂— | 3-(2-imidazolyl)—Ph |
| 236 | 4-F—Ph—CH₂— | 3-(1-imidazolyl)—Ph |
| 237 | 4-F—Ph—CH₂— | 3-(2-thiazolyl)—Ph |
| 238 | 4-F—Ph—CH₂— | 3-(3-pyrazolyl)—Ph |
| 239 | 4-F—Ph—CH₂— | 3-(1-pyrazolyl)—Ph |
| 240 | 4-F—Ph—CH₂— | 3-(1-tetrazolyl)—Ph |
| 241 | 4-F—Ph—CH₂— | 3-(5-tetrazolyl)—Ph |
| 242 | 4-F—Ph—CH₂— | 3-(2-pyridyl)—Ph |
| 243 | 4-F—Ph—CH₂— | 3-(2-thienyl)—Ph |
| 244 | 4-F—Ph—CH₂— | 3-(2-furanyl)—Ph |
| 245 | 4-F—Ph—CH₂— | 4-CN—Ph |
| 246 | 4-F—Ph—CH₂— | 4-COCH3—Ph |
| 247 | 4-F—Ph—CH₂— | 4-CO2Me—Ph |
| 248 | 4-F—Ph—CH₂— | 4-CO2Et—Ph |
| 249 | 4-F—Ph—CH₂— | 4-CO2H—Ph |
| 250 | 4-F—Ph—CH₂— | 4-CONH2—Ph |
| 251 | 4-F—Ph—CH₂— | 4-CONHMe—Ph |
| 252 | 4-F—Ph—CH₂— | 4-CONHPh—Ph |
| 253 | 4-F—Ph—CH₂— | 4-NHCONH2—Ph |
| 254 | 4-F—Ph—CH₂— | 4-F—Ph |
| 255 | 4-F—Ph—CH₂— | 4-Cl—Ph |
| 256 | 4-F—Ph—CH₂— | 4-Br—Ph |
| 257 | 4-F—Ph—CH₂— | 4-NO2—Ph |
| 258 | 4-F—Ph—CH₂— | 4-NH2—Ph |
| 259 | 4-F—Ph—CH₂— | 4-NHMe—Ph |
| 260 | 4-F—Ph—CH₂— | 4-NMe2—Ph |
| 261 | 4-F—Ph—CH₂— | 4-NHCOCH3—Ph |
| 262 | 4-F—Ph—CH₂— | 4-SO2NH2—Ph |
| 263 | 4-F—Ph—CH₂— | 4-SO2NHMe—Ph |
| 264 | 4-F—Ph—CH₂— | 4-CF3—Ph |
| 265 | 4-F—Ph—CH₂— | 4-OCH3—Ph |
| 266 | 4-F—Ph—CH₂— | 4-OPh—Ph |
| 267 | 4-F—Ph—CH₂— | 4-OCF3—Ph |
| 268 | 4-F—Ph—CH₂— | 4-SCH3—Ph |
| 269 | 4-F—Ph—CH₂— | 4-SOCH3—Ph |
| 270 | 4-F—Ph—CH₂— | 4-SO2CH3—Ph |
| 271 | 4-F—Ph—CH₂— | 4-OH—Ph |
| 272 | 4-F—Ph—CH₂— | 4-CH2OH—Ph |
| 273 | 4-F—Ph—CH₂— | 4-CHOHCH3—Ph |
| 274 | 4-F—Ph—CH₂— | 4-COH(CH3)2-Ph |
| 275 | 4-F—Ph—CH₂— | 4-CH3—Ph |
| 276 | 4-F—Ph—CH₂— | 4-C2H5—Ph |
| 277 | 4-F—Ph—CH₂— | 4-iPr—Ph |
| 278 | 4-F—Ph—CH₂— | 4-tBu—Ph |
| 279 | 4-F—Ph—CH₂— | 4-Ph—Ph |
| 280 | 4-F—Ph—CH₂— | 4-CH2Ph—Ph |
| 281 | 4-F—Ph—CH₂— | 4-CH2CO2Me—Ph |
| 282 | 4-F—Ph—CH₂— | 4-(1-piperidinyl)-Ph |
| 283 | 4-F—Ph—CH₂— | 4-(1-pyrrolidinyl)-Ph |
| 284 | 4-F—Ph—CH₂— | 4-(2-imidazolyl)-Ph |
| 285 | 4-F—Ph—CH₂— | 4-(1-imidazolyl)-Ph |
| 286 | 4-F—Ph—CH₂— | 4-(2-thiazolyl)-Ph |
| 287 | 4-F—Ph—CH₂— | 4-(3-pyrazolyl)-Ph |
| 288 | 4-F—Ph—CH₂— | 4-(1-pyrazolyl)-Ph |
| 289 | 4-F—Ph—CH₂— | 4-(1-tetrazolyl)-Ph |
| 290 | 4-F—Ph—CH₂— | 4-(5-tetrazolyl)-Ph |
| 291 | 4-F—Ph—CH₂— | 4-(2-pyridyl)-Ph |
| 292 | 4-F—Ph—CH₂— | 4-(2-thienyl)-Ph |
| 293 | 4-F—Ph—CH₂— | 4-(2-furanyl)-Ph |
| 294 | 4-F—Ph—CH₂— | 2-CN—Ph |
| 295 | 4-F—Ph—CH₂— | 2-COCH3—Ph |
| 296 | 4-F—Ph—CH₂— | 2-CO2Me—Ph |
| 297 | 4-F—Ph—CH₂— | 2-CO2Et—Ph |
| 298 | 4-F—Ph—CH₂— | 2-CO2H—Ph |
| 299 | 4-F—Ph—CH₂— | 2-CONH2—Ph |
| 300 | 4-F—Ph—CH₂— | 2-CONHMe—Ph |
| 301 | 4-F—Ph—CH₂— | 2-F—Ph |
| 302 | 4-F—Ph—CH₂— | 2-Cl—Ph |
| 303 | 4-F—Ph—CH₂— | 2-Br—Ph |
| 304 | 4-F—Ph—CH₂— | 2-NO2—Ph |
| 305 | 4-F—Ph—CH₂— | 2-NH2—Ph |
| 306 | 4-F—Ph—CH₂— | 2-NHMe—Ph |
| 307 | 4-F—Ph—CH₂— | 2-NMe2—Ph |
| 308 | 4-F—Ph—CH₂— | 2-NHCOCH3—Ph |
| 309 | 4-F—Ph—CH₂— | 2-SO2NH2—Ph |
| 310 | 4-F—Ph—CH₂— | 2-SO2NHMe—Ph |
| 311 | 4-F—Ph—CH₂— | 2-CF3—Ph |
| 312 | 4-F—Ph—CH₂— | 2-OCH3—Ph |
| 313 | 4-F—Ph—CH₂— | 2-OPh—Ph |
| 314 | 4-F—Ph—CH₂— | 2-OCF3—Ph |
| 315 | 4-F—Ph—CH₂— | 2-SCH3—Ph |
| 316 | 4-F—Ph—CH₂— | 2-SOCH3—Ph |
| 317 | 4-F—Ph—CH₂— | 2-SO2CH3—Ph |
| 318 | 4-F—Ph—CH₂— | 2-OH—Ph |
| 319 | 4-F—Ph—CH₂— | 2-CH2OH—Ph |
| 320 | 4-F—Ph—CH₂— | 2-CHOHCH3—Ph |
| 321 | 4-F—Ph—CH₂— | 2-COH(CH3)2-Ph |
| 322 | 4-F—Ph—CH₂— | 2-CHOHPh—Ph |
| 323 | 4-F—Ph—CH₂— | 2-CH3—Ph |
| 324 | 4-F—Ph—CH₂— | 2-C2H5—Ph |
| 325 | 4-F—Ph—CH₂— | 2-iPr—Ph |
| 326 | 4-F—Ph—CH₂— | 2-tBu—Ph |
| 327 | 4-F—Ph—CH₂— | 2-Ph—Ph |
| 328 | 4-F—Ph—CH₂— | 2-CH2Ph—Ph |
| 329 | 4-F—Ph—CH₂— | 2-CH2CO2Me—Ph |
| 330 | 4-F—Ph—CH₂— | 2-(1-piperidinyl)-Ph |
| 331 | 4-F—Ph—CH₂— | 2-(1-pyrrolidinyl)-Ph |
| 332 | 4-F—Ph—CH₂— | 2-(2-imidazolyl)-Ph |
| 333 | 4-F—Ph—CH₂— | 2-(1-imidazolyl)-Ph |
| 334 | 4-F—Ph—CH₂— | 2-(2-thiazolyl)-Ph |
| 335 | 4-F—Ph—CH₂— | 2-(3-pyrazolyl)-Ph |
| 336 | 4-F—Ph—CH₂— | 2-(1-pyrazolyl)-Ph |
| 337 | 4-F—Ph—CH₂— | 2-(1-tetrazolyl)-Ph |
| 338 | 4-F—Ph—CH₂— | 2-(5-tetrazolyl)-Ph |
| 339 | 4-F—Ph—CH₂— | 2-(2-pyridyl)-Ph |

TABLE 2*-continued

| | | |
|---|---|---|
| 340 | 4-F—Ph—CH₂— | 2-(2-thienyl)-Ph |
| 341 | 4-F—Ph—CH₂— | 2-(2-furanyl)-Ph |
| 342 | 4-F—Ph—CH₂— | 2,4-diF—Ph |
| 343 | 4-F—Ph—CH₂— | 2,5-diF—Ph |
| 344 | 4-F—Ph—CH₂— | 2,6-diF—Ph |
| 345 | 4-F—Ph—CH₂— | 3,4-diF—Ph |
| 346 | 4-F—Ph—CH₂— | 3,5-diF—Ph |
| 347 | 4-F—Ph—CH₂— | 2,4-diCl—Ph |
| 348 | 4-F—Ph—CH₂— | 2,5-diCl—Ph |
| 349 | 4-F—Ph—CH₂— | 2,6-diCl—Ph |
| 350 | 4-F—Ph—CH₂— | 3,4-diCl—Ph |
| 351 | 4-F—Ph—CH₂— | 3,5-diCl—Ph |
| 352 | 4-F—Ph—CH₂— | 3,4-diCF3—Ph |
| 353 | 4-F—Ph—CH₂— | 3,5-diCF3—Ph |
| 354 | 4-F—Ph—CH₂— | 5-Cl-2-MeO—Ph |
| 355 | 4-F—Ph—CH₂— | 5-Cl-2-Me—Ph |
| 356 | 4-F—Ph—CH₂— | 2-F-5-Me—Ph |
| 357 | 4-F—Ph—CH₂— | 2-F-5-NO2—Ph |
| 358 | 4-F—Ph—CH₂— | 3,4-OCH2O—Ph |
| 359 | 4-F—Ph—CH₂— | 3,4-OCH2CH2O—Ph |
| 360 | 4-F—Ph—CH₂— | 2-MeO-4-Me—Ph |
| 361 | 4-F—Ph—CH₂— | 2-MeO-5-Me—Ph |
| 362 | 4-F—Ph—CH₂— | 1-naphthyl |
| 363 | 4-F—Ph—CH₂— | 2-naphthyl |
| 364 | 4-F—Ph—CH₂— | 2-thienyl |
| 365 | 4-F—Ph—CH₂— | 3-thienyl |
| 366 | 4-F—Ph—CH₂— | 2-furanyl |
| 367 | 4-F—Ph—CH₂— | 3-furanyl |
| 368 | 4-F—Ph—CH₂— | 2-pyridyl |
| 369 | 4-F—Ph—CH₂— | 3-pyridyl |
| 370 | 4-F—Ph—CH₂— | 4-pyridyl |
| 371 | 4-F—Ph—CH₂— | 2-indolyl |
| 372 | 4-F—Ph—CH₂— | 3-indolyl |
| 373 | 4-F—Ph—CH₂— | 5-indolyl |
| 374 | 4-F—Ph—CH₂— | 6-indolyl |
| 375 | 4-F—Ph—CH₂— | 3-indazolyl |
| 376 | 4-F—Ph—CH₂— | 5-indazolyl |
| 377 | 4-F—Ph—CH₂— | 6-indazolyl |
| 378 | 4-F—Ph—CH₂— | 2-imidazolyl |
| 379 | 4-F—Ph—CH₂— | 3-pyrazolyl |
| 380 | 4-F—Ph—CH₂— | 2-thiazolyl |
| 381 | 4-F—Ph—CH₂— | 5-tetrazolyl |
| 382 | 4-F—Ph—CH₂— | 2-benzimidazolyl |
| 383 | 4-F—Ph—CH₂— | 5-benzimidazolyl |
| 384 | 4-F—Ph—CH₂— | 2-benzothiazolyl |
| 385 | 4-F—Ph—CH₂— | 5-benzothiazolyl |
| 386 | 4-F—Ph—CH₂— | 2-benzoxazolyl |
| 387 | 4-F—Ph—CH₂— | 5-benzoxazolyl |
| 388 | 4-F—Ph—CH₂— | 1-adamantyl |
| 389 | 4-F—Ph—CH₂— | 2-adamantyl |
| 390 | 4-F—Ph—CH₂— | t-Bu |
| 391 | 2-F—Ph—CH₂— | 3-CN—Ph |
| 392 | 2-F—Ph—CH₂— | 3-COCH3—Ph |
| 393 | 2-F—Ph—CH₂— | 3-CO2Me—Ph |
| 394 | 2-F—Ph—CH₂— | 3-CO2Et—Ph |
| 395 | 2-F—Ph—CH₂— | 3-CO2H—Ph |
| 396 | 2-F—Ph—CH₂— | 3-CONH2—Ph |
| 397 | 2-F—Ph—CH₂— | 3-F—Ph |
| 398 | 2-F—Ph—CH₂— | 3-Cl—Ph |
| 399 | 2-F—Ph—CH₂— | 3-NH2—Ph |
| 400 | 2-F—Ph—CH₂— | 3-SO2NH2—Ph |
| 401 | 2-F—Ph—CH₂— | 3-CF3—Ph |
| 402 | 2-F—Ph—CH₂— | 3-OCH3—Ph |
| 403 | 2-F—Ph—CH₂— | 3-OEt—Ph |
| 404 | 2-F—Ph—CH₂— | 3-OCF3—Ph |
| 405 | 2-F—Ph—CH₂— | 3-SO2CH3—Ph |
| 406 | 2-F—Ph—CH₂— | 3-OH—Ph |
| 407 | 2-F—Ph—CH₂— | 3-CH3—Ph |
| 408 | 2-F—Ph—CH₂— | 3-C2H5—Ph |
| 409 | 2-F—Ph—CH₂— | 4-CN—Ph |
| 410 | 2-F—Ph—CH₂— | 4-COCH3—Ph |
| 411 | 2-F—Ph—CH₂— | 4-CO2Me—Ph |
| 412 | 2-F—Ph—CH₂— | 4-CO2Et—Ph |
| 413 | 2-F—Ph—CH₂— | 4-CO2H—Ph |
| 414 | 2-F—Ph—CH₂— | 4-CONH2—Ph |
| 415 | 2-F—Ph—CH₂— | 4-F—Ph |
| 416 | 2-F—Ph—CH₂— | 4-Cl—Ph |
| 417 | 2-F—Ph—CH₂— | 4-NH2—Ph |
| 418 | 2-F—Ph—CH₂— | 4-SO2NH—Ph |
| 419 | 2-F—Ph—CH₂— | 4-CF3—Ph |
| 420 | 2-F—Ph—CH₂— | 4-OCH3—Ph |
| 421 | 2-F—Ph—CH₂— | 4-OEt—Ph |
| 422 | 2-F—Ph—CH₂— | 4-OCF3—Ph |
| 423 | 2-F—Ph—CH₂— | 4-SO2CH3—Ph |
| 424 | 2-F—Ph—CH₂— | 4-OH—Ph |
| 425 | 2-F—Ph—CH₂— | 4-CH3—Ph |
| 426 | 2-F—Ph—CH₂— | 4-C2H5—Ph |
| 427 | 2-F—Ph—CH₂— | 2,4-diF—Ph |
| 428 | 2-F—Ph—CH₂— | 2,5-diF—Ph |
| 429 | 2-F—Ph—CH₂— | 3,4-diF—Ph |
| 430 | 2-F—Ph—CH₂— | 3,5-diF—Ph |
| 431 | 2-F—Ph—CH₂— | 2,4-diCl—Ph |
| 432 | 2-F—Ph—CH₂— | 2,5-diCl—Ph |
| 433 | 2-F—Ph—CH₂— | 3,4-diCl—Ph |
| 434 | 2-F—Ph—CH₂— | 3,5-diCl—Ph |
| 435 | 2-F—Ph—CH₂— | 3,4-OCH2O—Ph |
| 436 | 2-F—Ph—CH₂— | 3,4-OCH2CH2O—Ph |
| 437 | 2-F—Ph—CH₂— | 2-thienyl |
| 438 | 2-F—Ph—CH₂— | 2-furanyl |
| 439 | 2-F—Ph—CH₂— | 2-pyridyl |
| 440 | 2-F—Ph—CH₂— | 4-pyridyl |
| 441 | 2-F—Ph—CH₂— | 2-imidazolyl |
| 442 | 2-F—Ph—CH₂— | 3-pyrazolyl |
| 443 | 2-F—Ph—CH₂— | 2-thiazolyl |
| 444 | 2-F—Ph—CH₂— | 5-tetrazolyl |
| 445 | 2-F—Ph—CH₂— | 1-adamantyl |
| 446 | 2,4—diF-Ph—CH₂— | 3-CN—Ph |
| 447 | 2,4-F-Ph—CH₂— | 3-COCH3—Ph |
| 448 | 2,4-diF-Ph—CH₂— | 3-CO2Me—Ph |
| 449 | 2,4-diF-Ph—CH₂— | 3-CO2Et—Ph |
| 450 | 2,4-diF-Ph—CH₂— | 3-CO2H—Ph |
| 451 | 2,4-diF-Ph—CH₂— | 3-CONH2—Ph |
| 452 | 2,4-diF-Ph—CH₂— | 3-F—Ph |
| 453 | 2,4-diF-Ph—CH₂— | 3-Cl—Ph |
| 454 | 2,4-diF-Ph—CH₂— | 3-NH2—Ph |
| 455 | 2,4-diF-Ph—CH₂— | 3-SO2NH2—Ph |
| 456 | 2,4-diF-Ph—CH₂— | 3-CF3—Ph |
| 457 | 2,4-diF-Ph—CH₂— | 3-OCH3—Ph |
| 458 | 2,4-diF-Ph—CH₂— | 3-OEt—Ph |
| 459 | 2,4-diF-Ph—CH₂— | 3-OCF3—Ph |
| 460 | 2,4-diF-Ph—CH₂— | 3-SO2CH3—Ph |
| 461 | 2,4-diF-Ph—CH₂— | 3-OH—Ph |
| 462 | 2,4-diF-Ph—CH₂— | 3-CH3—Ph |
| 463 | 2,4-diF-Ph—CH₂— | 3-C2H5—Ph |
| 464 | 2,4-diF-Ph—CH₂— | 4-CN—Ph |
| 465 | 2,4-diF-Ph—CH₂— | 4-COCH3—Ph |
| 466 | 2,4-diF-Ph—CH₂— | 4-CO2Me—Ph |
| 467 | 2,4-diF-Ph—CH₂— | 4-CO2Et—Ph |
| 468 | 2,4-diF-Ph—CH₂— | 4-CO2H—Ph |
| 469 | 2,4-diF-Ph—CH₂— | 4-CONH2—Ph |
| 470 | 2,4-diF-Ph—CH₂— | 4-F—Ph |
| 471 | 2,4-diF-Ph—CH₂— | 4-Cl—Ph |
| 472 | 2,4-diF-Ph—CH₂— | 4-NH2—Ph |
| 473 | 2,4-diF-Ph—CH₂— | 4-SO2NH2—Ph |
| 474 | 2,4-diF-Ph—CH₂— | 4-CF3—Ph |
| 475 | 2,4-diF-Ph—CH₂— | 4-OCH3—Ph |
| 476 | 2,4-diF-Ph—CH₂— | 4-OEt—Ph |
| 477 | 2,4-diF-Ph—CH₂— | 4-OCF3—Ph |
| 478 | 2,4-diF-Ph—CH₂— | 4-SO2CH3—Ph |
| 479 | 2,4-diF-Ph—CH₂— | 4-OH—Ph |
| 480 | 2,4-diF-Ph—CH₂— | 4-CH3—Ph |
| 481 | 2,4-diF-Ph—CH₂— | 4-C2H5—Ph |
| 482 | 2,4-diF-Ph—CH₂— | 2,4-diF—Ph |
| 483 | 2,4-diF-Ph—CH₂— | 2,5-diF—Ph |
| 484 | 2,4-diF-Ph—CH₂— | 3,4-diF—Ph |
| 485 | 2,4-diF-Ph—CH₂— | 3,5-diF—Ph |
| 486 | 2,4-diF-Ph—CH₂— | 2,4-diCl—Ph |
| 487 | 2,4-diF-Ph—CH₂— | 2,5-diCl—Ph |
| 488 | 2,4-diF-Ph—CH₂— | 3,4-diCl—Ph |
| 489 | 2,4-diF-Ph—CH₂— | 3,5-diCl—Ph |
| 490 | 2,4-diF-Ph—CH₂— | 3,4-OCH2O—Ph |
| 491 | 2,4-diF-Ph—CH₂— | 3,4-OCH2CH2O—Ph |
| 492 | 2,4-diF-Ph—CH₂— | 2-thienyl |
| 493 | 2,4-diF-Ph—CH₂— | 2-furanyl |
| 494 | 2,4-diF-Ph—CH₂— | 2-pyridyl |
| 495 | 2,4-diF-Ph—CH₂— | 4-pyridyl |
| 496 | 2,4-diF-Ph—CH₂— | 2-imidazolyl |
| 497 | 2,4-diF-Ph—CH₂— | 3-pyrazolyl |

TABLE 2*-continued

| | | |
|---|---|---|
| 498 | 2,4-diF-Ph—CH₂— | 2-thiazolyl |
| 499 | 2,4-diF-Ph—CH₂— | 5-tetrazolyl |
| 500 | 2,4-diF-Ph—CH₂— | 1-adamantyl |
| 501 | 4-Cl—Ph—CH₂— | Ph |
| 502 | 4-Cl—Ph—CHhd 2— | 3-CN—Ph |
| 503 | 4-Cl—Ph—CH₂— | 3-COCH3—Ph |
| 504 | 4-Cl—Ph—CH₂— | 3-CO2Me—Ph |
| 505 | 4-Cl—Ph—CH₂— | 3-CO2EL—Ph |
| 506 | 4-Cl—Ph—CH₂— | 3-CO2H—Ph |
| 507 | 4-Cl—Ph—CH₂— | 3-CONH2—Ph |
| 508 | 4-Cl—Ph—CH₂— | 3-CONHMe—Ph |
| 509 | 4-Cl—Ph—CH₂— | 3-F—Ph |
| 510 | 4-Cl—Ph—CH₂— | 3-Cl—Ph |
| 511 | 4-Cl—Ph—CH₂— | 3-Br—Ph |
| 512 | 4-Cl—Ph—CH₂— | 3-NO2—Ph |
| 513 | 4-Cl—Ph—CH₂— | 3-NH2—Ph |
| 514 | 4-Cl—Ph—CH₂— | 3-NHMe—Ph |
| 515 | 4-Cl—Ph—CH₂— | 3-NMe2—Ph |
| 516 | 4-Cl—Ph—CH₂— | 3-NHCOCH3—Ph |
| 517 | 4-Cl—Ph—CH₂— | 3-SO2NH2—Ph |
| 518 | 4-Cl—Ph—CH₂— | 3-SO2NHMe—Ph |
| 519 | 4-Cl—Ph—CH₂— | 3-CF3—Ph |
| 520 | 4-Cl—Ph—CH₂— | 3-OCH3—Ph |
| 521 | 4-Cl—Ph—CH₂— | 3-OPh—Ph |
| 522 | 4-Cl—Ph—CH₂— | 3-OCF3—Ph |
| 523 | 4-Cl—Ph—CH₂— | 3-SCH3—Ph |
| 524 | 4-Cl—Ph—CH₂— | 3-SOCH3—Ph |
| 525 | 4-Cl—Ph—CH₂— | 3-SO2CH3—Ph |
| 526 | 4-Cl—Ph—CH₂— | 3-OH—Ph |
| 527 | 4-Cl—Ph—CH₂— | 3-CH2OH—Ph |
| 528 | 4-Cl—Ph—CH₂— | 3-CHOHCH3—Ph |
| 529 | 4-Cl—Ph—CH₂— | 3-COH(CH3)2—Ph |
| 530 | 4-Cl—Ph—CH₂— | 3-CHOHPh—Ph |
| 531 | 4-Cl—Ph—CH₂— | 3-CH3—Ph |
| 532 | 4-Cl—Ph—CH₂— | 3-C2H5—Ph |
| 533 | 4-Cl—Ph—CH₂— | 3-iPr—Ph |
| 534 | 4-Cl—Ph—CH₂— | 3-tBu—Ph |
| 535 | 4-Cl—Ph—CH₂— | 3-Ph—Ph |
| 536 | 4-Cl—Ph—CH₂— | 3-CH2Ph—Ph |
| 537 | 4-Cl—Ph—CH₂— | 3-CH2CO2Me—Ph |
| 538 | 4-Cl—Ph—CH₂— | 3-(1-piperidinyl)-Ph |
| 539 | 4-Cl—Ph—CH₂— | 3-(1-pyrrolidinyl)-Ph |
| 540 | 4-Cl—Ph—CH₂— | 3-(2-imidazolyl)-Ph |
| 541 | 4-Cl—Ph—CH₂— | 3-(1-imidazolyl)-Ph |
| 542 | 4-Cl—Ph—CH₂— | 3-(2-thiazolyl)-Ph |
| 543 | 4-Cl—Ph—CH₂— | 3-(3-pyrazolyl)-Ph |
| 544 | 4-Cl—Ph—CH₂— | 3-(1-pyrazolyl)-Ph |
| 545 | 4-Cl—Ph—CH₂— | 3-(1-tetrazolyl)-Ph |
| 546 | 4-Cl—Ph—CH₂— | 3-(5-tetrazolyl)-Ph |
| 547 | 4-Cl—Ph—CH₂— | 3-(2-pyridyl)-Ph |
| 548 | 4-Cl—Ph—CH₂— | 3-(2-thienyl)-Ph |
| 549 | 4-Cl—Ph—CH₂— | 3-(2-furanyl)-Ph |
| 550 | 4-Cl—Ph—CH₂— | 4-CN—Ph |
| 551 | 4-Cl—Ph—CH₂— | 4-COCH3—Ph |
| 552 | 4-Cl—Ph—CH₂— | 4-CO2Me—Ph |
| 553 | 4-Cl—Ph—CH₂— | 4-CO2Et—Ph |
| 554 | 4-Cl—Ph—CH₂— | 4-CO2H—Ph |
| 555 | 4-Cl—Ph—CH₂— | 4-CONH2—Ph |
| 556 | 4-Cl—Ph—CH₂— | 4-CONEMe—Ph |
| 557 | 4-Cl—Ph—CH₂— | 4-CONHPh—Ph |
| 558 | 4-Cl—Ph—CH₂— | 4-NHCONH2—Ph |
| 559 | 4-Cl—Ph—CH₂— | 4-F—Ph |
| 560 | 4-Cl—Ph—CH₂— | 4-Cl—Ph |
| 561 | 4-Cl—Ph—CH₂— | 4-Br—Ph |
| 562 | 4-Cl—Ph—CH₂— | 4-NO2—Ph |
| 563 | 4-Cl—Ph—CH₂— | 4-NE2—Ph |
| 564 | 4-Cl—Ph—CH₂— | 4-NHMe—Ph |
| 565 | 4-Cl—Ph—CH₂— | 4-NMe2—Ph |
| 566 | 4-Cl—Ph—CH₂— | 4-NHCOCH3—Ph |
| 567 | 4-Cl—Ph—CH₂— | 4-SO2NH2—Ph |
| 568 | 4-Cl—Ph—CH₂— | 4-SO2NHMe—Ph |
| 569 | 4-Cl—Ph—CH₂— | 4-CF3—Ph |
| 570 | 4-Cl—Ph—CH₂— | 4-OCH3—Ph |
| 571 | 4-Cl—Ph—CH₂— | 4-OPh—Ph |
| 572 | 4-Cl—Ph—CH₂— | 4-OCF3—Ph |
| 573 | 4-Cl—Ph—CH₂— | 4-SCH3—Ph |
| 574 | 4-Cl—Ph—CH₂— | 4-SOCH3—Ph |
| 575 | 4-Cl—Ph—CH₂— | 4-SO2CH3—Ph |
| 576 | 4-Cl—Ph—CH₂— | 4-OH—Ph |
| 577 | 4-Cl—Ph—CH₂— | 4-CH2OH—Ph |
| 578 | 4-Cl—Ph—CH₂— | 4-CHOHCH3—Ph |
| 579 | 4-Cl—Ph—CH₂— | 4-COH(CH3)2—Ph |
| 580 | 4-Cl—Ph—CH₂— | 4-CH3—Ph |
| 581 | 4-Cl—Ph—CH₂— | 4-C2H5—Ph |
| 582 | 4-Cl—Ph—CH₂— | 4-iPr—Ph |
| 583 | 4-Cl—Ph—CH₂— | 4-tBu—Ph |
| 584 | 4-Cl—Ph—CH₂— | 4-Ph—Ph |
| 585 | 4-Cl—Ph—CH₂— | 4-CH2Ph—Ph |
| 586 | 4-Cl—Ph—CH₂— | 4-CH2CO2Me—Ph |
| 587 | 4-Cl—Ph—CH₂— | 4-(1-piperidinyl)-Ph |
| 588 | 4-Cl—Ph—CH₂— | 4-(1-pyrrolidinyl)-Ph |
| 589 | 4-Cl—Ph—CH₂— | 4-(2-imidazolyl)-Ph |
| 590 | 4-Cl—Ph—CH₂— | 4-(1-imidazolyl)-Ph |
| 591 | 4-Cl—Ph—CH₂— | 4-(2-thiazolyl)-Ph |
| 592 | 4-Cl—Ph—CH₂— | 4-(3-pyrazolyl)-Ph |
| 593 | 4-Cl—Ph—CH₂— | 4-(1-pyrazolyl)-Ph |
| 594 | 4-Cl—Ph—CH₂— | 4-(1-tetrazolyl)-Ph |
| 595 | 4-Cl—Ph—CH₂— | 4-(5-tetrazolyl)-Ph |
| 596 | 4-Cl—Ph—CH₂— | 4-(2-pyridyl)-Ph |
| 597 | 4-Cl—Ph—CH₂— | 4-(2-thienyl)-Ph |
| 598 | 4-Cl—Ph—CH₂— | 4-(2-furanyl)-Ph |
| 599 | 4-Cl—Ph—CH₂— | 2-CN—Ph |
| 600 | 4-Cl—Ph—CH₂— | 2-COCH3—Ph |
| 601 | 4-Cl—Ph—CH₂— | 2-CO2Me—Ph |
| 602 | 4-Cl—Ph—CH₂— | 2-CO2Et—Ph |
| 603 | 4-Cl—Ph—CH₂— | 2-CO2H—Ph |
| 604 | 4-Cl—Ph—CH₂— | 2-CONH2—Ph |
| 605 | 4-Cl—Ph—CH₂— | 2-CONHMe—Ph |
| 606 | 4-Cl—Ph—CH₂— | 2-F—Ph |
| 607 | 4-Cl—Ph—CH₂— | 2-Cl—Ph |
| 608 | 4-Cl—Ph—CH₂— | 2-Br—Ph |
| 609 | 4-Cl—Ph—CH₂— | 2-NO2—Ph |
| 610 | 4-Cl—Ph—CH₂— | 2-NH2—Ph |
| 611 | 4-Cl—Ph—CH₂— | 2-NHMe—Ph |
| 612 | 4-Cl—Ph—CH₂— | 2-NMe2—Ph |
| 613 | 4-Cl—Ph—CH₂— | 2-NHCOCH3—Ph |
| 614 | 4-Cl—Ph—CH₂— | 2-SO2NH2—Ph |
| 615 | 4-Cl—Ph—CH₂— | 2-SO2NHMe—Ph |
| 616 | 4-Cl—Ph—CH₂— | 2-CF3—Ph |
| 617 | 4-Cl—Ph—CH₂— | 2-OCH3—Ph |
| 618 | 4-Cl—Ph—CH₂— | 2-OPh—Ph |
| 619 | 4-Cl—Ph—CH₂— | 2-OCF3—Ph |
| 620 | 4-Cl—Ph—CH₂— | 2-SCH3—Ph |
| 621 | 4-Cl—Ph—CH₂— | 2-SOCH3—Ph |
| 622 | 4-Cl—Ph—CH₂— | 2-SO2CH3—Ph |
| 623 | 4-Cl—Ph—CH₂— | 2-OH—Ph |
| 624 | 4-Cl—Ph—CH₂— | 2-CH2OH—Ph |
| 625 | 4-Cl—Ph—CH₂— | 2-CHOHCH3—Ph |
| 626 | 4-Cl—Ph—CH₂— | 2-COH(CH3)2—Ph |
| 627 | 4-Cl—Ph—CH₂— | 2-CHOHPh—Ph |
| 628 | 4-Cl—Ph—CH₂— | 2-CH3—Ph |
| 629 | 4-Cl—Ph—CH₂— | 2-C2H5—Ph |
| 630 | 4-Cl—Ph—CH₂— | 2-iPr—Ph |
| 631 | 4-Cl—Ph—CH₂— | 2-tBu—Ph |
| 632 | 4-Cl—Ph—CH₂— | 2-Ph—Ph |
| 633 | 4-Cl—Ph—CH₂— | 2-CH2Ph—Ph |
| 634 | 4-Cl—Ph—CH₂— | 2-CH2CO2Me—Ph |
| 635 | 4-Cl—Ph—CH₂— | 2-(1-piperidinyl)-Ph |
| 636 | 4-Cl—Ph—CH₂— | 2-(1-pyrrolidinyl)-Ph |
| 637 | 4-Cl—Ph—CH₂— | 2-(2-imidazolyl)-Ph |
| 638 | 4-Cl—Ph—CH₂— | 2-(1-imidazolyl)-Ph |
| 639 | 4-Cl—Ph—CH₂— | 2-(2-thiazolyl)-Ph |
| 640 | 4-Cl—Ph—CH₂— | 2-(3-pyrazolyl)-Ph |
| 641 | 4-Cl—Ph—CH₂— | 2-(1-pyrazolyl)-Ph |
| 642 | 4-Cl—Ph—CH₂— | 2-(1-tetrazolyl)-Ph |
| 643 | 4-Cl—Ph—CH₂— | 2-(5-tetrazolyl)-Ph |
| 644 | 4-Cl—Ph—CH₂— | 2-(2-pyridyl)-Ph |
| 645 | 4-Cl—Ph—CH₂— | 2-(2-thienyl)-Ph |
| 646 | 4-Cl—Ph—CH₂— | 2-(2-furanyl)-Ph |
| 647 | 4-Cl—Ph—CH₂— | 2,4-diF—Ph |
| 648 | 4-Cl—Ph—CH₂— | 2,5-diF—Ph |
| 649 | 4-Cl—Ph—CH₂— | 2,6-diF—Ph |
| 650 | 4-Cl—Ph—CH₂— | 3,4-diF—Ph |
| 651 | 4-Cl—Ph—CH₂— | 3,5-diF—Ph |
| 652 | 4-Cl—Ph—CH₂— | 2,4-diCl—Ph |
| 653 | 4-Cl—Ph—CH₂— | 2,5-diCl—Ph |
| 654 | 4-Cl—Ph—CH₂— | 2,6-diCl—Ph |
| 655 | 4-Cl—Ph—CH₂— | 3,4-diCl—Ph |

TABLE 2*-continued

| | | |
|---|---|---|
| 656 | 4-Cl—Ph—CH$_2$— | 3,5-diCl—Ph |
| 657 | 4-Cl—Ph—CH$_2$— | 3,4-diCF3—Ph |
| 658 | 4-Cl—Ph—CH$_2$— | 3,5-diCF3—Ph |
| 659 | 4-Cl—Ph—CH$_2$— | 5-Cl-2-MeO—Ph |
| 660 | 4-Cl—Ph—CH$_2$— | 5-Cl-2-Me—Ph |
| 661 | 4-Cl—Ph—CH$_2$— | 2-F-5-Me—Ph |
| 662 | 4-Cl—Ph—CH$_2$— | 2-F-5-NO2—Ph |
| 663 | 4-Cl—Ph—CH$_2$— | 3,4-OCH2O—Ph |
| 664 | 4-Cl—Ph—CH$_2$— | 3,4-OCH2CH2O—Ph |
| 665 | 4-Cl—Ph—CH$_2$— | 2-MeO-4-Me—Ph |
| 666 | 4-Cl—Ph—CH$_2$— | 2-MeO-5-Me—Ph |
| 667 | 4-Cl—Ph—CH$_2$— | 1-naphthyl |
| 668 | 4-Cl—Ph—CH$_2$— | 2-naphthyl |
| 669 | 4-Cl—Ph—CH$_2$— | 2-thienyl |
| 670 | 4-Cl—Ph—CH$_2$— | 3-thienyl |
| 671 | 4-Cl—Ph—CH$_2$— | 2-furanyl |
| 672 | 4-Cl—Ph—CH$_2$— | 3-furanyl |
| 673 | 4-Cl—Ph—CH$_2$— | 2-pyridyl |
| 674 | 4-Cl—Ph—CH$_2$— | 3-pyridyl |
| 675 | 4-Cl—Ph—CH$_2$— | 4-pyridyl |
| 676 | 4-Cl—Ph—CH$_2$— | 2-indolyl |
| 677 | 4-Cl—Ph—CH$_2$— | 3-indolyl |
| 678 | 4-Cl—Ph—CH$_2$— | 5-indolyl |
| 679 | 4-Cl—Ph—CH$_2$— | 6-indolyl |
| 680 | 4-Cl—Ph—CH$_2$— | 3-indazolyl |
| 681 | 4-Cl—Ph—CH$_2$— | 5-indazolyl |
| 682 | 4-Cl—Ph—CH$_2$— | 6-indazolyl |
| 683 | 4-Cl—Ph—CH$_2$— | 2-imidazolyl |
| 684 | 4-Cl—Ph—CH$_2$— | 3-pyrazolyl |
| 685 | 4-Cl—Ph—CH$_2$— | 2-thiazolyl |
| 686 | 4-Cl—Ph—CH$_2$— | 5-tetrazolyl |
| 687 | 4-Cl—Ph—CH$_2$— | 2-benzimidazolyl |
| 688 | 4-Cl—Ph—CH$_2$— | 5-benzimidazolyl |
| 689 | 4-Cl—Ph—CH$_2$— | 2-benzothiazolyl |
| 690 | 4-Cl—Ph—CH$_2$— | 5-benzothiazolyl |
| 691 | 4-Cl—Ph—CH$_2$— | 2-benzoxazolyl |
| 692 | 4-Cl—Ph—CH$_2$— | 5-benzoxazolyl |
| 693 | 4-Cl—Ph—CH$_2$— | 1-adamantyl |
| 694 | 4-Cl—Ph—CH$_2$— | 2-adamantyl |
| 695 | 4-Cl—Ph—CH$_2$— | t-Bu |
| 696 | 2-Cl—Ph—CH$_2$— | 3-CN—Ph |
| 697 | 2-Cl—Ph—CH$_2$— | 3-COCH3—Ph |
| 698 | 2-Cl—Ph—CH$_2$— | 3-CO2Me—Ph |
| 699 | 2-Cl—Ph—CH$_2$— | 3-CO2Et—Ph |
| 700 | 2-Cl—Ph—CH$_2$— | 3-CO2H—Ph |
| 701 | 2-Cl—Ph—CH$_2$— | 3-CONH2—Ph |
| 702 | 2-Cl—Ph—CH$_2$— | 3-F—Ph |
| 703 | 2-Cl—Ph—CH$_2$— | 3-Cl—Ph |
| 704 | 2-Cl—Ph—CH$_2$— | 3-NH2—Ph |
| 705 | 2-Cl—Ph—CH$_2$— | 3-SO2NH2—Ph |
| 706 | 2-Cl—Ph—CH$_2$— | 3-CF3—Ph |
| 707 | 2-Cl—Ph—CH$_2$— | 3-OCH3—Ph |
| 708 | 2-Cl—Ph—CH$_2$— | 3-OEt—Ph |
| 709 | 2-Cl—Ph—CH$_2$— | 3-OCF3—Ph |
| 710 | 2-Cl—Ph—CH$_2$— | 3-SO2CH3—Ph |
| 711 | 2-Cl—Ph—CH$_2$— | 3-OH—Ph |
| 712 | 2-Cl—Ph—CH$_2$— | 3-CH3—Ph |
| 713 | 2-Cl—Ph—CH$_2$— | 3-C2H5—Ph |
| 714 | 2-Cl—Ph—CH$_2$— | 4-CN—Ph |
| 715 | 2-Cl—Ph—CH$_2$— | 4-COCH3—Ph |
| 716 | 2-Cl—Ph—CH$_2$— | 4-CO2Me—Ph |
| 717 | 2-Cl—Ph—CH$_2$— | 4-CO2Et—Ph |
| 718 | 2-Cl—Ph—CH$_2$— | 4-CO2H—Ph |
| 719 | 2-Cl—Ph—CH$_2$— | 4-CONH2—Ph |
| 720 | 2-Cl—Ph—CH$_2$— | 4-F—Ph |
| 721 | 2-Cl—Ph—CH$_2$— | 4-Cl—Ph |
| 722 | 2-Cl—Ph—CH$_2$— | 4-NH2—Ph |
| 723 | 2-Cl—Ph—CH$_2$— | 4-SO2NH2—Ph |
| 724 | 2-Cl—Ph—CH$_2$— | 4-CF3—Ph |
| 725 | 2-Cl—Ph—CH$_2$— | 4-OCH3—Ph |
| 726 | 2-Cl—Ph—CH$_2$— | 4-OEt—Ph |
| 727 | 2-Cl—Ph—CH$_2$— | 4-OCF3—Ph |
| 728 | 2-Cl—Ph—CH$_2$— | 4-SO2CH3—Ph |
| 729 | 2-Cl—Ph—CH$_2$— | 4-OH—Ph |
| 730 | 2-Cl—Ph—CH$_2$— | 4-CH3—Ph |
| 731 | 2-Cl—Ph—CH$_2$— | 4-C2H5—Ph |
| 732 | 2-Cl—Ph—CH$_2$— | 2,4-diF—Ph |
| 733 | 2-Cl—Ph—CH$_2$— | 2,5-diF—Ph |
| 734 | 2-Cl—Ph—CH$_2$— | 3,4-diF—Ph |
| 735 | 2-Cl—Ph—CH$_2$— | 3,5-diF—Ph |
| 736 | 2-Cl—Ph—CH$_2$— | 2,4-diCl—Ph |
| 737 | 2-Cl—Ph—CH$_2$— | 2,5-diCl—Ph |
| 738 | 2-Cl—Ph—CH$_2$— | 3,4-diCl—Ph |
| 739 | 2-Cl—Ph—CH$_2$— | 3,5-diCl—Ph |
| 740 | 2-Cl—Ph—CH$_2$— | 3,4-OCH2O—Ph |
| 741 | 2-Cl—Ph—CH$_2$— | 3,4-OCH2CH2O—Ph |
| 742 | 2-Cl—Ph—CH$_2$— | 2-thienyl |
| 743 | 2-Cl—Ph—CH$_2$— | 2-furanyl |
| 744 | 2-Cl—Ph—CH$_2$— | 2-pyridyl |
| 745 | 2-Cl—Ph—CH$_2$— | 4-pyridyl |
| 746 | 2-Cl—Ph—CH$_2$— | 2-imidazoilyl |
| 747 | 2-Cl—Ph—CH$_2$— | 3-pyrazolyl |
| 748 | 2-Cl—Ph—CH$_2$— | 2-thiazolyl |
| 749 | 2-Cl—Ph—CH$_2$— | 5-tetrazolyl |
| 750 | 2-Cl—Ph—CH$_2$— | 1-adamantyl |
| 751 | 2,4-diCl—Ph—CH$_2$— | 3-CN—Ph |
| 752 | 2,4-diCl—Ph—CH$_2$— | 3-COCH3—Ph |
| 753 | 2,4-diCl—Ph—CH$_2$— | 3-CO2Me—Ph |
| 754 | 2,4-diCl—Ph—CH$_2$— | 3-CO2Et—Ph |
| 755 | 2,4-diCl—Ph—CH$_2$— | 3-CO2H—Ph |
| 756 | 2,4-diCl—Ph—CH$_2$— | 3-CONH2—Ph |
| 757 | 2,4-diCl—Ph—CH$_2$— | 3-F—Ph |
| 758 | 2,4-diCl—Ph—CH$_2$— | 3-Cl—Ph |
| 759 | 2,4-diCl—h—CH$_2$— | 3-NE2—Ph |
| 760 | 2,4-diCl—Ph—CH$_2$— | 3-SO2NH2—Ph |
| 761 | 2,4-diCl—Ph—CH$_2$— | 3-CF3—Ph |
| 762 | 2,4-diCl—Ph—CH$_2$— | 3-OCH3—Ph |
| 763 | 2,4-diCl—Ph—CH$_2$— | 3-OEt—Ph |
| 764 | 2,4-diCl—Ph—CH$_2$— | 3-OCF3—Ph |
| 765 | 2,4-diCl—Ph—CH$_2$— | 3-SO2CH3—Ph |
| 766 | 2,4-diCl—Ph—CH$_2$— | 3-OH—Ph |
| 767 | 2,4-diCl—Ph—CH$_2$— | 3-CH3—Ph |
| 768 | 2,4-diCl—Ph—CH$_2$— | 3-C2H5—Ph |
| 769 | 2,4-diCl—Ph—CH$_2$— | 4-CN—Ph |
| 770 | 2,4-diCl—Ph—CH$_2$— | 4-COCH3—Ph |
| 771 | 2,4-diCl—Ph—CH$_2$— | 4-CO2Me—Ph |
| 772 | 2,4-diCl—Ph—CH$_2$— | 4-CO2Et—Ph |
| 773 | 2,4-diCl—Ph—CH$_2$— | 4-CO2H—Ph |
| 774 | 2,4-diCl—Ph—CH$_2$— | 4-CONH2—Ph |
| 775 | 2,4-diCl—Ph—CH$_2$— | 4-F—Ph |
| 776 | 2,4-diCl—Ph—CH$_2$— | 4-Cl—Ph |
| 777 | 2,4-diCl—Ph—CH$_2$— | 4-NH2—Ph |
| 778 | 2,4-diCl—Ph—CH$_2$— | 4-SO2NH2—Ph |
| 779 | 2,4-diCl—Ph—CH$_2$— | 4-CF3—Ph |
| 780 | 2,4-diCl—Ph—CH$_2$— | 4-OCH3—Ph |
| 781 | 2,4-diCl—Ph—CH$_2$— | 4-OEt—Ph |
| 782 | 2,4-diCl—Ph—CH$_2$— | 4-OCF3—Ph |
| 783 | 2,4-diCl—Ph—CH$_2$— | 4-SO2CH3—Ph |
| 784 | 2,4-diCl—Ph—CH$_2$— | 4-OH—Ph |
| 785 | 2,4-diCl—Ph—CH$_2$— | 4-CH3—Ph |
| 786 | 2,4-diCl—Ph—CH$_2$— | 4-C2H5—Ph |
| 787 | 2,4-diCl—Ph—CH$_2$— | 2,4-diF—Ph |
| 788 | 2,4-diCl—Ph—CH$_2$— | 2,5-diF—Ph |
| 789 | 2,4-diCl—Ph—CH$_2$— | 3,4-diF—Ph |
| 790 | 2,4-diCl—Ph—CH$_2$— | 3,5-diF—Ph |
| 791 | 2,4-diCl—Ph—CH$_2$— | 2,4-diCl—Ph |
| 792 | 2,4-diCl—Ph—CH$_2$— | 2,5-diCl—Ph |
| 793 | 2,4-diCl—Ph—CH$_2$— | 3,4-diCl—Ph |
| 794 | 2,4-diCl—Ph—CH$_2$— | 3,5-diCl—Ph |
| 795 | 2,4-diCl—Ph—CH$_2$— | 3,4-OCH2O—Ph |
| 796 | 2,4-diCl—Ph—CH$_2$— | 3,4-OCH2CH2O—Ph |
| 797 | 2,4-diCl—Ph—CH$_2$— | 2-thienyl |
| 798 | 2,4-diCl—Ph—CH$_2$— | 2-furanyl |
| 799 | 2,4-diCl—Ph—CH$_2$— | 2-pyridyl |
| 800 | 2,4-diCl—Ph—CH$_2$— | 4-pyridyl |
| 801 | 2,4-diCl—Ph—CH$_2$— | 2-imidazolyl |
| 802 | 2,4-diCl—Ph—CH$_2$— | 3-pyrazolyl |
| 803 | 2,4-diCl—Ph—CH$_2$— | 2-thiazolyl |
| 804 | 2,4-diCl—Ph—CH$_2$— | 5-tetrazolyl |
| 805 | 2,4-diCl—Ph—CH$_2$— | 1-adamantyl |
| 806 | 3-OCH3—Ph—CH$_2$— | 3-CN—Ph |
| 807 | 3-OCH3—Ph—CH$_2$— | 3-COCH3—Ph |
| 808 | 3-OCH3—Ph—CH$_2$— | 3-CO2Me—Ph |
| 809 | 3-OCH3—Ph—CH$_2$— | 3-CO2Et—Ph |
| 810 | 3-OCH3—Ph—CH$_2$— | 3-CO2H—Ph |
| 811 | 3-OCH3—Ph—CH$_2$— | 3-CONH2—Ph |
| 812 | 3-OCH3—Ph—CH$_2$— | 3-F—Ph |
| 813 | 3-OCH3—Ph—CH$_2$— | 3-Cl—Ph |

TABLE 2*-continued

| | | |
|---|---|---|
| 814 | 3-OCH3—Ph—CH₂— | 3-NH2—Ph |
| 815 | 3-OCH3—Ph—CH₂— | 3-SO2NH2—Ph |
| 816 | 3-OCH3—Ph—CH₂— | 3-CF3—Ph |
| 817 | 3-OCH3—Ph—CH₂— | 3-OCH3—Ph |
| 818 | 3-OCH3—Ph—CH₂— | 3-OEt—Ph |
| 819 | 3-OCH3—Ph—CH₂— | 3-OCF3—Ph |
| 820 | 3-OCH3—Ph—CH₂— | 3-SO2CH3—Ph |
| 821 | 3-OCH3—Ph—CH₂— | 3-OH—Ph |
| 822 | 3-OCH3—Ph—CH₂— | 3-CH3—Ph |
| 823 | 3-OCH3—Ph—CH₂— | 3-C2H5—Ph |
| 824 | 3-OCH3—Ph—CH₂— | 4-CN—Ph |
| 825 | 3-OCH3—Ph—CH₂— | 4-COCH3—Ph |
| 826 | 3-OCH3—Ph—CH₂— | 4-CO2Me—Ph |
| 827 | 3-OCH3—Ph—CH₂— | 4-CO2Et—Ph |
| 828 | 3-OCH3—Ph—CH₂— | 4-CO2H—Ph |
| 829 | 3-OCH3—Ph—CH₂— | 4-cONH2—Ph |
| 830 | 3-OCH3—Ph—CH₂— | 4-F—Ph |
| 831 | 3-OCH3—Ph—CH₂— | 4-Cl—Ph |
| 832 | 3-OCH3—Ph—CH₂— | 4-NH2—Ph |
| 833 | 3-OCH3—Ph—CH₂— | 4-SO2NH2—Ph |
| 834 | 3-OCH3—Ph—CH₂— | 4-CF3—Ph |
| 835 | 3-OCH3—Ph—CH₂— | 4-OCH3—Ph |
| 836 | 3-OCH3—Ph—CH₂— | 4-OEt—Ph |
| 837 | 3-OCH3—Ph—CH₂— | 4-OCF3—Ph |
| 838 | 3-OCH3—Ph—CH₂— | 4-SO2CH3—Ph |
| 839 | 3-OCH3—Ph—CH₂— | 4-OH—Ph |
| 840 | 3-OCH3—Ph—CH₂— | 4-CH3—Ph |
| 841 | 3-OCH3—Ph—CH₂— | 4-C2H5—Ph |
| 842 | 3-OCH3—Ph—CH₂— | 2,4-diF—Ph |
| 843 | 3-OCH3—Ph—CH₂— | 2,5-diF—Ph |
| 844 | 3-OCH3—Ph—CH₂— | 3,4-diF—Ph |
| 845 | 3-OCH3—Ph—CH₂— | 3,5-diF—Ph |
| 846 | 3-OCH3—Ph—CH₂— | 2,4-diCl—Ph |
| 847 | 3-OCH3—Ph—CH₂— | 2,5-diCl—Ph |
| 848 | 3-OCH3—Ph—CH₂— | 3,4-diCl—Ph |
| 849 | 3-OCH3—Ph—CH₂— | 3,5-diCl—Ph |
| 850 | 3-OCH3—Ph—CH₂— | 3,4-OCH2O—Ph |
| 851 | 3-OCH3—Ph—CH₂— | 3,4-OCH2CH2O—Ph |
| 852 | 3-OCH3—Ph—CH₂— | 2-thienyl |
| 853 | 3-OCH3—Ph—CH₂— | 2-furanyl |
| 854 | 3-OCH3—Ph—CH₂— | 2-pyridyl |
| 855 | 3-OCH3—Ph—CH₂— | 4-pyridyl |
| 856 | 3-OCH3—Ph—CH₂— | 2-imidazolyl |
| 857 | 3-OCH3—Ph—CH₂— | 3-pyrazolyl |
| 858 | 3-OCH3—Ph—CH₂— | 2-thiazolyl |
| 859 | 3-OCH3—Ph—CH₂— | 5-tetrazolyl |
| 860 | 3-OCH3—Ph—CH₂— | 1-adamantyl |
| 861 | 2-thieylethyl | 3-CN—Ph |
| 862 | 2-thieylmethyl | 3-COCH3—Ph |
| 863 | 2-thienylmethyl | 3-F—Ph |
| 864 | 2-thienylmethyl | 3-Cl—Ph |
| 865 | 2-thienylmethyl | 3-NH2—Ph |
| 866 | 2-thienylmethyl | 3-OCH3—Ph |
| 867 | 2-thienylmethyl | 3-OH—Ph |
| 868 | 2-thienylmethyl | 4-CN—Ph |
| 869 | 2-thienylmethyl | 4-COCH3—Ph |
| 870 | 2-thienylmethyl | 4-F—Ph |
| 871 | 2-thienylmethyl | 4-Cl—Ph |
| 872 | 2-thienylmethyl | 4-NH2—Ph |
| 873 | 2-thienylmethyl | 4-OCH3—Ph |
| 874 | 2-thienylmethyl | 4-OH—Ph |
| 875 | 2-thienylmethyl | 3,4-diF—Ph |
| 876 | 2-thienylmethyl | 3,5-diF—Ph |
| 877 | 2-thienylmethyl | 3,4-diCl—Ph |
| 878 | 2-thienylmethyl | 3,5-diCl—Ph |
| 879 | 2-thienylmethyl | 3,4-OCH2O—Ph |
| 880 | 2-thienylmethyl | 3,4-OCH2CH2O—Ph |
| 881 | 3-thienylmethyl | 3-CN—Ph |
| 882 | 3-thienylmethyl | 3-COCH3—Ph |
| 883 | 3-thienylmethyl | 3-F—Ph |
| 884 | 3-thienylmethyl | 3-Cl—Ph |
| 885 | 3-thienylmethyl | 3-NH2—Ph |
| 886 | 3-thienylmethyl | 3-OCH3—Ph |
| 887 | 3-thienylmethyl | 3-OH—Ph |
| 888 | 3-thienylmethyl | 4-CN—Ph |
| 889 | 3-thienylmethyl | 4-COCH3—Ph |
| 890 | 3-thienylmethyl | 4-F—Ph |
| 891 | 3-thienylmethyl | 4-Cl—Ph |
| 892 | 3-thienylmethyl | 4-NH2—Ph |
| 893 | 3-thienylmethyl | 4-OCH3—Ph |
| 894 | 3-thienylmethyl | 4-OH—Ph |
| 895 | 3-thienylmethyl | 3,4-diF—Ph |
| 896 | 3-thienylmethyl | 3,5-diF—Ph |
| 897 | 3-thienylmethyl | 3,4-diCl—Ph |
| 898 | 3-thienylmethyl | 3,5-diCl—Ph |
| 899 | 3-thienylmethyl | 3,4-OCH2O—Ph |
| 900 | 3-thienylmethyl | 3,4-OCH2CH2O—Ph |
| 901 | 2-furanylmethyl | 3-CN—Ph |
| 902 | 2-furanylmethyl | 3-COCH3—Ph |
| 903 | 2-furanylmethyl | 3-F—Ph |
| 904 | 2-furanylmethyl | 3-Cl—Ph |
| 905 | 2-furanylmethyl | 3-NH2—Ph |
| 906 | 2-furanylmethyl | 3-OCH3—Ph |
| 907 | 2-furanylmethyl | 3-OH—Ph |
| 908 | 2-furanylmethyl | 4-CN—Ph |
| 909 | 2-furanylmethyl | 4-COCH3—Ph |
| 910 | 2-furanylmethyl | 4-F—Ph |
| 911 | 2-furanylmethyl | 4-Cl—Ph |
| 912 | 2-furanylmethyl | 4-NH2—Ph |
| 913 | 2-furanylmethyl | 4-OCH3—Ph |
| 914 | 2-furanylmethyl | 4-OH—Ph |
| 915 | 2-furanylmethyl | 3,4-diF—Ph |
| 916 | 2-furanylmethyl | 3,5-diF—Ph |
| 917 | 2-furanylmethyl | 3,4-diCl—Ph |
| 918 | 2-furanylmethyl | 3,5-diCl—Ph |
| 919 | 2-furanylmethyl | 3,4-OCH2O—Ph |
| 920 | 2-furanylmethyl | 3,4-OCH2CH2O—Ph |
| 921 | 3-furanylmethyl | 3-CN—Ph |
| 922 | 3-furanylmethyl | 3-COCH3—Ph |
| 923 | 3-furanylmethyl | 3-F—Ph |
| 924 | 3-furanylmethyl | 3-Cl—Ph |
| 925 | 3-furanylmethyl | 3-NH2—Ph |
| 926 | 3-furanylmethyl | 3-OCH3—Ph |
| 927 | 3-furanylmethyl | 3-OH—Ph |
| 928 | 3-furanylmethyl | 4-CN—Ph |
| 929 | 3-furanylmethyl | 4-COCH3—Ph |
| 930 | 3-furanylmethyl | 4-F—Ph |
| 931 | 3-furanylmethyl | 4-Cl—Ph |
| 932 | 3-furanylmethyl | 4-NH2—Ph |
| 933 | 3-furanylmethyl | 4-OCH3—Ph |
| 934 | 3-furanylmethyl | 4-OH—Ph |
| 935 | 3-furanylmethyl | 3,4-diF—Ph |
| 936 | 3-furanylmethyl | 3,5-diF—Ph |
| 937 | 3-furanylmethyl | 3,4-diCl—Ph |
| 938 | 3-furanylmethyl | 3,5-diCl—Ph |
| 939 | 3-furanylmethyl | 3,4-OCH2O—Ph |
| 940 | 3-furanylmethyl | 3,4-OCH2CH2O—Ph |
| 941 | 2-pyridylmethyl | 3-CN—Ph |
| 942 | 2-pyridylmethyl | 3-COCH3—Ph |
| 943 | 2-pyridylmethyl | 3-F—Ph |
| 944 | 2-pyridylmethyl | 3-Cl—Ph |
| 945 | 2-pyridylmethyl | 3-NH2—Ph |
| 946 | 2-pyridylmethyl | 3-OCH3—Ph |
| 947 | 2-pyridylmethyl | 3-OH—Ph |
| 948 | 2-pyridylmethyl | 4-CN—Ph |
| 949 | 2-pyridylmethyl | 4-COCH3—Ph |
| 950 | 2-pyridylmethyl | 4-F—Ph |
| 951 | 2-pyridylmethyl | 4-Cl—Ph |
| 952 | 2-pyridylmethyl | 4-NH2—Ph |
| 953 | 2-pyridylmethyl | 4-OCH3—Ph |
| 954 | 2-pyridylmethyl | 4-OH—Ph |
| 955 | 2-pyridylmethyl | 3,4-diF—Ph |
| 956 | 2-pyridylmethyl | 3,5-diF—Ph |
| 957 | 2-pyridylmethyl | 3,4-diCl—Ph |
| 958 | 2-pyridylmethyl | 3,5-diCl—Ph |
| 959 | 2-pyridylmethyl | 3,4-OCH2O—Ph |
| 960 | 2-pyridylmethyl | 3,4-OCH2CH2O—Ph |
| 961 | 3-pyridylmethyl | 3-CN—Ph |
| 962 | 3-pyridylmethyl | 3-COCH3—Ph |
| 963 | 3-pyridylmethyl | 3-F—Ph |
| 964 | 3-pyridylmethyl | 3-Cl—Ph |
| 965 | 3-pyridylmethyl | 3-NH2—Ph |
| 966 | 3-pyridylmethyl | 3-OCH3—Ph |
| 967 | 3-pyridylmethyl | 3-OH—Ph |
| 968 | 3-pyridylmethyl | 4-CN—Ph |
| 969 | 3-pyridylmethyl | 4-COCH3—Ph |
| 970 | 3-pyridylmethyl | 4-F—Ph |
| 971 | 3-pyridylmethyl | 4-Cl—Ph |

TABLE 2*-continued

| | | |
|---|---|---|
| 972 | 3-pyridylmethyl | 4-NH2—Ph |
| 973 | 3-pyridylmethyl | 4-OCH3—Ph |
| 974 | 3-pyridylmethyl | 4-OH—Ph |
| 975 | 3-pyridylmethyl | 3,4-diF—Ph |
| 976 | 3-pyridylmethyl | 3,5-diF—Ph |
| 977 | 3-pyridylmethyl | 3,4-diCl—Ph |
| 978 | 3-pyridylmethyl | 3,5-diCl—Ph |
| 979 | 3-pyridylmethyl | 3,4-OCH2O—Ph |
| 980 | 3-pyridylmethyl | 3,4-OCH2CH2O—Ph |
| 981 | 4-pyridylmethyl | 3-CN—Ph |
| 982 | 4-pyridylmethyl | 3-COCH3—Ph |
| 983 | 4-pyridylmethyl | 3-F—Ph |
| 984 | 4-pyridylmethyl | 3-Cl—Ph |
| 985 | 4-pyridylmethyl | 3-NH2—Ph |
| 986 | 4-pyridylmethyl | 3-OCH3—Ph |
| 987 | 4-pyridylmethyl | 3-OH—Ph |
| 988 | 4-pyridylmethyl | 4-CN—Ph |
| 989 | 4-pyridylmethyl | 4-COCH3—Ph |
| 990 | 4-pyridylmethyl | 4-F—Ph |
| 991 | 4-pyridylmethyl | 4-Cl—Ph |
| 992 | 4-pyridylmethyl | 4-NH2—Ph |
| 993 | 4-pyridylmethyl | 4-OCH3—Ph |
| 994 | 4-pyridylmethyl | 4-OH—Ph |
| 995 | 4-pyridylmethyl | 3,4-diF—Ph |
| 996 | 4-pyridylmethyl | 3,5-diF—Ph |
| 997 | 4-pyridylmethyl | 3,4-diCl—Ph |
| 998 | 4-pyridylmethyl | 3,5-diCl—Ph |
| 999 | 4-pyridylmethyl | 3,4-OCH2O—Ph |
| 1000 | 4-pyridylmethyl | 3,4-OCH2CH2O—Ph |
| 1001 | 3-indolylmethyl | 3-CN—Ph |
| 1002 | 3-indolylmethyl | 3-COCH3—Ph |
| 1003 | 3-indolylmethyl | 3-F—Ph |
| 1004 | 3-indolylmethyl | 3-Cl—Ph |
| 1005 | 3-indolylmethyl | 3-NH2—Ph |
| 1006 | 3-indolylmethyl | 3-OCH3—Ph |
| 1007 | 3-indolylmethyl | 3-OH—Ph |
| 1008 | 3-indolylmethyl | 4-CN—Ph |
| 1009 | 3-indolylmethyl | 4-COCH3—Ph |
| 1010 | 3-indolylmethyl | 4-F—Ph |
| 1011 | 3-indolylmethyl | 4-Cl—Ph |
| 1012 | 3-indolylmethyl | 4-NH2—Ph |
| 1013 | 3-indolylmethyl | 4-OCH3—Ph |
| 1014 | 3-indolylmethyl | 4-OH—Ph |
| 1015 | 3-indolylmethyl | 3,4-diF—Ph |
| 1016 | 3-indolylmethyl | 3,5-diF—Ph |
| 1017 | 3-indolylmethyl | 3,4-diCl—Ph |
| 1018 | 3-indolylmethyl | 3,5-diCl—Ph |
| 1019 | 3-indolylmethyl | 3,4-OCH2O—Ph |
| 1020 | 3-indolylmethyl | 3,4-OCH2CH2O—Ph |
| 1021 | 5-indolylmethyl | 3-CN—Ph |
| 1022 | 5-indolylmethyl | 3-COCH3—Ph |
| 1023 | 5-indolylmethyl | 3-F—Ph |
| 1024 | 5-indolylmethyl | 3-Cl—Ph |
| 1025 | 5-indolylmethyl | 3-NH2—Ph |
| 1026 | 5-indolylmethyl | 3-OCH3—Ph |
| 1027 | 5-indolylmethyl | 3-OH—Ph |
| 1028 | 5-indolylmethyl | 4-CN—Ph |
| 1029 | 5-indolylmethyl | 4-COCH3—Ph |
| 1030 | 5-indolylmethyl | 4-F—Ph |
| 1031 | 5-indolylmethyl | 4-Cl—Ph |
| 1032 | 5-indolylmethyl | 4-NH2—Ph |
| 1033 | 5-indolylmethyl | 4-OCH3—Ph |
| 1034 | 5-indolylmethyl | 4-OH—Ph |
| 1035 | 5-indolylmethyl | 3,4-diF—Ph |
| 1036 | 5-indolylmethyl | 3,5-diF—Ph |
| 1037 | 5-indolylmethyl | 3,4-diCl—Ph |
| 1038 | 5-indolylmethyl | 3,5-diCl—Ph |
| 1039 | 5-indolylmethyl | 3,4-OCH2O—Ph |
| 1040 | 5-indolylmethyl | 3,4-OCH2CH2O—Ph |
| 1041 | 5-indazolylmethyl | 3-CN—Ph |
| 1042 | 5-indazolylmethyl | 3-COCH3—Ph |
| 1043 | 5-indazolylmethyl | 3-F—Ph |
| 1044 | 5-indazolylmethyl | 3-Cl—Ph |
| 1045 | 5-indazolylmethyl | 3-NH2—Ph |
| 1046 | 5-indazolylmethyl | 3-OCH3—Ph |
| 1047 | 5-indazolylmethyl | 3-OH—Ph |
| 1048 | 5-indazolylmethyl | 4-CN—Ph |
| 1049 | 5-indazolylmethyl | 4-COCH3—Ph |
| 1050 | 5-indazolylmethyl | 4-F—Ph |
| 1051 | 5-indazolylmethyl | 4-Cl—Ph |
| 1052 | 5-indazolylmethyl | 4-NH2—Ph |
| 1053 | 5-indazolylmethyl | 4-OCH3—Ph |
| 1054 | 5-indazolylmethyl | 4-OH—Ph |
| 1055 | 5-indazolylmethyl | 3,4-diF—Ph |
| 1056 | 5-indazolylmethyl | 3,5-diF—Ph |
| 1057 | 5-indazolylmethyl | 3,4-diCl—Ph |
| 1058 | 5-indazolylmethyl | 3,5-diCl—Ph |
| 1059 | 5-indazolylmethyl | 3,4-OCH2O—Ph |
| 1060 | 5-indazolylmethyl | 3,4-OCH2CH2O—Ph |
| 1061 | 5-benzimidazolylmethyl | 3-CN—Ph |
| 1062 | 5-benzimidazolylmethyl | 3-COCH3—Ph |
| 1063 | 5-benzimidazolylmethyl | 3-F—Ph |
| 1064 | 5-benzimidazolylmethyl | 3-Cl—Ph |
| 1065 | 5-benzimidazolylmethyl | 3-NH2—Ph |
| 1066 | 5-benzimidazolylmethyl | 3-OCH3—Ph |
| 1067 | 5-benzimidazolylmethyl | 3-OH—Ph |
| 1068 | 5-benzimidazolylmethyl | 4-CN—Ph |
| 1069 | 5-benzimidazolylmethyl | 4-COCH3—Ph |
| 1070 | 5-benzimidazolylmethyl | 4-F—Ph |
| 1071 | 5-benzimidazolylmethyl | 4-Cl—Ph |
| 1072 | 5-benzimidazolylmethyl | 4-NH2—Ph |
| 1073 | 5-benzimidazolylmethyl | 4-OCH3—Ph |
| 1074 | 5-benzimidazolylmethyl | 4-OH—Ph |
| 1075 | 5-benzimidazolylmethyl | 3,4-diF—Ph |
| 1076 | 5-benzimidazolylmethyl | 3,5-diF—Ph |
| 1077 | 5-benzimidazolylmethyl | 3,4-diCl—Ph |
| 1078 | 5-benzimidazolylmethyl | 3,5-diCl—Ph |
| 1079 | 5-benzimidazolylmethyl | 3,4-OCH2O—Ph |
| 1080 | 5-benzimidazolylmethyl | 3,4-OCH2CH2O—Ph |
| 1081 | 5-benzimidazolylmethyl | 3-CN—Ph |
| 1082 | 5-benzimidazolylmethyl | 3-COCH3—Ph |
| 1083 | 5-benzimidazolylmethyl | 3-F—Ph |
| 1084 | 5-benzimidazolylmethyl | 3-Cl—Ph |
| 1085 | 5-benzimidazolylmethyl | 3-NH2—Ph |
| 1086 | 5-benzimidazolylmethyl | 3-OCH3—Ph |
| 1087 | 5-benzimidazolylmethyl | 3-OH—Ph |
| 1088 | 5-benzimidazolylmethyl | 4-CN—Ph |
| 1089 | 5-benzimidazolylmethyl | 4-COCH3—Ph |
| 1090 | 5-benzimidazolylmethyl | 4-F—Ph |
| 1091 | 5-benzimidazolylmethyl | 4-Cl—Ph |
| 1092 | 5-benzimidazolylmethyl | 4-NH2—Ph |
| 1093 | 5-benzimidazolylmethyl | 4-OCH3—Ph |
| 1094 | 5-benzimidazolylmethyl | 4-OH—Ph |
| 1095 | 5-benzimidazolylmethyl | 3,4-diF—Ph |
| 1096 | 5-benzimidazolylmethyl | 3,5-diF—Ph |
| 1097 | 5-benzimidazolylmethyl | 3,4-diCl—Ph |
| 1098 | 5-benzimidazolylmethyl | 3,5-diCl—Ph |
| 1099 | 5-benzimidazolylmethyl | 3,4-OCH2O—Ph |
| 1100 | 5-benzimidazolylmethyl | 3,4-OCH2CH2O—Ph |
| 1101 | 5-benzimidazolylmethyl | 3-CN—Ph |
| 1102 | 5-benzimidazolylmethyl | 3-COCH3—Ph |
| 1103 | 5-benzimidazolylmethyl | 3-F—Ph |
| 1104 | 5-benzimidazolylmethyl | 3-Cl—Ph |
| 1105 | 5-benzimidazolylmethyl | 3-NH2—Ph |
| 1106 | 5-benzimidazolylmethyl | 3-OCH3—Ph |
| 1107 | 5-benzimidazolylmethyl | 3-OH—Ph |
| 1108 | 5-benzimidazolylmethyl | 4-CN—Ph |
| 1109 | 5-benzimidazolylmethyl | 4-COCH3—Ph |
| 1110 | 5-benzimidazolylmethyl | 4-F—Ph |
| 1111 | 5-benzimidazolylmethyl | 4-Cl—Ph |
| 1112 | 5-benzimidazolylmethyl | 4-NH2—Ph |
| 1113 | 5-benzimidazolylmethyl | 4-OCH3—Ph |
| 1114 | 5-benzimidazolylmethyl | 4-OH—Ph |
| 1115 | 5-benzimidazolylmethyl | 3,4-diF—Ph |
| 1116 | 5-benzimidazolylmethyl | 3,5-diF—Ph |
| 1117 | 5-benzimidazolylmethyl | 3,4-diCl—Ph |
| 1118 | 5-benzimidazolylmethyl | 3,5-diCl—Ph |
| 1119 | 5-benzimidazolylmethyl | 3,4-OCH2O—Ph |
| 1120 | 5-benzimidazolylmethyl | 3,4-OCH2CH2O—Ph |

*All stereocenters are (+/−) unless otherwise indicated.

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 mM or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 mg/ml protamine in phosphate buffered saline, pH 7.2, for ten minutes at room temperature. Plates are washed three times with phosphate buffered saline and incubated with phosphate buffered saline for thirty minutes at room temperature. For binding, 50 ml of binding buffer (0.5% bovine serum albumen, 20 mM HEPES buffer and 5 mM magnesium chloride in RPMI 1640 media) with or without a test concentration of a compound present at a known concentration is combined with 50 ml of 125-I labeled human eotaxin (to give-a final concentration of 150 pM radioligand) and 50 ml of cell suspension in binding buffer containing $5 \times 10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 mM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA9696-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1 \times 10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 ml volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 mM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migraines (e.g., Toxocara), eosinophilic gastroenteritis (e.g., Anisaki sp., Phocanema sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Preferably, the compounds of the present invention are used to treat or prevent disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

More preferably, the compounds are used to treat or prevent disorders selected from asthma, allergic rhinitis, atopic dermatitis, and inflammatory bowel diseases. Even more preferably, the compounds are used to treat asthma.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention is useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguamides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) anti-viral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula I:

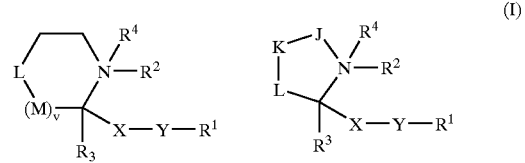

or stereoisomers or pharmaceutically acceptable salts thereof, wherein:

J is selected from $CH_2$ and $CHR^5$;

K and L are independently selected from $CR^5R^6$ and $CR^6R^6$;

with the proviso that at least one of J, K, or L contains an $R^5$;

X is selected from $(CR^{7'}R^{7'})_q$—S—$(CR^{7'}R^{7'})_q$, $(CR^{7'}R^{7'})_q$—O—$(CR^{7'}R^{7'})_q$—$NR^7$—$(CR^{7'}R^{7'})_q$, $(CR^{7'}R^{7'})_r$—C(O)—$(CR^{7'}R^{7'})_q$, $C_{1-6}$ alkylene substituted with 0–5 $R^7$, $C_{2-10}$ alkenylene substituted with 0–5 $R^7$, $C_{2-10}$ alkenylene substituted with 0–5 $R^7$, and $(CR^7R^7)_t$—A—$(CR^7R^7)_t$ substituted with 0–3 $R^8$;

with the proviso that when $R^7$ or $R^{7'}$ is bonded to the same carbon as Y, $R^7$ is not halogen, cyano, or bonded through a heteroatom;

A is $C_{3-6}$ carbocyclic residue;

Y is selected from $NR^{11}C(=O)NR^{11}$, $NR^{11}C(=S)NR^{11}$, $NR^{11}C(=NR^a)NR^{11}$, $NR^{11}C(=CHCN)NR^{11}$, $NR^{11}C(=CHNO_2)NR^{11}$, $NR^{11}C(=C(CN)_2)NR^{11}$, $C(O)$, $S(O)_2NR^{11}$, $NR^{11}S(O)_2$, $NR^{11}S(O)_2NR^{11}$, $C(O)NR^{11}$, $NR^{11}C(O)$, $NR^{11}C(O)O$, and $OC(O)NR^{11}$;

$R^a$ is selected from H, $C_{1-6}$ alkyl, $C_{3-6}$ cycloalkyl, OH, CN, O—$C_{1-6}$ alkyl, and $(CH_2)_w$phenyl;

$R^1$ is selected from a $(CR^{1'}R^{1''})_r$—$C_{3-10}$ carbocyclic residue substituted with 0–5 $R^9$ and a $(CR^{1'}R^{1''})_r$-5–10 membered heterocyclic system containing 1–4 heteroatoms selected from N, O, and S, substituted with 0–3 $R^9$;

$R^{1'}$ and $R^{1''}$, at each occurrence, are selected from H, $C_{1-6}$ alkyl, $(CH_2)_rC_{3-6}$ cycloalkyl, and phenyl;

$R^2$, at each occurrence, is selected from H, $C_{1-8}$ alkyl, $(CR^{2'}R^{2''})_qNR^{12a}R^{12a'}$, $(CR^{2'}R^{2''})_wOH$, $(CR^{2'}R^{2''})_wO(CR^{2'}R^{2''})_rR^{12d}$, $(CR^{2'}R^{2''})_qSH$, $(CR^{2'}R^{2''})_rC(O)H$, $(CR^{2'}R^{2''})_qS(CR^{2'}R^{2''})_rR^{12d}$, $(CR^{2'}R^{2''})_rC(O)OH$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a'}$, $(CR^{2'}R^{2''})_rC(NR^a)NR^{12a}R^{12a'}$, $(CR^{2'}R^{2''})_rC(NR^a)R^{12b}$, $(CR^{2'}R^{2''})_rC(O)NR^{12a}R^{12a'}$, $(CR^{2'}R^{2''})_qNR^{12f}C(O)(CR^{2'}R^{2''})_rR^{12b}$, $(CR^{2'}R^{2''})_rC(O)O(CR^{2'}R^{2''})_rR^{12d}$, $(CR^{2'}R^{2''})_wOC(O)(CR^{2'}R^{2''})_rR^{12b}$, $(CR^{2'}R^{2"})_wS(O)_p(CR^{2'}R^{2"})_rR^{12b}$, $(CR^{2'}R^{2"})_wS(O)_2NR^{12a}R^{12a'}$, $(CR^{2'}R^{2"})_qNR^{12f}S(O)_2(CR^{2'}R^{2"})_rR^{12b}$, $C_{1-6}$ haloalkyl, $C_{2-8}$ alkenyl substituted with 0–3 $R^{12c}$, $C_{2-8}$ alkynyl substituted with 0–3 $R^{12c}$, a $(CR^{2'}R^{2"})_r$—$C_{3-10}$ carbocyclic residue substituted with 0–3 $R^{12c}$, and a $(CH_2)_r$-5–10 membered heterocyclic system containing 1–4 heteroatoms selected from N, O, and S, substituted with 0–2 $R^{12c}$;

alternatively, $R^2$ is an amino acid residue;

$R^{2'}$ and $R^{2"}$, at each occurrence, are selected from H, $C_{1-8}$ alkyl, $C_{2-8}$ alkenyl, $C_{2-8}$ alkynyl, $(CF_2)_rCF_3$, $(CH_2)_rCN$, $(CH_2)_rNO_2$, $(CF_2)_rCF_3$, $(CH_2)_rNR^{2a}R^{2a'}$, $(CH_2)_rOH$, $(CH_2)_rOR^{2b}$, $(CH_2)_rSH$, $(CH_2)_rSR^{2b}$, $(CH_2)_rC(O)OH$, $(CH_2)_rC(O)R^{2b}$, $(CH_2)_rC(O)NR^{2a}R^{2a'}$, $(CH_2)_rNR^{2d}C(O)R^{2a}$, $(CH_2)_rC(O)OR^{2b}$, $(CH_2)_rOC(O)R^{2b}$, $(CH_2)_rS(O)_pR^{2b}$, $(CH_2)_rS(O)_2NR^{2a}R^{2a'}$, $(CH_2)_rNR^{2d}S(O)_2R^{2b}$, $C_{1-6}$ haloalkyl, a $(CR^{2'}R^{2"})_r$—$C_{3-10}$ carbocyclic residue substituted with 0–5 $R^{2c}$, and a $(CH_2)_r$-5–10 membered heterocyclic system containing 1–4 heteroatoms selected from N, O, and S, substituted with 0–2 $R^{2c}$;

$R^{2a}$ and $R^{2a'}$, at each occurrence, are selected from H, $C_{1-6}$ alkyl, $C_{3-6}$ cycloalkyl, and phenyl substituted with 0–3 $R^{2c}$;

$R^{2b}$, at each occurrence, is selected from $C_{1-6}$ alkyl, $C_{3-6}$ cycloalkyl, and phenyl substituted with 0–3 $R^{2c}$;

$R^{2c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{2d}R^{2d}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{2b}$, $(CH_2)_rC(O)NR^{2d}R^{2d}$, $(CH_2)_rNR^{2d}C(O)R^{7a}$, $(CH_2)_rC(O)OC_{1-4}$ alkyl, $(CH_2)_rOC(O)R^{2b}$, $(CH_2)_rC(=NR^{2d})NR^{2d}R^{2d}$, $(CH_2)_rS(O)_pR^{2d}$, $(CH_2)_rNHC(=NR^{2d})NR^{2d}R^{2d}$, $(CH_2)_rS(O)_2NR^{2d}R^{2d}$, $(CH_2)_rNR^{2d}S(O)_2R^{2b}$, and $(CH_2)_r$phenyl substituted with 0–3 $R^{9e}$;

$R^{2d}$, at each occurrence, is selected from H, $C_{1-6}$ alkyl, and $C_{3-6}$ cycloalkyl;

$R^3$ is selected from H, $C_{1-6}$ alkyl, $C_{2-8}$ alkenyl, $C_{2-8}$ alkynyl, $C_{3-6}$ cycloalkyl, $(CF_2)_rCF_3$, $(CH_2)_qNR^{3a}R^{3a'}$, $(CH_2)_qOH$, $(CH_2)_qOR^{3b}$, $(CH_2)_qSH$, $(CH_2)_qSR^{3b}$, $(CH_2)_rC(O)OH$, $(CH_2)_rC(O)R^{3b}$, $(CH_2)_rC(O)NR^{3a}R^{3a'}$, $(CH_2)_rNR^{3d}C(O)R^{3a}$, $(CH_2)_rC(O)OR^{3b}$, $(CH_2)_qOC(O)R^{3b}$, $(CH_2)_rS(O)_pR^{3b}$, $(CH_2)_rS(O)_2NR^{3a}R^{3a'}$, $(CH_2)_qNR^{3d}S(O)_2R^{3b}$, and $(CH_2)_r$-phenyl substituted with 0–3 $R^{3c}$;

$R^{3a}$ and $R^{3a'}$, at each occurrence, are selected from H, $C_{1-6}$ alkyl, $C_{3-6}$ cycloalkyl, and phenyl substituted with 0–3 $R^{3c}$;

$R^{3b}$, at each occurrence, is selected from $C_{1-6}$ alkyl, $C_{3-6}$ cycloalkyl, and phenyl substituted with 0–3 $R^{3c}$;

$R^{3c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{3d}R^{3d}$;

$R^{3d}$, at each occurrence, is selected from H, $C_{1-6}$ alkyl, and $C_{3-6}$ cycloalkyl;

$R^4$ is absent, taken with the nitrogen to which it is attached to form an N-oxide, or taken with the nitrogen to which it is attached to form a quaternary salt comprising a compound of formula (I) and a counterion and is selected from $C_{1-8}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^5$ is selected from a $(CR^{5'}R^{5"})_r$—$C_{3-10}$ carbocyclic residue substituted with 0–5 $R^{10}$ and a $(CR^{5'}R^{5"})_r$-5–10 membered heterocyclic system containing 1–4 heteroatoms selected from N, O, and S, substituted with 0–3 $R^{10}$;

$R^{5'}$ and $R^{5"}$, at each occurrence, are selected from H, $C_{1-6}$ alkyl, $(CH_2)_rC_{3-6}$ cycloalkyl, and phenyl;

alternatively, $R^5$ and $R^6$ join to form a 5, 6, or 7-membered spirocycle, containing 0–3 heteroatoms selected from N, O, and S, substituted with 0–3 $R^{16}$;

$R^6$, at each occurrence, is selected from H, $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^7$, at each occurrence, is selected from $C_{1-8}$ alkyl, $C_{2-8}$ alkenyl, $C_{2-8}$ alkynyl, F, Cl, Br, I, $(CH_2)_rOH$, $(CH_2)_rSH$, $(CH_2)_rOR^{7d}$, $(CH_2)_rSR^{7d}$, $(CH_2)_rNR^{7a}R^{7a'}$, $C_{1-6}$ haloalkyl, a $(CH_2)_r$—$C_{3-6}$ carbocyclic residue substituted with 0–3 $R^{7c}$;

$R^{7a}$ and $R^{7a'}$, at each occurrence, are selected from H, $C_{1-6}$ alkyl, $(CH_2)_rC_{3-6}$ cycloalkyl, and phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ cycloalkyl, and phenyl substituted with 0–3 $R^{7e}$;

$R^{7c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-6}$ alkyl, OH, SH, $(CH_2)_rSC_{1-6}$ alkyl, $(CH_2)_rNR^{7d}R^{7d}$, $C(O)C_{1-6}$ alkyl, and $(CH_2)_r$phenyl;

$R^{7d}$, at each occurrence, is selected from H, $C_{1-6}$ alkyl, and $C_{3-6}$ cycloalkyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, $C_{3-6}$ cycloalkyl, and phenyl;

$R^{7'}$, at each occurrence, is selected from H, $C_{1-8}$ alkyl, $C_{2-8}$ alkenyl, $C_{2-8}$ alkynyl, $(CH_2)_qOH$, $(CH_2)_qSH$, $(CH_2)_qOR^{7b}$, $(CH_2)_qSR^{7b}$, $(CH_2)_qNR^{7a}R^{7a'}$, $(CH_2)_rC(O)OH$, $C_{1-6}$ haloalkyl, a $(CH_2)_r$—$C_{3-6}$ carbocyclic residue substituted with 0–3 $R^{7c}$;

$R^8$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{8a}R^{8a'}$, $(CHR')_rOH$, $(CHR')_rO(CHR')_rR^{8d}$, $(CHR')_rSH$, $(CHR')_rC(O)H$, $(CHR')_rS(CHR')_rR^{8d}$, $(CHR')_rC(O)OH$, $(CHR')_rC(O)(CHR')_rR^{8b}$, $(CHR')_rC(O)NR^{8a}R^{8a'}$, $(CHR')_rNR^{8f}C(O)(CHR')_rR^{8b}$, $(CHR')_rC(O)O(CHR')_rR^{8d}$, $(CHR')_rOC(O)(CHR')_rR^{8b}$, $(CHR')_rC(=NR^{8f})NR^{8a}R^{8a'}$, $(CHR')_rNHC(=NR^{8f})NR^{8f}R^{8f}$, $(CHR')_rS(O)_p(CHR')_rR^{8b}$, $(CHR')_rS(O)_2NR^{8a}R^{8a'}$, $(CHR')_rNR^{8f}S(O)_2(CHR')_rR^{8b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{8e}$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{8e}$;

$R^{8a}$ and $R^{8a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–2 $R^{8e}$;

$R^{8b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{8e}$, and $(CH_2)_r$-5–6 membered heterocyclic system containing 1–4 heteroatoms selected from N, O, and S, substituted with 0–2 $R^{8e}$;

$R^{8d}$, at each occurrence, is selected from $C_{2-8}$ alkenyl, $C_{2-8}$ alkynyl, $C_{1-6}$ alkyl substituted with 0–3 $R^{8e}$, a $(CH_2)_r$—$C_{3-10}$ carbocyclic residue substituted with 0–3 $R^{8e}$, and a $(CH_2)_r$-5–6 membered heterocyclic system containing 1–4 heteroatoms selected from N, O, and S, substituted with 0–3 $R^{8e}$;

$R^{8e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{8f}R^{8f}$, and $(CH_2)_r$phenyl;

$R^{8f}$, at each occurrence, is selected from H, $C_{1-5}$ alkyl, $C_{3-6}$ cycloalkyl, and phenyl;

$R^9$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{9a}R^{9a'}$, $(CHR')_rOH$, $(CHR')_rO(CHR')_rR^{9d}$, $(CHR')_rSH$, $(CHR')_rC(O)H$, $(CHR')_rS(CHR')_rR^{9d}$, $(CHR')_rC(O)OH$, $(CHR')_rC(O)(CHR')_rR^{9b}$, $(CHR')_rC(O)NR^{9a}R^{9a'}$, $(CHR')_rNR^{9f}C(O)(CHR')_rR^{9b}$, $(CHR')_rC(O)O(CHR')_rR^{9d}$, $(CHR')_rOC(O)(CHR')_rR^{9b}$, $(CHR')_rC(=NR^{9f})NR^{9a}R^{9a'}$, $(CHR')_rNHC(=NR^{9f})NR^{9f}R^{9f}$, $(CHR')_rS(O)_p(CHR')_rR^{9b}$, $(CHR')_rS(O)_2NR^{9a}R^{9a'}$, $(CHR')_rNR^{9f}S(O)_2(CHR')_rR^{9b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{9e}$, and a $(CH_2)_r$-5–10 membered heterocyclic system containing 1–4 heteroatoms selected from N, O, and S, substituted with 0–2 $R^{9e}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–2 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{9e}$, and $(CH_2)_r$-5–6 membered heterocyclic system containing 1–4 heteroatoms selected from N, O, and S, substituted with 0–2 $R^{9e}$;

$R^{9d}$, at each occurrence, is selected from $C_{2-8}$ alkenyl, $C_{2-8}$ alkynyl, $C_{1-6}$ alkyl substituted with 0–3 $R^{9e}$, a $(CH_2)_r$—$C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-5}$ alkyl, $C_{3-6}$ cycloalkyl, and phenyl;

$R^{10}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{10a}R^{10a'}$, $(CHR')_rOH$, $(CHR')_rO(CHR')_rR^{10d}$, $(CHR')_rSH$, $(CHR')_rC(O)H$, $(CHR')_rS(CHR')_rR^{10d}$, $(CHR')_rC(O)OH$, $(CHR')_rC(O)(CHR')_rR^{10b}$, $(CHR')_rC(O)NR^{10a}R^{10a'}$, $(CHR')_rNR^{10f}C(O)(CHR')_rR^{10b}$, $(CHR')_rC(O)O(CHR')_rR^{10d}$, $(CHR')_rOC(O)(CHR')_rR^{10b}$, $(CHR')_rC(=NR^{10f})NR^{10a}R^{10a'}$, $(CHR')_rNHC(=NR^{10f})NR^{10f}R^{10f}$, $(CHR')_rS(O)_p(CHR')_rR^{10b}$, $(CHR')_rS(O)_2NR^{10a}R^{10a'}$, $(CHR')_rNR^{10f}S(O)_2(CHR')_rR^{10b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{10e}$;

$R^{10a}$ and $R^{10a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–2 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{10e}$, and $(CH_2)_r$-5–6 membered heterocyclic system containing 1–4 heteroatoms selected from N, O, and S, substituted with 0–2 $R^{10e}$;

$R^{10d}$, at each occurrence, is selected from $C_{2-8}$ alkenyl, $C_{2-8}$ alkynyl, $C_{1-6}$ alkyl substituted with 0–3 $R^{10e}$, a $(CH_2)_r$—$C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$phenyl;

$R^{10f}$, at each occurrence, is selected from H, $C_{1-5}$ alkyl, $C_{3-6}$ cycloalkyl, and phenyl;

$R^{11}$, at each occurrence is selected from H, $C_{1-8}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^{11a}$;

$R^{11a}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11b}R^{11b}$, $(CH_2)_rOH$, $(CH_2)_rOR^{11c}$, $(CH_2)_rSH$, $(CH_2)_rSR^{11c}$, $(CH_2)_rC(O)R^{11b}$, $(CH_2)_rC(O)NR^{11b}R^{11b}$, $(CH_2)_rNR^{11b}C(O)R^{11b}$, $(CH_2)_rC(O)OR^{11b}$, $(CH_2)_rOC(O)R^{11c}$, $(CH_2)_rCH(=NR^{11b})NR^{11b}R^{11b}$, $(CH_2)_rNHC(=NR^{11b})NR^{11b}R^{11b}$, $(CH_2)_rS(O)_pR^{11c}$, $(CH_2)_rS(O)_2NR^{11b}R^{11b}$, $(CH_2)_rNR^{11b}S(O)_2R^{11c}$, and $(CH_2)_r$phenyl;

$R^{11b}$, at each occurrence, is selected from H, $C_{1-6}$ alkyl, $C_{3-6}$ cycloalkyl, and phenyl;

$R^{11c}$, at each occurrence, is selected from $C_{1-5}$ alkyl, $C_{3-6}$ cycloalkyl, and phenyl;

$R^{12a}$ and $R^{12a'}$, at each occurrence, are selected from H, $C_{1-6}$ alkyl substituted with 0–3 $R^{12e}$, $C_{2-8}$ alkenyl, $C_{2-8}$ alkynyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–2 $R^{12e}$;

$R^{12b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{12e}$, and $(CH_2)_r$-5–6 membered heterocyclic system containing 1–4 heteroatoms selected from N, O, and S, substituted with 0–2 $R^{12e}$;

$R^{12c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{12f}R^{12f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{12b}$, $(CH_2)_rC(O)NR^{12f}R^{12f}$, $(CH_2)_rNR^{12f}C(O)R^{12a}$, $(CH_2)_rC(O)OC_{1-4}$ alkyl, $(CH_2)_rOC(O)R^{12b}$, $(CH_2)_rC(=NR^{12f})NR^{12f}R^{12f}$, $(CH_2)_rS(O)_pR^{12b}$, $(CH_2)_rNHC(=NR^{12f})NR^{12f}R^{12f}$, $(CH_2)_rS(O)_2NR^{12f}R^{12f}$, $(CH_2)_rNR^{12f}S(O)_2R^{12b}$, and $(CH_2)_r$phenyl substituted with 0–3 $R^{12e}$;

$R^{12d}$, at each occurrence, is selected from $C_{2-8}$ alkenyl, $C_{2-8}$ alkynyl, $C_{1-6}$ alkyl substituted with 0–3 $R^{12e}$, a $(CH_2)_r$—$C_{3-10}$ carbocyclic residue substituted with 0–3 $R^{12e}$, and a $(CH_2)_r$5–6 menibered heterocyclic system containing 1–4 heteroatoms selected from N, O, and S, substituted with 0–3 $R^{12e}$;

$R^{12e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-5}$ alkyl, $C_{3-6}$ cycloalkyl, and phenyl;

w is selected from 2, 3, 4, and 5;

t is selected from 0, 1 and 2;

r is selected from 0, 1, 2, 3, 4, and 5;

q is selected from 1, 2, 3, 4, and 5; and p is selected from 1, 2, and 3.

2. The compound according to claim 1, wherein:
L is $CH_2$.

3. The compound according to claim 2, wherein:
$R^3$ is selected from H, $C_{1-6}$ alkyl, $C_{2-8}$ alkenyl, and $C_{2-8}$ alkynyl;

$R^4$ is absent, taken with the nitrogen to which it is attached to form an N-oxide, or taken with the nitrogen to which it is attached to form a quaternary salt comprising a compound of formula (I) and a counterion and is selected from $C_{1-8}$ alkyl, $(CH_2)_rC_{3-6}$ cycloalkyl, and $(CH_2)_r$-phenyl substituted with 0–3 $R^{4c}$;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $CF_3$, $(CH_2)_rOC_{1-5}$ alkyl, $(CH_2)_rOH$;

$R^6$, at each occurrence, is selected from H, $C_{1-4}$ alkyl, $(CH_2)_rC_{3-6}$ cycloalkyl, $(CF_2)_rCF_3$, $(CH_2)_rOH$, $(CH_2)_rOR^{6b}$, and $(CH_2)_r$phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

q is selected from 1, 2, and 3; and r is selected from 0, 1, 2, and 3.

4. The compound according to claim 3, wherein:
A is selected from phenyl, cyclohexyl, cyclopentyl, and cyclopropyl;

$R^7$, at each occurrence, is selected from $C_{1-8}$ alkyl, $C_{2-8}$ alkenyl, $C_{2-8}$ alkynyib, F, Cl, Br, I, $(CH_2)_rOH$, $(CH_2)_rOR^{7d}$, $(CH_2)_rNR^{7a}R^{7a'}$, $(CH_2)_rC_{3-6}$ cycloaLkyl, and $(CH_2)_r$-phenyl substituted with 0–3 $R^{7e}$;

$R^{7a}$ and $R^{7a'}$, at each occurrence, are selected from H, $C_{1-6}$ alkyl;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7e}$ is selected from H and $C_{1-6}$ alkyl;

$R^{7'}$ is H;

$R^8$, at each occurrence, is selected from $C_{1-8}$ alkyl, $(CH_2)_rC_{3-6}$ cycloalkyl, $CF_3$, Cl, Br, I, F, $(CH_2)_rNR^{8a}R^{8a'}$, $NO_2$, CN, OH, $(CH_2)_rOR^{8d}$, $(CH_2)_rC(O)R^{8b}$, $(CH_2)_rC(O)NR^{8a}R^{8a'}$, $(CH_2)_rNR^{8f}C(O)R^{8b}$, $(CH_2)_rS(O)_pR^{8b}$, $(CH_2)_rS(O)_2NR^{8a}R^{8a'}$, $(CH_2)_rNR^{8f}S(O)_2R^{8b}$, and $(CH_2)_r$phenyl substituted with 0–3 $R^{8e}$;

$R^{8a}$ and $R^{8a'}$, at each occurrence, are selected from H, $C_{1-6}$ alkyl, $C_{3-6}$ cycloalkyl, and $(CH_2)_r$phenyl substituted with 0–3 $R^{8e}$;

$R^{8b}$, at each occurrence, is selected from H, $C_{1-6}$ alkyl, $C_{3-6}$ cycloalkyl, and $(CH_2)_r$phenyl substituted with 0–3 $R^{8e}$;

$R^{8d}$, at each occurrence, is selected from $C_{1-6}$ alkyl and phenyl;

$R^{8e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{8f}$, at each occurrence, is selected from H and $C_{1-5}$ alkyl; and $R^{11}$, at each occurrence, is selected from H, and $C_{1-8}$ alkyl.

5. The compound according to claim 4, wherein:
$R^1$ is selected from a $(CR^{1'}H)_r$-carbocyclic residue substituted with 0–5 $R^9$, wherein the carbocyclic residue is selected from phenyl, $C_{3-6}$ cycloalkyl, napthyl, and adamantyl; and a $(CR^{1'}H)_r$-heterocyclic system substituted with 0–3 $R^9$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^5$ is selected from $(CR^{5'}H)_r$-phenyl substituted with 0–5 $R^{10}$; and a $(CR^{5'}H)_r$-heterocyclic system substituted with 0–3 $R^{10}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

6. The compound according to claim 2, wherein Y is selected from $NR^{11}C(=S)NR^{11}$, $NR^{11}C(=NR^a)NR^{11}$, $NR^{11}C(=CHCN)NR^{11}$, $NR^{11}C(=CHNO_2)NR^{11}$, $NR^{11}C(=C(CN)_2)NR^{11}$, $C(O)$, $S(O)_2NR^{11}$, $NR^{11}S(O)_2$, $NR^{11}S(O)_2NR^{11}$, $C(O)NR^{11}$, $NR^{11}C(O)$, $NR^{11}C(O)O$, and $OC(O)NR^{11}$.

7. The compound according to claim 6, wherein Y is selected from $NR^{11}C(=NR^a)NR^{11}$, $NR^{11}C(=CHCN)NR^{11}$, $NR^{11}C(=CHNO_2)NR^{11}$, and $NR^{11}C(=C(CN)_2)NR^{11}$.

8. The compound according to claim 1, wherein J is $CH_2$.

9. The compound according to claim 8, wherein $R^3$ is H and $R^4$ is absent.

10. The compound according to claim 9, wherein:

$R^9$, at each occurrence, is selected from $C_{1-8}$ alkyl, $(CH_2)_rC_{3-6}$ cycloalkyl, $CF_3$, Cl, Br, I, F, $(CH_2)_rNR^{9a}R^{9a'}$, $NO_2$, CN, OH, $(CH_2)_rOR^{9d}$, $(CH_2)_rC(O)R^{9b}$, $(CH_2)_rC(O)NR^{9a}R^{9a'}$, $(CH_2)_rNR^{9f}C(O)R^{9b}$, $(CH_2)_rS(O)_pR^{9b}$, $(CH_2)_rS(O)_2NR^{9a}R^{9a'}$, $(CH_2)_rNR^{9f}S(O)_2R^{9b}$, $(CH_2)_r$phenyl substituted with 0–3 $R^{9e}$, and a $(CH_2)_r$-5–6 membered heterocyclic system containing 1–4 heteroatoms selected from N, O, and S, substituted with 0–2 $R^{9e}$;

$R^{9aa}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9b}$, at each occurrence, is selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{9f}$, at each occurrence, is selected from H, and $C_{1-5}$ alkyl;

$R^{10}$, at each occurrence, is selected from $C_{1-8}$ alkyl, $(CH_2)_rC_{3-6}$ cycloalkyl, $CF_3$, Cl, Br, I, F, $(CH_2)_rNR^{10a}R^{10a'}$, $NO_2$, CN, OH, $(CH_2)_rOR^{10d}$, $(CH_2)_rC(O)R^{10b}$, $(CH_2)_rC(O)NR^{10a}R^{10a'}$, $(CH_2)_rNR^{10f}C(O)R^{10b}$, $(CH_2)_rS(O)_pR^{10b}$, $(CH_2)_rS(O)_2NR^{10a}R^{10a'}$, $(CH_2)_rNR^{10f}S(O)_2R^{10b}$, and $(CH_2)_r$phenyl substituted with 0–3 $R^{10e}$;

$R^{10a}$ and $R^{10a'}$, at each occurrence, are selected from H, $C_{1-6}$ alkyl, $C_{3-6}$ cycloalkyl, and $(CH_2)_r$phenyl substituted with 0–3 $R^{10e}$;

$R^{10b}$, at each occurrence, is selected from H, $C_{1-6}$ alkyl, $C_{3-6}$ cycloalkyl, and $(CH_2)_r$phenyl substituted with 0–3 $R^{10e}$;

$R^{10d}$, at each occurrence, is selected from $C_{1-6}$ alkyl and phenyl;

$R^{10e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{10f}$, at each occurrence, is selected from H, and $C_{1-5}$ alkyl.

11. The compound according to claim 10, wherein $R^5$ is $(CH_2)$-phenyl substituted with 0–3 $R^{10}$.

12. The compound according to claim 11, wherein $R^1$ is phenyl substituted with 0–3 $R^9$.

13. The compound according to claim 11, wherein:

X is propylene substituted with 0–3 $R^7$; and $R^7$, at each occurrence, is selected from $C_{1-3}$ alkyl, $(CH_2)_rOH$, $(CH_2)_rOR^{7d}$, $(CH_2)_rC_{3-6}$ cycloalkyl, and $(CH_2)_r$-phenyl substituted with 0–3 $R^{7e}$;

$R^{7d}$, at each occurrence, is selected from H, $C_{1-6}$ alkyl, $C_{3-6}$ cycloalkyl, and phenyl;

$R^{7e}$, at each occurrence, is selected from $C_{1-6}$ alkyl, Cl, F, Br, I, CN, $NO_2$, $(CF_2)_rCF_3$, $(CH_2)_rOC_{1-5}$ alkyl, OH, $(CH_2)_rNR^{7f}R^{7f}$; and $R^{7f}$ is selected from H and $C_{1-6}$ alkyl.

14. The compound according to claim 13, wherein:

$R^2$, at each occurrence, is selected from H, $C_{1-8}$ alkyl, $(CR^{2'}R^{2''})_qNR^{12a}R^{12a'}$, $(CR^{2'}R^{2''})_wOH$, $(CR^{2'}R^{2''})_wO(CR^{2'}R^{2''})_rR^{12d}$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a'}$, $(CR^{2'}R^{2''})_rC(O)NR^{12a}R^{12a'}$, $(CR^{2'}R^{2''})_qNR^{12f}C(O)(CR^{2'}R^{2''})_rR^{12b}$, $(CR^{2'}R^{2''})_wS(O)_2NR^{12a}R^{12a'}$, $(CR^{2'}R^{2''})_qNR^{12f}S(O)_2(CR^{2'}R^{2''})_rR^{12b}$, $C_{1-6}$ haloalkyl, $C_{2-8}$ alkenyl substituted with 0–3 $R^{12c}$, $C_{2-8}$ alkynyl substituted with 0–3 $R^{12c}$, a $(CR^{2'}R^{2''})_r$—$C_{3-10}$ carbocyclic residue substituted with 0–3 $R^{12c}$, and a $(CH_2)_r$-5–10 membered heterocyclic system containing 1–4 heteroatoms selected from N, O, and S, substituted with 0–2 $R^{12c}$;

alternatively, $R^2$ is an amino acid residue; and $R^{2'}$ and $R^{2''}$, at each occurrence, are selected from H, $C_{1-8}$ alkyl, $C_{2-8}$ alkenyl, $(CH_2)_rOH$, $(CH_2)_rOR^{2b}$, $(CH_2)_rC(O)R^{2b}$, $(CH_2)_rC(O)NR^{2a}R^{2a'}$, $(CH_2)_rNR^{2d}C(O)R^{2a}$.

15. The compound according to claim 13, wherein X is unsubstituted propylene.

16. The compound according to claim 13, wherein:

$R^5$ is substituted with 0–2 $R^{10}$;

$R^{10}$, at each occurrence, is selected from $C_{1-8}$ alkyl, $(CH_2)_rC_{3-6}$ cycloalkyl, $CF_3$, Cl, Br, I, F, $C(O)C_{1-4}$ alkyl, $(CH_2)_rNR^{10a}R^{10a'}$, CN, OH, $OCF_3$, $(CH_2)_rOR^{10d}$;

$R^{10a}$ and $R^{10a'}$, at each occurrence, are selected from H, $C_{1-6}$ alkyl, and $C_{3-6}$ cycloalkyl; and $R^{10d}$ is $C_{1-6}$ alkyl.

17. The compound according to claim 16 wherein $R^{10}$ is fluoro.

18. The compound according to claim 13 wherein:

$R^1$ is substituted with 0–2 $R^9$;

$R^9$, at each occurrence, is selected from $C_{1-8}$ alkyl, $(CH_2)_rC_{3-6}$ cycloalkyl, Cl, Br, F, $NO_2$, CN, $(CHR')_rNR^{9a}R^{9a'}$, $(CHR')_rOH$, $(CHR')_rO(CHR')_rR^{9d}$, $(CHR')_rC(O)(CHR')_rR^{9b}$, $(CHR')_rC(O)NR^{9a}R^{9a'}$, $(CHR')_rNR^{9f}C(O)(CHR')_rR^{9b}$, $(CHR')_rC(O)O(CHR')_rR^{9d}$, $(CHR')_rS(O)_p(CHR')_rR^{9b}$, $(CHR')_rS(ONR^{9a}R^{9a'}$, $(CHR')_rNR^{9f}S(O)_2(CHR')_rR^{9b}$, $CF_3$, $OCF_3$, $(CHR')_r$phenyl substituted with 0–3 $R^{9e}$, and a $(CH_2)_r$-5–10 membered heterocyclic system containing 1–4 heteroatoms selected from N, O, and S, substituted with 0–2 $R^{9e}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–2 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{9e}$, and $(CH_2)_r$-5–6 menibered heterocyclic system containing 1–4 heteroatoms selected from N, O, and S, substituted with 0–2 $R^{9e}$;

$R^{9d}$, at each occurrence, is selected from $C_{2-8}$ alkenyl, $C_{2-8}$ alkynyl, $C_{1-6}$ alkyl substituted with 0–3 $R^{9e}$, a $(CH_2)_r$—$C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl; and $R^{9f}$, at each occurrence, is selected from H, $C_{1-5}$ alkyl, $C_{3-6}$ cycloalkyl, and phenyl.

19. The compound according to claim 18, wherein $R^1$ is phenyl substituted with $R^9$ in the 3 and 5 positions.

20. The compound according to claim 19, wherein:

$R^9$, at each occurrence, is selected from $C(O)R^{9b}$, $C(O)OR^d$, $C(O)OH$, CN, and a $(CH_2)_r$-5-6 membered heterocyclic system containing 1–4 heteroatoms selected from N, O, and S, substituted with 0–2 $R^{9e}$.

21. The compound according to claim 17, wherein X is unsubstituted propylene.

22. The compound according to claim 10, wherein X is unsubstituted propylene.

23. The compound according to claim 21, wherein:

$R^2$, at each occurrence, is selected from H, $C_{1-8}$ alkyl, $(CR^{2'}R^{2''})_qNR^{12a}R^{12a'}$, $(CR^{2'}R^{2''})_wOH$, $(CR^{2'}R^{2''})_wO(CR^{2'}R^{2''})_rR^{12d}$, $(CR^{2'}R^{2''})_rC(O)(CR^{2'}R^{2''})_rR^{12b}$, $(CR^{2'}R^{2''})_wNR^{12a}C(NR^a)NR^{12a}R^{12a'}$, $(CR^{2'}R^{2''})_rC(O)NR^{12a}R^{12a'}$, $(CR^{2'}R^{2''})_qNR^{12f}C(O)(CR^{2'}R^{2''})_rR^{12b}$, $(CR^{2'}R^{2''})_wS(O)_2NR^{12a}R^{12a'}$, $(CR^{2'}R^{2''})_qNR^{12f}S(O)_2(CR^{2'}R^{2''})_rR^{12b}$, $C_{1-6}$ haloalkyl, $C_{2-8}$ alkenyl substituted with 0–3 $R^{12c}$, $C_{2-8}$ alkynyl substituted with 0–3 $R^{12c}$, a $(CR^{2'}R^{2''})_r$—$C_{3-10}$ carbocyclic residue substituted with 0–3 $R^{12c}$, and a $(CH_2)_r$-5- membered heterocyclic system containing 1–4 heteroatoms selected from N, O, and S, substituted with 0–2 $R^{12c}$;

alternatively, $R^2$ is an amino acid residue; and $R^{2'}$ and $R^{2''}$, at each occurrence, are selected from H, $C_{1-8}$ alkyl, $C_{2-8}$ alkenyl, $(CH_2)_rOH$, $(CH_2)_rOR^{2b}$, $(CH_2)_rC(O)R^{2b}$, $(CH_2)_rC(O)NR^{2a}R^{2a'}$, and $(CH_2)_rNR^{2d}C(O)R^{2a}$.

24. A pharmaceutical composition comprising a pharmaceutically acceptable carrier and a therapeutically effective amount of a compound according to claim 1, or a pharmaceutically acceptable salt thereof.

25. A pharmaceutical composition comprising a pharmaceutically acceptable carrier and a therapeutically effective amount of a compound according to claim 12, or a pharmaceutically acceptable salt thereof.

26. A method for modulation of chemokine receptor activity comprising administering to a patient in need thereof a therapeutically effective amount of claim 1.

27. A method for treating inflammatory disorders which are at least partially mediated by CCR-3 comprising administering to a patient in need thereof a therapeutically effective amount of a compound according to claim 1, or a pharmaceutically acceptable salt thereof.

28. A method for treating disorders comprising administering to a patient in need thereof a therapeutically effective amount of a compound according to claim 1, wherein the disorder is selected from asthma, allergic rhinitis, atopic dermatitis, inflammatory bowel diseases, idiopathic pulmonary fibrosis, bullous pemphigoid, allergic colitis, eczema, conjunctivitis, familial eosinophilia, eosinophilic cellulitis, eosinophilic pneumonias, eosinophilic fascists, and eosinophilic gas troenteritis.

29. The method according to claim 28, wherein the disorder is selected from asthma, allergic rhinitis, atopic dermatitis, and inflammatory bowel diseases.

30. The method according to claim 29, wherein the disorder is asthma.

31. A method for modulation of chemokine receptor activity comprising administering to a patient in need thereof, a therapeutically effective amount of claim 12.

32. A method for treating inflammatory disorders comprising which are at least partially mediated by CCR-3 administering to a patient in need thereof a therapeutically effective amount of a compound according to claim 12, or a pharmaceutically acceptable salt thereof.

33. A method for treating disorders comprising administering to a patient in need thereof a therapeutically effective amount of a compound according to claim 12, wherein the disorder is selected from asthma, allergic rhinitis, atopic dermatitis, inflammatory bowel diseases, idiopathic pulmonary fibrosis, bullous pemphigoid, allergic colitis, eczema, conjunctivitis, familial eosinophilia, eosinophilic cellulitis, eosinophilic pneumonias, eosinophilic fascists, and eosinophilic gastroenteritis.

34. The method according to claim 33, wherein the disorder is selected from asthma, allergic rhinitis, atopic dermatitis, and inflammatory bowel diseases.

35. The method according to claim 34, wherein the disorder is asthma.

* * * * *